(12) United States Patent
Greenhouse et al.

(10) Patent No.: US 7,638,517 B2
(45) Date of Patent: Dec. 29, 2009

(54) 3-AMINO-1-ARYLPROPYL AZAINDOLES AND USES THEREOF

(75) Inventors: Robert Greenhouse, Newark, CA (US); Saul Jaime-Figueroa, Fremont, CA (US); Stephen M. Lynch, San Jose, CA (US); Lubica Raptova, Sunnyvale, CA (US); Karin Ann Stein, Mountain View, CA (US); Robert James Weikert, Boulder Creek, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 253 days.

(21) Appl. No.: 11/605,729

(22) Filed: Nov. 29, 2006

(65) Prior Publication Data

US 2007/0123535 A1 May 31, 2007

Related U.S. Application Data

(60) Provisional application No. 60/741,272, filed on Nov. 30, 2005.

(51) Int. Cl.
| | | |
|---|---|---|
| A61K 31/519 | (2006.01) | |
| A61K 31/506 | (2006.01) | |
| A61K 31/4745 | (2006.01) | |
| C07D 487/02 | (2006.01) | |
| C07D 471/02 | (2006.01) | |

(52) U.S. Cl. .............. 514/252.02; 514/265.1; 514/300; 514/303; 546/112; 546/119; 544/280; 544/333

(58) Field of Classification Search ........ 546/113, 546/112, 119; 544/238, 333; 514/300, 303, 514/252.02, 265.1
See application file for complete search history.

(56) References Cited

U.S. PATENT DOCUMENTS

| 2,708,197 | A | 5/1955 | Speeter | |
|---|---|---|---|---|
| 2,752,358 | A | 6/1956 | Ehrhart et al. | |
| 2,984,670 | A | 5/1961 | Szmuszkovicz et al | |
| 2005/0222148 | A1* | 10/2005 | Kim et al. ........ | 514/232.5 |
| 2006/0025467 | A1 | 2/2006 | Greenhouse et al. | |
| 2007/0088058 | A1* | 4/2007 | Shah et al. ........ | 514/345 |
| 2007/0105914 | A1* | 5/2007 | Armstrong et al. ..... | 514/357 |

FOREIGN PATENT DOCUMENTS

| DE | 849108 (C1) | 7/1949 |
|---|---|---|
| EP | 0 179 546 A2 | 4/1986 |
| EP | 0 509 402 A1 | 10/1992 |
| EP | 0 534 343 A1 | 3/1993 |
| EP | 0 600 830 A1 | 6/1994 |
| EP | 0 506 532 B1 | 9/1994 |
| EP | 0 775 694 A2 | 5/1997 |
| EP | 0 780 389 A1 | 6/1997 |
| EP | 0 887 348 A1 | 12/1998 |
| FR | 2 814 073 A1 | 9/2000 |
| GB | 705652 | 9/1950 |
| GB | 992731 (A) | 9/1963 |
| JP | 03 14562 (A) | 1/1991 |
| WO | WO 94/12478 A1 | 6/1994 |
| WO | WO 97/10219 A1 | 3/1997 |
| WO | WO 97/44329 A1 | 11/1997 |
| WO | WO 97/46511 A1 | 12/1997 |
| WO | WO 98/43942 A1 | 10/1998 |
| WO | WO 99/16755 A1 | 4/1999 |
| WO | WO 99/21553 A1 | 5/1999 |
| WO | WO 99/21557 A1 | 5/1999 |
| WO | WO 00/02551 A2 | 1/2000 |
| WO | WO 00/02551 A3 | 1/2000 |
| WO | WO 00/02556 A1 | 1/2000 |
| WO | WO 01/32622 A1 | 5/2001 |
| WO | WO 02/69965 A1 | 9/2002 |
| WO | WO 03/035005 A2 | 5/2003 |
| WO | WO 03/035005 A3 | 5/2003 |
| WO | WO 03/053938 A1 | 7/2003 |
| WO | WO 03/057213 A2 | 7/2003 |
| WO | WO 03/057213 A3 | 7/2003 |
| WO | WO 03/066622 A1 | 8/2003 |
| WO | 21003077847 | * 9/2003 |
| WO | 2003086288 | * 10/2003 |
| WO | 2003087037 | * 10/2003 |
| WO | WO 2005/005439 A1 | 1/2005 |

OTHER PUBLICATIONS

Ganellin, C.R., et. al., "Aminoalkylation of Metal Derivatives of Indole. Part III. Alkylation of Lithio-derivatives of N-Substituted Indoles with 1-Chloro-2-dimethyl-aminoethane," *J. Chem. Society* (1969) pp. 1537-1540.

Kraxner, J., et. al., "Azepino- and Diazepinoindoles: Synthesis and Dopamine Receptor Binding Profiles," *Archiv. der Pharmazie.* (2000) vol. 333 (9) pp. 287-292.

(Continued)

*Primary Examiner*—D. Margaret Seaman
*Assistant Examiner*—Niloofar Rahmani
(74) *Attorney, Agent, or Firm*—Robert C. Hall

(57) ABSTRACT

The present invention provides compounds of the formula:

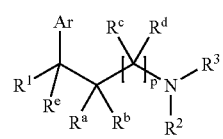

or pharmaceutically acceptable salts, solvates or prodrugs thereof, wherein p, Ar, $R^1$, $R^2$, $R^3$, $R^a$, $R^b$, $R^c$, $R^d$ and $R^e$ are defined herein. Also provided are pharmaceutical compositions, methods of using, and methods of preparing the compounds.

9 Claims, No Drawings

OTHER PUBLICATIONS

Lindner, E. "Über ein neues Antihistaminicum, das-1-Phenyl-1-Pyridyl-(2)-3-dimethylaminopropan und sein Salz mit der p-Aminosalicylsäure (A vil)", Naunyn-Schmiedbergs Archiv für Pharmakologie und Experimentelle Pathologie, (1950) vol. 211, pp. 328-344.

Schmidt, A. M. et. al., "Synthesis of Pharmacologically Relevant Indoles with Amine Side Chains via Tandem Hydroformylation/Fischer Indole Synthesis," *J. Organic Chemistry* (2005) vol. 70 (14) pp. 5528-5535.

* cited by examiner

3-AMINO-1-ARYLPROPYL AZAINDOLES AND USES THEREOF

CROSS REFERENCE TO RELATED APPLICATIONS

This application is entitled to the benefit of provisional patent application Ser. No. 60/741,272 filed on Nov. 30, 2005, the disclosure of which is incorporated herein by reference.

FIELD OF THE INVENTION

This invention pertains to 3-amino-1-arylpropyl substituted heteroaryl compounds and methods for using the same. In particular, compounds of the present invention are useful for treatment of diseases associated with monoamine reuptake inhibitors.

BACKGROUND OF THE INVENTION

Monoamine deficiency has been long been linked to depressive, anxiolytic and other disorders (see, e.g.: Charney et al., *J. Clin. Psychiatry* (1998) 59, 1-14; Delgado et al., *J. Clin. Psychiatry* (2000) 67, 7-11; Resser et al., *Depress. Anxiety* (2000) 12 (Suppl 1) 2-19; and Hirschfeld et al., *J. Clin. Psychiatry* (2000) 61, 4-6. In particular, serotonin (5-hydroxytryptamine) and norepinephrine are recognized as key modulatory neurotransmitters that play an important role in mood regulation. Selective serotonin reuptake inhibitors (SSRIs) such as fluoxetine, sertraline, paroxetine, fluvoxamine, citalopram and escitalopram have provided treatments for depressive disorders (Masand et al., *Harv. Rev. Psychiatry* (1999) 7, 69-84). Noradrenaline or norepinephrin reuptake inhibitors such as reboxetine, atomoxetine, desipramine and nortryptyline have provided effective treatments for depressive, attention deficit and hyperactivity disorders (Scates et al., *Ann. Pharmacother.* (2000) 34, 1302-1312; Tatsumi et al., *Eur. J. Pharmacol.* (1997) 340, 249-258).

Enhancement of serotonin and norepinephrine neurotransmission is recognized to be synergistic in the pharmacotherapy of depressive and anxiolytic disorders, in comparison with enhancement of only serotonin or norepinephrine neurotransmission alone (Thase et al., *Br. J. Psychiatry* (2001) 178, 234, 241; Tran et al., *J. Clin. Psychopharmacology* (2003) 23, 78-86). Dual reuptake inhibitors of both serotonin and norepinephrine, such as duloxetine, milnacipran and venlafaxine are currently under development for treatment of depressive and anxiolytic disorders (Mallinckrodt et al., *J. Clin. Psychiatry* (2003) 5(1) 19-28; Bymaster et al., *Expert Opin. Investig. Drugs* (2003) 12(4) 531-543). Dual reuptake inhibitors of serotonin and norepinephrine also offer potential treatments for schizophrenia and other psychoses, dyskinesias, drug addition, cognitive disorders, Alzheimer's disease, obsessive-compulsive behaviour, attention deficit disorders, panic attacks, social phobias, eating disorders such as obesity, anorexia, bulimia and "binge-eating", stress, hyperglycaemia, hyperlipidemia, non-insulin-dependent diabetes, seizure disorders such as epilepsy, and treatment of conditions associated with neurological damage resulting from stroke, brain trauma, cerebral ischaemia, head injury and haemorrhage. Dual reuptake inhibitors of serotonin and norepinephrine also offer potential treatments for disorders and disease states of the urinary tract, and for pain and inflammation.

There is accordingly a need for compounds that are effective as serotonin reuptake inhibitors, norepinephrine reuptake inhibitors, and/or dual reuptake inhibitors of serotonin and norepinephrine, as well as methods of making and using such compounds in the treatment of depressive, anxiolytic, genitourinary, and other disorders. The present invention satisfies these needs.

SUMMARY OF THE INVENTION

One aspect of the invention provides compounds of formula I:

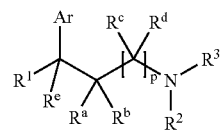

or a pharmaceutically acceptable salt thereof, wherein:
p is 1 or 2;
Ar is:
  pyrrolopyridinyl selected from the group consisting of pyrrolopyridin-1-yl, pyrrolopyridin-2-yl, and pyrrolopyridin-3-yl, each of which is optionally substituted;
  pyrrolopyridinyl N-oxide selected from the group consisting of pyrrolopyridin-1-yl N-oxide, pyrrolopyridin-2-yl N-oxide, and pyrrolopyridin-3-yl N-oxide, each of which is optionally substituted; or
  pyrrolopyrimidinyl selected from the group consisting of pyrrolopyrimidin-5-yl, pyrrolopyrimidin-6-yl, and pyrrolopyrimidin-7-yl, each of which is optionally substituted;
$R^1$ is:
  (a) aryl selected from phenyl and naphthyl, each optionally substituted; or
  (b) heteroaryl selected from indolyl, pyridinyl, thienyl, furanyl, pyrimidinyl, pyridazinyl, pyrazinyl, oxazolyl, thiazolyl, isoxazolyl, isothiazolyl, imidazolyl, pyrazolyl, quinolinyl and isoquinolinyl, each optionally substituted;
  (c) optionally substituted arylalkyl;
  (d) optionally substituted heteroarylalkyl;
  (e) cycloalkyl;
  (f) cycloalkylmethyl; or
  (g) branched alkyl;
$R^2$ is:
  (a) hydrogen;
  (b) alkyl;
  (c) hydroxyalkyl;
  (d) alkoxyalkyl;
  (e) benzyl; or
  or $R^2$ is a bond that connects the nitrogen atom to one of the ring carbon atoms of Ar;
$R^3$ is:
  (a) hydrogen;
  (b) alkyl;
  (c) hydroxyalkyl;
  (d) alkoxyalkyl;
  (e) benzyl; or
  (f) $R^2$ and $R^3$ together with the nitrogen to which they are attached may form an optionally substituted four to seven membered ring that optionally includes an additional heteroatom selected from N, O and S;

$R^a$ is:
   hydrogen;
   fluoro; or
   alkyl;
$R^b$ is:
   hydrogen;
   alkyl;
   hydroxy;
   alkoxy;
   fluoro; or
   hydroxyalkyl;
or one of $R^2$ and $R^3$ together with one of $R^a$ and $R^b$ and the atoms to which they are attached may form a five or six membered ring that optionally includes an additional heteroatom selected from O, N and S;
$R^c$ and $R^d$ each independently is:
   hydrogen; or
   alkyl;
   or $R^c$ and $R^d$ together form =O, =S, or =NR$^f$, wherein R$^f$ is hydrogen, alkyl, or —OR$^g$, wherein R$^g$ is hydrogen or alkyl;
   or on of $R^2$ and $R^3$ together with one of $R^c$ and $R^d$ together with the atoms to which they are attached may form a four to six membered ring that optionally includes an additional heteroatom selected from O, N and S; and
$R^e$ is hydrogen or alkyl.

The invention also provides pharmaceutical compositions, methods of using, and methods of preparing the aforementioned compounds.

The invention also provides pharmaceutical compositions, methods of using, and methods of preparing the aforementioned compounds.

The methods comprise, in certain embodiments:

reacting an azaindole a:

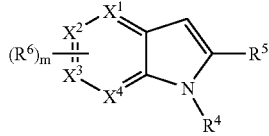

with an aldehyde b:

in the presence of 2,2-dimethyl-[1,3]dioxane-4,6-dione, to form a compound c:

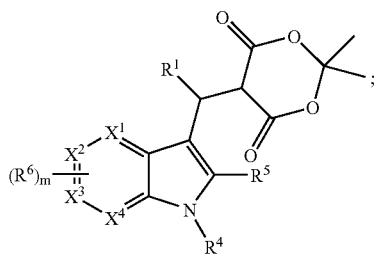

reacting the compound c with an amine d:

in the presence of pyridine, to form a compound of formula e:

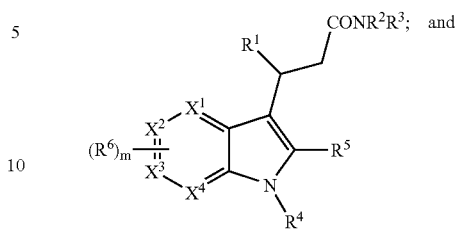

reducing compound e to form a compound of formula VI:

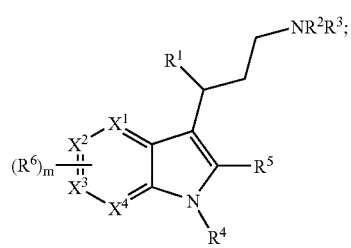

wherein one of $X^1$, $X^2$, $X^3$, and $X^4$ is N and the others are CH, and m, $R^1$, $R^2$, $R^3$, $R^4$, $R^5$ and $R^6$ are as defined herein.

In still other embodiments the subject methods comprise:
reacting an azaindole k

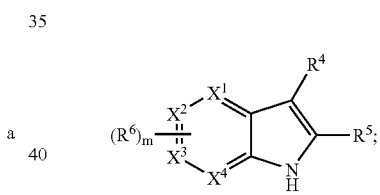

with an acrylic ester l

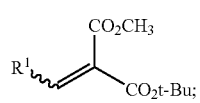

to form an azaindole propionic ester m

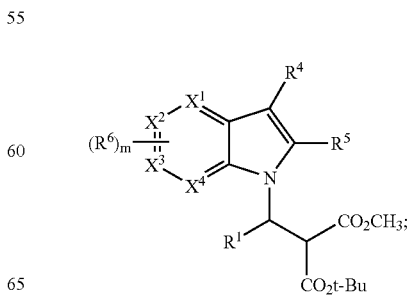

reducing azaindole propionic ester m to afford an indole propanol n

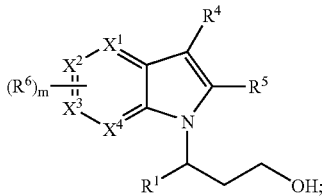

treating azaindole propanol n with methanesulfonyl chloride, followed by lithium chloride, to provide an azaindole propyl chloride o

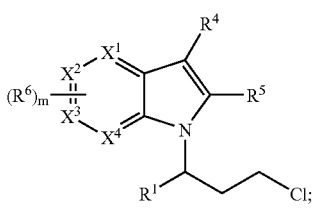

and reacting azaindole propyl chloride o with an amine d

optionally in the presence of sodium iodide, to yield a compound of formula IV;

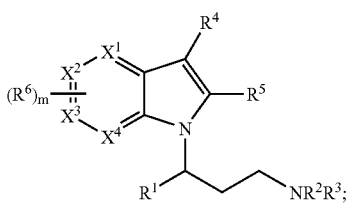

wherein one or two (e.g., $X^2$, and $X^4$) of $X^1$, $X^2$, $X^3$, and $X^4$ are N and the others are CH, and m, $R^1$, $R^2$, $R^3$, $R^4$, $R^5$ and $R^6$ are as defined herein.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like. "Branched alkyl" means isopropyl, isobutyl, tert-butyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, tert-butoxy and the like.

"Alkoxyalkyl" means a moiety of the formula —R'—R", where R' is alkylene and R" is alkoxy as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —R'—R", where R' is oxo and R" is alkyl as defined herein.

"Alkylsulfonyl" means a moiety of the formula —R'—R", where R' is —$SO_2$— and R" is alkyl as defined herein.

"Alkylsulfonylalkyl" means a moiety of the formula $R^a$—$SO_2$—$R^b$—, where $R^a$ is alkyl and $R^b$ is alkylene as defined herein. Exemplary alkylsulfonylalkyl groups include, by way of example, 3-methanesulfonylpropyl, 2-methanesulfonylethyl, 2-methanesulfonylpropy, and the like.

"Alkylsulfonyloxy" means a moiety of the formula $R^a$—$SO_2$—O—, where $R^a$ is alkyl as defined herein.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Aryloxy" means a moiety of the formula —OR, wherein R is an aryl moiety as defined herein.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Aralkoxy" means a moiety of the formula —OR, wherein R is an aralkyl moiety as defined herein.

"Azaindole" means a group of the formula

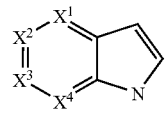

wherein one or two of any of $X^1$, $X^2$, $X^3$ and $X^4$ is N (aza), and the others are carbon. "Azaindoles" may be optionally substituted, as defined herein for heteroaryls, at position 1, 2 and 3, and at any of positions 4-through seven that are not nitrogen. "Azaindole" thus includes: "pyrrolopyrimidines" of the above formula wherein $X^2$ and $X^4$ are N; "pyrrolopyrimidines" of the above formula wherein $X^1$ and $X^3$ are N; "pyrrolopyrazines" of the above formula wherein $X^1$ and $X^4$ are N; "pyrrolopyridines" of the above formula wherein $X^1$ is N; "pyrrolopyridines" of the above formula wherein $X^2$ is N; "pyrrolopyridines" of the above formula wherein $X^3$ is N; and "pyrrolopyridines" of the above formula wherein $X^4$ is N;

"Cyanoalkyl" means a moiety of the formula —R'—R", where R' is alkylene as defined herein and R" is cyano or nitrile.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkyloxy" and "cycloalkoxy", which may be used interchangeably, mean a group of the formula —OR wherein R is cycloalkyl as defined herein. Exemplary cycloalkyloxy include cyclopropyloxy, cyclobutyloxy, cyclopentyloxy, cyclohexyloxy and the like.

"Cycloalkylalkyl" means a moiety of the formula —R'—R", where R' is alkylene and R" is cycloalkyl as defined herein.

"Cycloalkylalkyloxy" and "cycloalkylalkoxy", which may be used interchangeably, mean a group of the formula —OR wherein R is cycloalkylalkyl as defined herein. Exemplary cycloalkyloxy include cyclopropylmethoxy, cyclobutylmethoxy, cyclopentylmethoxy, cyclohexylmethoxy and the like.

"Heteroalkyl" means an alkyl radical as defined herein, including a branched $C_4$-$C_7$-alkyl, wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, thiophenyl, furanyl, pyranyl, pyridinyl, pyrrolyl, pyrazolyl, pyrimidyl, quinolinyl, isoquinolinyl, benzofuryl, benzofuranyl, benzothiophenyl, benzothiopyranyl, benzimidazolyl, benzoxazolyl, benzooxadiazolyl, benzothiazolyl, benzothiadiazolyl, benzopyranyl, indolyl, indazolyl, azaindolyl. pyrrolopyridine, pyrrolopyrimidine, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

"Heteroarylalkyl" and "heteroaralkyl", which may be used interchangeably, mean a radical-$R^aR^b$ where $R^a$ is an alkylene group and $R^b$ is a heteroaryl group as defined herein The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Haloalkoxy" means a moiety of the formula —OR, wherein R is a haloalkyl moiety as defined herein. Examples of haloalkoxy moieties include, but are not limited to, trifluoromethoxy, difluoromethoxy, 2,2,2-trifluoroethoxy, and the like.

"Hydroxyalkyl" refers to a subset of heteroalkyl and refers in particular to an alkyl moiety as defined herein that is substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl, and the like.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Pyrrolopyrimidine" means a heteroaryl of the formula

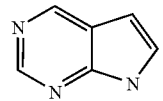

(pyrrolo[2,3-d]pyrimidine) or

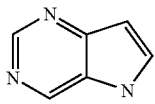

(pyrrolo[3,2-d]pyrimidine), which may be optionally substituted as defined herein. "Pyrrolopyrimidine" is an "azaindole" as defined herein.

"Pyrrolopyridine" means a heteroaryl of the formula

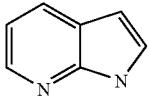

(pyrrolo[2,3-b]pyridine),

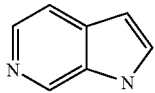

(pyrrolo[2,3-c]pyridine),

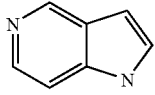

(Pyrrolo[3,2-c]pyridine) or

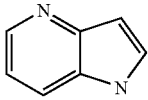

(pyrrolo[3,2-b]pyridine), which may be optionally substituted as defined herein. "Pyrrolopyridine" is an "azaindole" as defined herein.

"Optionally substituted", when used in association with "aryl", phenyl", "heteroaryl" (including indolyl such as indol-1-yl, indol-2-yl and indol-3-yl, 2,3-dihydroindolyl such as 2,3-dihydroindol-1-yl, 2,3-dihydroindol-2-yl and 2,3-dihydroindol-3-yl, indazolyl such as indazol-1-yl, indazol-2-yl and indazol-3-yl, benzimidazolyl such as benzimidazol-1-yl and benzimidazol-2-yl, benzofuranyl such as benzofuran-2-yl and benzofuran-3-yl, benzothiophenyl such as benzothiophen-2-yl and benzothiophen-3-yl, benzoxazol-2-yl, benzothiazol-2-yl, thienyl, furanyl, pyridinyl, pyrimidinyl, pyridazinyl, pyrazinyl, oxazolyl, thiazolyl, isoxazolyl, isothiazolyl, imidazolyl, pyrazolyl and quinolinyl) "or "heterocyclyl", means an aryl, phenyl, heteroaryl or heterocyclyl which is optionally substituted independently with one to four substituents, preferably one or two substituents selected from alkyl, cycloalkyl, alkoxy, halo, haloalkyl, haloalkoxy, cyano, nitro, heteroalkyl, amino, acylamino, mono-alkylamino, di-alkylamino, hydroxyalkyl, alkoxyalkyl, benzyloxy, cycloalkylalkyl, cycloalkoxy, cycloalkylalkoxy, alkylsulfonyloxy, optionally substituted thienyl, optionally substituted pyrazolyl, optionally substituted pyridinyl, morpholinocarbonyl, $-(CH_2)_q-S(O)_rR^f$; $-(CH_2)_q-NR^gR^h$; $-(CH_2)_q-C(=O)-NR^gR^h$; $-(CH_2)_q-C(=O)-C(=O)-NR^gR^h$; $-(CH_2)_q-SO_2-NR^gR^h$; $-(CH_2)_q-N(R^f)-C(=O)-R^i$; $-(CH_2)_q-C(=O)-R^i$; or $-(CH_2)_q-N(R^f)-SO_2-R^g$; where q is 0 or 1, r is from 0 to 2, $R^f$, $R^g$, and $R^h$ each independently is hydrogen or alkyl, and each $R^i$ is independently hydrogen, alkyl, hydroxy, or alkoxy.

"Leaving group" means the group with the meaning conventionally associated with it in synthetic organic chemistry, i.e., an atom or group displaceable under substitution reaction conditions.

Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like.

Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to formula I in vivo when such prodrug is administered to a mammalian subject. Prodrugs of a compound of formula I are prepared by modifying one or more functional group(s) present in the compound of formula I in such a way that the modification(s) may be cleaved in vivo to release the parent compound. Prodrugs include compounds of formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of formula I, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, see Bundegaard, H. "Design of Prodrugs" p 1-92, Elsevier, New York-Oxford (1985), and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Skilled persons will know how to choose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Disease states" associated with serotonin and norepinephrine neurotransmission include depressive and anxiolytic disorders, as well as schizophrenia and other psychoses, dyskinesias, drug addition, cognitive disorders, Alzheimer's disease, attention deficit disorders such as ADHD, obsessive-compulsive behaviour, panic attacks, social phobias, eating disorders such as obesity, anorexia, bulimia and "binge-eating", stress, hyperglycaemia, hyperlipidaemia, non-insulin-dependent diabetes, seizure disorders such as epilepsy, and treatment of conditions associated with neurological damage resulting from stroke, brain trauma, cerebral ischaemia, head injury, haemorrhage, and disorders and disease states of the urinary tract.

"Depression" as used herein includes, but is not limited to, major depression, long-term depression, dysthymia, mental states of depressed mood characterised by feelings of sadness, despair, discouragement, "blues", melancholy, feelings of low self esteem, guilt and self reproach, withdrawal from interpersonal contact, and somatic symptoms such as eating and sleep disturbances.

"Anxiety" as used herein includes, but is not limited to, unpleasant or undesirable emotional states associated with psychophysiological responses to anticipation of unreal, imagined or exaggerated danger or harm, and physical concomitants such as increased heart rate, altered respiration rate, sweating, trembling, weakness and fatigue, feelings of impending danger, powerlessness, apprehension and tension.

"Disorders of the urinary tract" or "uropathy" used interchangeably with "symptoms of the urinary tract" means the pathologic changes in the urinary tract. Examples of urinary tract disorders include, but are not limited to, stress incontinence, urge incontinence, benign prostatic hypertrophy (BPH), prostatitis, detrusor hyperreflexia, outlet obstruction, urinary frequency, nocturia, urinary urgency, overactive bladder, pelvic hypersensitivity, urethritis, prostatodynia, cystitis, idiophatic bladder hypersensitivity, and the like.

"Disease states associated with the urinary tract" or "urinary tract disease states" or "uropathy" used interchangeably with "symptoms of the urinary tract" mean the pathologic changes in the urinary tract, or dysfunction of urinary bladder smooth muscle or its innervation causing disordered urinary storage or voiding. Symptoms of the urinary tract include, but are not limited to, overactive bladder (also known as detrusor hyperactivity), outlet obstruction, outlet insufficiency, and pelvic hypersensitivity.

"Overactive bladder" or "detrusor hyperactivity" includes, but is not limited to, the changes symptomatically manifested as urgency, frequency, altered bladder capacity, incontinence, micturition threshold, unstable bladder contractions, sphincteric spasticity, detrusor hyperreflexia (neurogenic bladder), detrusor instability, and the like.

"Outlet obstruction" includes, but is not limited to, benign prostatic hypertrophy (BPH), urethral stricture disease, tumors, low flow rates, difficulty in initiating urination, urgency, suprapubic pain, and the like.

"Outlet insufficiency" includes, but is not limited to, urethral hypermobility, intrinsic sphincteric deficiency, mixed incontinence, stress incontinence, and the like.

"Pelvic Hypersensitivity" includes, but is not limited to, pelvic pain, interstitial (cell) cystitis, prostatodynia, prostatitis, vulvadynia, urethritis, orchidalgia, overactive bladder, and the like.

"Pain" means the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (*Dorland's Illustrated Medical Dictionary*, 28th Edition, W. B. Saunders Company, Philadelphia, Pa.). The goal of treatment of pain is to reduce the degree of severity of pain perceived by a treatment subject.

"Neuropathic pain" means the pain resulting from functional disturbances and/or pathological changes as well as noninflammatory lesions in the peripheral nervous system. Examples of neuropathic pain include, but are not limited to, thermal or mechanical hyperalgesia, thermal or mechanical allodynia, diabetic pain, entrapment pain, and the like.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:

(i) preventing the disease state, i.e. causing the clinical symptoms of the disease state not to develop in a subject that may be exposed to or predisposed to the disease state, but does not yet experience or display symptoms of the disease state.

(ii) inhibiting the disease state, i.e., arresting the development of the disease state or its clinical symptoms, or (iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen atom. For convenience, the FUPAC numbering of the positions of representative pyrrolopyridinyl compounds described herein are shown by the formula

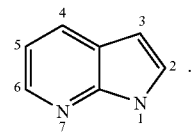

The positional numbering of pyrrolopyridinyl compounds remains the same for compounds in which the aza substitution shown at the 7-position in the above formula is moved to the 4-, 5- or 6-position of the above formula.

Pyrrolopyrimidinyl and related compounds described herein have IUPAC numbering as shown by the formulas:

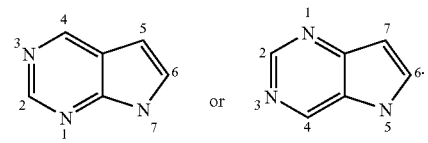

Whenever a chiral carbon is present in a chemical structure, it is intended that all stereoisomers associated with that chiral carbon are encompassed by the structure.

All patents and publications identified herein are incorporated herein by reference in their entirety.

Compounds of the Invention

The invention provides compounds of formula I:

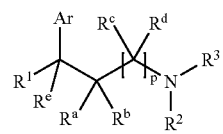

or a pharmaceutically acceptable salt thereof, wherein:
  p is 1 or 2;
  Ar is:
    pyrrolopyridinyl selected from the group consisting of pyrrolopyridin-1-yl, pyrrolopyridin-2-yl, and pyrrolopyridin-3-yl, each of which is optionally substituted;
    pyrrolopyridinyl N-oxide selected from the group consisting of pyrrolopyridin-1-yl N-oxide, pyrrolopyridin-2-yl N-oxide, and pyrrolopyridin-3-yl N-oxide, each of which is optionally substituted; or
    pyrrolopyrimidinyl selected from the group consisting of pyrrolopyrimidin-5-yl, pyrrolopyrimidin-6-yl, and pyrrolopyrimidin-7-yl, each of which is optionally substituted;
  $R^1$ is:
    (a) aryl selected from phenyl and naphthyl, each optionally substituted; or
    (b) heteroaryl selected from indolyl, pyridinyl, thienyl, furanyl, pyrimidinyl, pyridazinyl, pyrazinyl, oxazolyl, thiazolyl, isoxazolyl, isothiazolyl, imidazolyl, pyrazolyl, quinolinyl and isoquinolinyl, each optionally substituted;
    (c) optionally substituted arylalkyl;
    (d) optionally substituted heteroarylalkyl;
    (e) cycloalkyl;

(f) cycloalkylmethyl; or
(g) branched alkyl;

$R^2$ is:
(a) hydrogen;
(b) alkyl;
(c) hydroxyalkyl;
(d) alkoxyalkyl;
(e) benzyl; or or $R^2$ is a bond that connects the nitrogen atom to one of the ring carbon atoms of Ar;

$R^3$ is:
(a) hydrogen;
(b) alkyl;
(c) hydroxyalkyl;
(d) alkoxyalkyl;
(e) benzyl; or
(f) $R^2$ and $R^3$ together with the nitrogen to which they are attached may form an optionally substituted four to seven membered ring that optionally includes an additional heteroatom selected from N, O and S;

$R^a$ is:
hydrogen;
fluoro; or
alkyl;

$R^b$ is:
hydrogen;
alkyl;
hydroxy;
alkoxy;
fluoro; or
hydroxyalkyl;

or one of $R^2$ and $R^3$ together with one of $R^a$ and $R^b$ and the atoms to which they are attached may form a five or six membered ring that optionally includes an additional heteroatom selected from O, N and S;

$R^c$ and $R^d$ each independently is:
hydrogen; or
alkyl;

or $R^c$ and $R^d$ together form =O, =S, or =$NR^f$, wherein $R^f$ is hydrogen, alkyl, or —$OR^g$, wherein $R^g$ is hydrogen or alkyl;

or on of $R^2$ and $R^3$ together with one of $R^c$ and $R^d$ together with the atoms to which they are attached may form a four to six membered ring that optionally includes an additional heteroatom selected from O, N and S; and $R^e$ is hydrogen or alkyl.

It is to be understood that the scope of this invention encompasses not only the various isomers which may exist but also the various mixture of isomers which may be formed. Furthermore, the scope of the present invention also encompasses solvates and salts of compounds of formula I.

In certain embodiments of formula I, p is 1.

In many embodiments of formula I, $R^a$ and $R^b$ are hydrogen.

In certain embodiments, $R^c$ and $R^d$ are hydrogen.

In many embodiments of formula I, $R^e$ is hydrogen.

In certain embodiments of formula I, $R^1$ is optionally substituted aryl, preferably optionally substituted phenyl or optionally substituted naphthyl. Preferably, when $R^1$ is optionally substituted aryl, $R^1$ is optionally substituted phenyl.

In certain embodiments of formula I, $R^1$ is optionally substituted heteroaryl. In such embodiments $R^1$ is preferably optionally substituted pyridinyl. When $R^1$ is optionally substituted pyridinyl, preferably $R^1$ is optionally substituted pyridin-2-yl, optionally substituted pyridin-3-yl or optionally substituted pyridin-4-yl, and more specifically optionally substituted pyridin-2-yl or optionally substituted pyridin-3-yl.

In some embodiments of formula I, $R^1$ is optionally substituted cycloalkyl. Preferably, when $R^1$ is cycloalkyl, $R^1$ is optionally substituted cyclohexyl.

In certain embodiments of formula I, $R^1$ is optionally substituted phenyl.

In certain embodiments of formula I, $R^1$ is optionally substituted pyridinyl.

In certain embodiments of formula I, $R^1$ is optionally substituted cyclohexyl.

In certain embodiments of formula I, $R^1$ is phenyl, pyridin-3-yl, 4-fluorophenyl, or cyclohexyl.

In certain embodiments of formula I, Ar is pyrrolo[2,3-b]pyridinyl selected from pyrrolo[2,3-b]pyridin-1-yl, pyrrolo[2,3-b]pyridin-2-yl, and pyrrolo[2,3-b]pyridin-3-yl, each optionally substituted; pyrrolo[2,3-c]pyridinyl selected from the group consisting of pyrrolo[2,3-c]pyridin-1-yl, pyrrolo[2,3-c]pyridin-2-yl, and pyrrolo[2,3-c]pyridin-3-yl, each optionally substituted; pyrrolo[3,2-b]pyridinyl selected from the group consisting of pyrrolo[3,2-b]pyridin-1-yl, pyrrolo[3,2-b]pyridin-2-yl, and pyrrolo[3,2-b]pyridin-3-yl, each optionally substituted; pyrrolo[3,2-b]pyridinyl 4-oxide selected from the group consisting of pyrrolo[3,2-b]pyridin-1-yl 4-oxide, pyrrolo[3,2-b]pyridin-2-yl 4-oxide, and pyrrolo[3,2-b]pyridin-3-yl 4-oxide, each optionally substituted; pyrrolo[3,2-c]pyridinyl selected from the group consisting of pyrrolo[3,2-c]pyridin-1-yl, pyrrolo[3,2-c]pyridin-2-yl, and pyrrolo[3,2-c]pyridin-3-yl, each optionally substituted; or pyrrolo[2,3-d]pyrimidinyl selected from the group consisting of pyrrolo[2,3-d]pyrimidin-5-yl, pyrrolo[2,3-d]pyrimidin-6-yl, and pyrrolo[2,3-d]pyrimidin-7-yl, each optionally substituted.

In certain embodiments of formula I, Ar is pyrrolo[2,3-b]pyridinyl selected from pyrrolo[2,3-b]pyridin-1-yl, pyrrolo[2,3-b]pyridin-2-yl, and pyrrolo[2,3-b]pyridin-3-yl, each optionally substituted.

In certain embodiments of formula I, Ar is pyrrolo[2,3-c]pyridinyl selected from the group consisting of pyrrolo[2,3-c]pyridin-1-yl, pyrrolo[2,3-c]pyridin-2-yl, and pyrrolo[2,3-c]pyridin-3-yl, each optionally substituted.

In certain embodiments of formula I, Ar is pyrrolo[3,2-b]pyridinyl selected from the group consisting of pyrrolo[3,2-b]pyridin-1-yl, pyrrolo[3,2-b]pyridin-2-yl, and pyrrolo[3,2-b]pyridin-3-yl, each optionally substituted.

In certain embodiments of formula I, Ar is pyrrolo[3,2-b]pyridinyl 4-oxide selected from the group consisting of pyrrolo[3,2-b]pyridin-1-yl 4-oxide, pyrrolo[3,2-b]pyridin-2-yl 4-oxide, and pyrrolo[3,2-b]pyridin-3-yl 4-oxide, each optionally substituted.

In certain embodiments of formula I, Ar is pyrrolo[3,2-c]pyridinyl selected from the group consisting of pyrrolo[3,2-c]pyridin-1-yl, pyrrolo[3,2-c]pyridin-2-yl, and pyrrolo[3,2-c]pyridin-3-yl, each optionally substituted.

In certain embodiments of formula I, Ar is pyrrolo[2,3-d]pyrimidinyl selected from the group consisting of pyrrolo[2,3-d]pyrimidin-5-yl, pyrrolo[2,3-d]pyrimidin-6-yl, and pyrrolo[2,3-d]pyrimidin-7-yl, each optionally substituted.

In certain embodiments of formula I, Ar is pyrrolo[3,2-d]pyrimidinyl selected from the group consisting of pyrrolo[2,3-d]pyrimidin-5-yl, pyrrolo[3,2-d]pyrimidin-6-yl, and pyrrolo[3,2-d]pyrimidin-7-yl, each optionally substituted.

In certain embodiments, Ar is pyrrolo[2,3-d]pyrimidin-7-yl, pyrrolo[2,3-b]pyridin-1-yl, pyrrolo[2,3-b]pyridin-3-yl, pyrrolo[3,2-b]pyridin-1-yl, pyrrolo[3,2-b]pyridin-1-yl 4-oxide, pyrrolo[3,2-c]pyridin-1-yl, pyrrolo[2,3-c]pyridin-1-yl, pyrrolo[3,2-c]pyridin-3-yl, or pyrrolo[2,3-c]pyridin-3-yl, each of which is optionally substituted.

In many embodiments of formula I, one of $R^2$ and $R^3$ is hydrogen and the other is alkyl, preferably methyl.

In certain embodiments of formula I: p is 1; $R^a$, $R^b$, $R^c$, $R^d$ and $R^e$ are hydrogen; Ar is pyrrolopyridinyl or pyrrolopyridinyl N-oxide, each of which is optionally substituted with one, two, three or four substituents each independently selected from alkyl, alkoxy, halo, haloalkyl, haloalkoxy, cyano, alkylsulfonyloxy, —$(CH_2)_q$—$S(O)_rR^f$; —$(CH_2)_q$—$NR^gR^h$; or —$(CH_2)_q$—$C(=O)$—$NR^gR^h$; where q is 0 or 1, r is from 0 to 2, and each of $R^f$, $R^g$, and $R^h$ is independently hydrogen or alkyl; $R^1$ is phenyl, pyridinyl, or cyclohexyl, each of which is optionally substituted with one, two, three or four substituents each of which is independently selected from alkyl, alkoxy, cyano, halo, haloalkyl, haloalkoxy, alkoxyalkyl or hydroxyalkyl; and one of $R^2$ and $R^3$ is hydrogen while the other is alkyl, preferably methyl. In such embodiments Ar may be pyrrolopyridin-1-yl, pyrrolopyridin-2-yl, pyrrolopyridin-3-yl, or N-oxide thereof, each of which is optionally substituted. In such embodiments, Ar is preferably pyrrolopyridin-1-yl, pyrrolopyridin-3-yl, or N-oxide thereof, each of which is optionally substituted, and more preferably Ar is pyrrolo[2,3-b]pyridin-1-yl, pyrrolo[2,3-b]pyridin-3-yl, pyrrolo[3,2-b]pyridin-1-yl, pyrrolo[3,2-b]pyridin-1-yl, 4-oxide, pyrrolo[3,2-c]pyridin-1-yl, pyrrolo[2,3-c]pyridin-1-yl, pyrrolo[3,2-c]pyridin-3-yl, or pyrrolo[2,3-c]pyridin-3-yl, each of which is optionally substituted.

In certain embodiments of formula I: p is 1; $R^a$, $R^b$, $R^c$, $R^d$ and $R^e$ are hydrogen; Ar is pyrrolopyrimidinyl optionally substituted with one, two, three or four substituents each independently selected from alkyl, alkoxy, halo, haloalkyl, haloalkoxy, cyano, alkylsulfonyloxy, —$(CH_2)_q$—$S(O)_rR^f$; —$(CH_2)_q$—$NR^gR^h$; or —$(CH_2)_q$—$C(=O)$—$NR^gR^h$; where q is 0 or 1, r is from 0 to 2, and each of $R^f$, $R^g$, and $R^h$ is independently hydrogen or alkyl; $R^1$ is phenyl, pyridinyl, or cyclohexyl, each of which is optionally substituted with one, two, three or four substituents each of which is independently selected from alkyl, alkoxy, cyano, halo, haloalkyl, haloalkoxy, alkoxyalkyl or hydroxyalkyl; and one of $R^2$ and $R^3$ is hydrogen while the other is alkyl, preferably methyl. In such embodiments Ar may be pyrrolopyrimidin-5-yl, pyrrolopyrimidin-6-yl, or pyrrolopyrimidin-7-yl, each of which is optionally substituted. In such embodiments Ar is preferably pyrrolopyrimidin-5-yl or pyrrolopyrimidin-7-yl, each of which is optionally substituted, and more preferably Ar is optionally substituted pyrrolo[2,3-d]pyrimidin-7-yl.

In certain embodiments of formula I where p is 1 and $R^a$, $R^b$, $R^c$, $R^d$ and $R^e$ are hydrogen, the subject compounds may be represented by formula II:

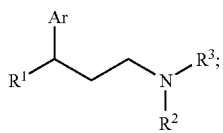

II wherein:
$R^2$ and $R^3$ each independently is hydrogen or alkyl; and
Ar and $R^1$ are as defined herein.

In certain embodiments of formula II, one of $R^2$ and $R^3$ is hydrogen and the other is alkyl, preferably methyl.

In certain embodiments of formula II, $R^1$ is optionally substituted aryl, preferably optionally substituted phenyl or optionally substituted naphthyl.

In certain embodiments of formula II, $R^1$ is optionally substituted heteroaryl. In such embodiments, $R^1$ may be optionally substituted pyridinyl. When $R^1$ is optionally substituted pyridinyl, preferably $R^1$ is optionally substituted pyridin-2-yl, optionally substituted pyridin-3-yl or optionally substituted pyridin-4-yl, and more specifically optionally substituted pyridin-2-yl or optionally substituted pyridin-3-yl.

In certain embodiments of formula II, $R^1$ is optionally substituted cycloalkyl. In such embodiments, $R^1$ is optionally substituted cyclohexyl.

In certain embodiments of formula II, $R^1$ is optionally substituted phenyl, optionally substituted pyridinyl, or optionally substituted cyclohexyl.

In certain embodiments of formula II, $R^1$ is optionally substituted phenyl.

In certain embodiments of formula II, $R^1$ is optionally substituted pyridinyl.

In certain embodiments of formula II, $R^1$ is optionally substituted cyclohexyl.

In certain embodiments of formula II, $R^1$ is phenyl, pyridin-3-yl, 4-fluorophenyl, or cyclohexyl.

In certain embodiments of formula II, Ar is pyrrolo[2,3-b]pyridinyl selected from pyrrolo[2,3-b]pyridin-1-yl, pyrrolo[2,3-b]pyridin-2-yl, and pyrrolo[2,3-b]pyridin-3-yl, each optionally substituted; pyrrolo[2,3-c]pyridinyl selected from the group consisting of pyrrolo[2,3-c]pyridin-1-yl, pyrrolo[2,3-c]pyridin-2-yl, and pyrrolo[2,3-c]pyridin-3-yl, each optionally substituted; pyrrolo[3,2-b]pyridinyl selected from the group consisting of pyrrolo[3,2-b]pyridin-1-yl, pyrrolo[3,2-b]pyridin-2-yl, and pyrrolo[3,2-b]pyridin-3-yl, each optionally substituted; pyrrolo[3,2-b]pyridinyl 4-oxide selected from the group consisting of pyrrolo[3,2-b]pyridin-1-yl 4-oxide, pyrrolo[3,2-b]pyridin-2-yl 4-oxide, and pyrrolo[3,2-b]pyridin-3-yl 4-oxide, each optionally substituted; pyrrolo[3,2-c]pyridinyl selected from the group consisting of pyrrolo[3,2-c]pyridin-1-yl, pyrrolo[3,2-c]pyridin-2-yl, and pyrrolo[3,2-c]pyridin-3-yl, each optionally substituted; or pyrrolo[2,3-d]pyrimidinyl selected from the group consisting of pyrrolo[2,3-d]pyrimidin-5-yl, pyrrolo[2,3-d]pyrimidin-6-yl, and pyrrolo[2,3-d]pyrimidin-7-yl, each optionally substituted.

In certain embodiments of formula II, Ar is pyrrolo[2,3-b]pyridinyl selected from pyrrolo[2,3-b]pyridin-1-yl, pyrrolo[2,3-b]pyridin-2-yl, and pyrrolo[2,3-b]pyridin-3-yl, each optionally substituted.

In certain embodiments of formula II, Ar is pyrrolo[2,3-c]pyridinyl selected from the group consisting of pyrrolo[2,3-c]pyridin-1-yl, pyrrolo[2,3-c]pyridin-2-yl, and pyrrolo[2,3-c]pyridin-3-yl, each optionally substituted.

In certain embodiments of formula II, Ar is pyrrolo[3,2-b]pyridinyl selected from the group consisting of pyrrolo[3,2-b]pyridin-1-yl, pyrrolo[3,2-b]pyridin-2-yl, and pyrrolo[3,2-b]pyridin-3-yl, each optionally substituted.

In certain embodiments of formula II, Ar is pyrrolo[3,2-b]pyridinyl 4-oxide selected from the group consisting of pyrrolo[3,2-b]pyridin-1-yl 4-oxide, pyrrolo[3,2-b]pyridin-2-yl 4-oxide, and pyrrolo[3,2-b]pyridin-3-yl 4-oxide, each optionally substituted.

In certain embodiments of formula II, Ar is pyrrolo[3,2-c]pyridinyl selected from the group consisting of pyrrolo[3,2-c]pyridin-1-yl, pyrrolo[3,2-c]pyridin-2-yl, and pyrrolo[3,2-c]pyridin-3-yl, each optionally substituted.

In certain embodiments of formula II, Ar is pyrrolo[2,3-d]pyrimidinyl selected from the group consisting of pyrrolo[2,3-d]pyrimidin-5-yl, pyrrolo[2,3-d]pyrimidin-6-yl, and pyrrolo[2,3-d]pyrimidin-7-yl, each optionally substituted.

In certain embodiments of formula II, Ar is pyrrolo[3,2-d]pyrimidinyl selected from the group consisting of pyrrolo[2,3-d]pyrimidin-5-yl, pyrrolo[3,2-d]pyrimidin-6-yl, and pyrrolo[3,2-d]pyrimidin-7-yl, each optionally substituted.

In certain embodiments of formula II, Ar is pyrrolo[2,3-d]pyrimidin-7-yl, pyrrolo[2,3-b]pyridin-1-yl, pyrrolo[2,3-b]pyridin-3-yl, pyrrolo[3,2-b]pyridin-1-yl, pyrrolo[3,2-b]pyridin-1-yl 4-oxide, pyrrolo[3,2-c]pyridin-1-yl, pyrrolo[2,3-c]pyridin-1-yl, pyrrolo[3,2-c]pyridin-3-yl, or pyrrolo[2,3-c]pyridin-3-yl, each of which is optionally substituted.

In certain embodiments of formula II: Ar is pyrrolopyridinyl or pyrrolopyridinyl N-oxide, each of which is optionally substituted with one, two, three or four substituents each independently selected from alkyl, alkoxy, halo, haloalkyl, haloalkoxy, cyano, alkylsulfonyloxy, —(CH$_2$)$_q$—S(O)$_r$R$^f$; —(CH$_2$)$_q$—NR$^g$R$^h$; or —(CH$_2$)$_q$—C(=O)—NR$^g$R$^h$; where q is 0 or 1, r is from 0 to 2, and each of R$^f$, R$^g$, and R$^h$ is independently hydrogen or alkyl; R$^1$ is phenyl, pyridinyl, or cyclohexyl, each of which is optionally substituted with one, two, three or four substituents each of which is independently selected from alkyl, alkoxy, cyano, halo, haloalkyl, haloalkoxy, alkoxyalkyl or hydroxyalkyl; and one of R$^2$ and R$^3$ is hydrogen while the other is alkyl, preferably methyl. In such embodiments Ar may be pyrrolopyridin-1-yl, pyrrolopyridin-2-yl, pyrrolopyridin-3-yl, or N-oxide thereof, each of which is optionally substituted. In such embodiments, Ar is preferably pyrrolopyridin-1-yl, pyrrolopyridin-3-yl, or N-oxide thereof, each of which is optionally substituted, and more preferably Ar is pyrrolo[2,3-b]pyridin-1-yl, pyrrolo[2,3-b]pyridin-3-yl, pyrrolo[3,2-b]pyridin-1-yl, pyrrolo[3,2-b]pyridin-1-yl 4-oxide, pyrrolo[3,2-c]pyridin-1-yl, pyrrolo[2,3-c]pyridin-1-yl, pyrrolo[3,2-c]pyridin-3-yl, or pyrrolo[2,3-c]pyridin-3-yl, each of which is optionally substituted.

In certain embodiments of formula II: Ar is pyrrolopyrimidinyl optionally substituted with one, two, three or four substituents each independently selected from alkyl, alkoxy, halo, haloalkyl, haloalkoxy, cyano, alkylsulfonyloxy, —(CH$_2$)$_q$—S(O)$_r$R$^f$; —(CH$_2$)$_q$—NR$^g$R$^h$; or —(CH$_2$)$_q$—C(=O)—NR$^g$R$^h$; where q is 0 or 1, r is from 0 to 2, and each of R$^f$, R$^g$, and R$^h$ is independently hydrogen or alkyl; R$^1$ is phenyl, pyridinyl, or cyclohexyl, each of which is optionally substituted with one, two, three or four substituents each of which is independently selected from alkyl, alkoxy, cyano, halo, haloalkyl, haloalkoxy, alkoxyalkyl or hydroxyalkyl; and one of R$^2$ and R$^3$ is hydrogen while the other is alkyl, preferably methyl. In such embodiments Ar may be pyrrolopyrimidin-5-yl, pyrrolopyrimidin-6-yl, or pyrrolopyrimidin-7-yl, each of which is optionally substituted. In such embodiments Ar is preferably pyrrolopyrimidin-5-yl or pyrrolopyrimidin-7-yl, each of which is optionally substituted, and more preferably Ar is optionally substituted-pyrrolo[2,3-d]pyrimidin-7-yl.

In compounds of formula II in which Ar is optionally substituted pyrrolo[2,3-b]pyridinyl, the subject compounds may be represented by formula III:

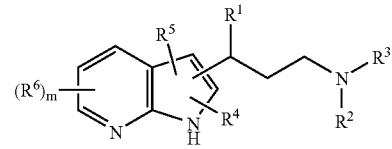

III wherein
m is an integer from 0 to 3;
each of R$^4$ and R$^5$ is independently: hydrogen; alkoxy, cyano, alkyl, halo, —S(O)$_r$R$^f$; and —C(=O)NR$^g$R$^h$; wherein r is an integer from 0 to 2, and each of R$^f$, R$^g$, and R$^h$ is independently hydrogen or alkyl;
each R$^6$ is independently: alkoxy, cyano, alkyl, amino, alkylamino, dialkylamino, halo, —S(O)$_r$R$^f$; and —C(=O)NR$^g$R$^h$; wherein r is an integer from 0 to 2, and each of R$^f$, R$^g$, and R$^h$ is independently hydrogen or alkyl; and
R$^1$, R$^2$ and R$^3$ are as defined herein.

In embodiments of formula II wherein Ar is optionally substituted pyrrolo[2,3-b]pyridin-1-yl, the compounds of the invention may be more specifically of formula IV:

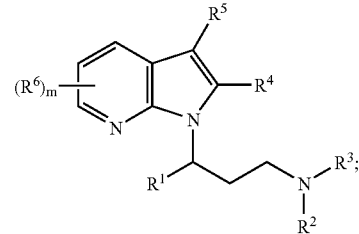

IV wherein m, R$^1$, R$^2$, R$^3$, R$^4$, R$^5$, and R$^6$ are as defined herein.

In certain embodiments of formula IV, the subject compounds may be more specifically of formula IVa or IVb:

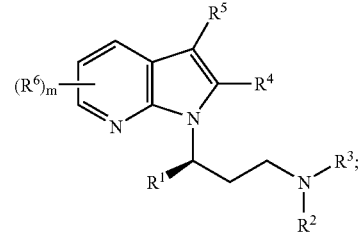

IVa

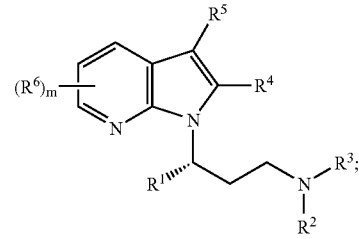

IVb wherein m, R$^1$, R$^2$, R$^3$, R$^4$, R$^5$, and R$^6$ are as defined herein. Preferably such compounds are of formula IVa.

In embodiments of formula II wherein Ar is optionally substituted pyrrolo[2,3-b]pyridin-3-yl, the compounds of the invention may be more specifically of formula V:

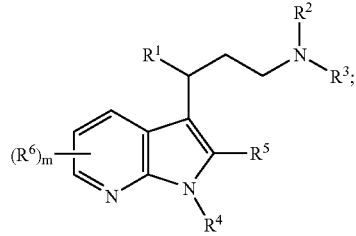

V wherein m, $R^1$, $R^2$, $R^3$, $R^4$, $R^5$, and $R^6$ are as defined herein.

In certain embodiments of formula V, the subject compounds may be more specifically of formula Va or Vb:

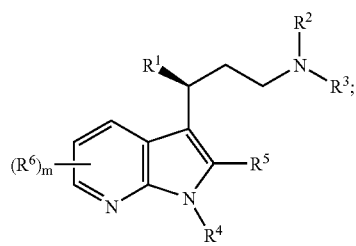

Va

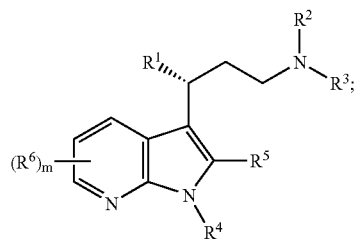

Vb wherein m, $R^1$, $R^2$, $R^3$, $R^4$, $R^5$, and $R^6$ are as defined herein. Preferably such compounds are of formula Vb.

In embodiments of formula II wherein Ar is optionally substituted pyrrolo[2,3-c]pyridinyl, the compounds of the invention may be more specifically of formula VI:

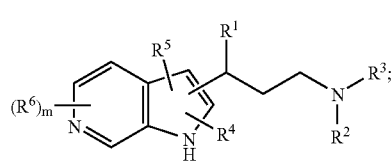

VI wherein m, $R^1$, $R^2$, $R^3$, $R^4$, $R^5$, and $R^6$ are as defined herein.

In embodiments of formula II wherein Ar is optionally substituted pyrrolo[2,3-c]pyridin-1-yl, the compounds of the invention may be more specifically of formula VII:

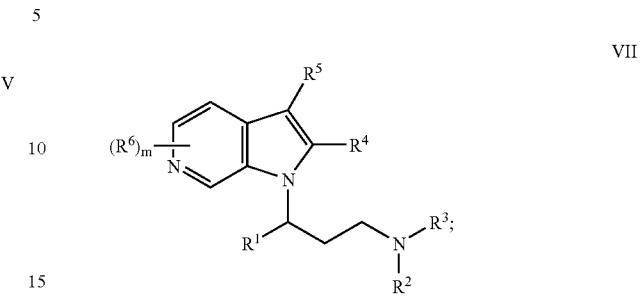

VII wherein m, $R^1$, $R^2$, $R^3$, $R^4$, $R^5$, and $R^6$ are as defined herein.

In certain embodiments of formula VII, the subject compounds may be more specifically of formula VIIa or VIIb:

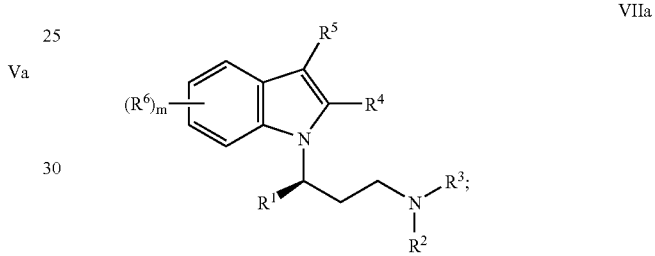

VIIa

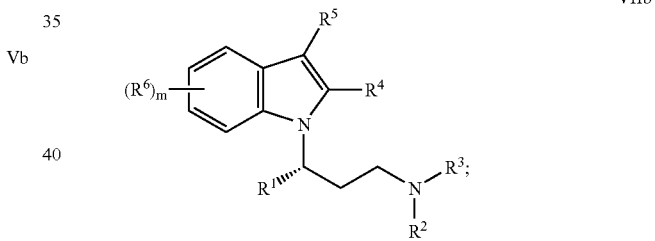

VIIb wherein m, $R^1$, $R^2$, $R^3$, $R^4$, $R^5$, and $R^6$ are as defined herein. Preferably such compounds are of formula VIIa.

In embodiments of formula II wherein Ar is optionally substituted pyrrolo[3,2-c]pyridinyl, the compounds of the invention may be more specifically of formula VIII:

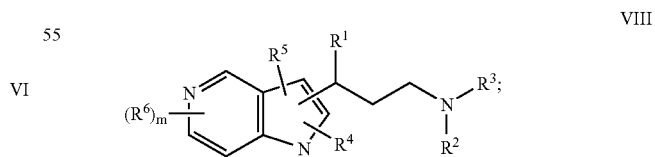

VIII wherein m, $R^1$, $R^2$, $R^3$, $R^4$, $R^5$, and $R^6$ are as defined herein.

In embodiments of formula II wherein Ar is optionally substituted pyrrolo[3,2-c]pyridin-1-yl, the compounds of the invention may be more specifically of formula IX:

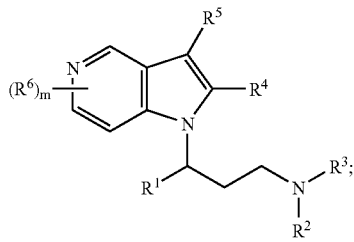

IX wherein m, $R^1$, $R^2$, $R^3$, $R^4$, $R^5$, and $R^6$ are as defined herein.

In certain embodiments of formula IX, the subject compounds may be more specifically of formula IXa or IXb:

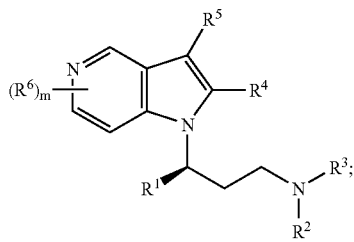

IXa

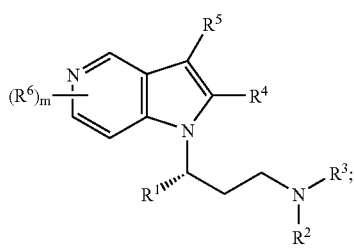

IXb wherein m, $R^1$, $R^2$, $R^3$, $R^4$, $R^5$, and $R^6$ are as defined herein. Preferably such compounds are of formula IXa.

In embodiments of formula II wherein Ar is optionally substituted pyrrolo[3,2-b]pyridinyl, the compounds of the invention may be more specifically of formula X:

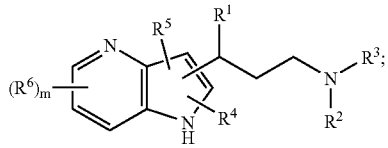

X wherein m, $R^1$, $R^2$, $R^3$, $R^4$, $R^5$, and $R^6$ are as defined herein.

In embodiments of formula II wherein Ar is optionally substituted pyrrolo[3,2-b]pyridin-1-yl, the compounds of the invention may be more specifically of formula IX:

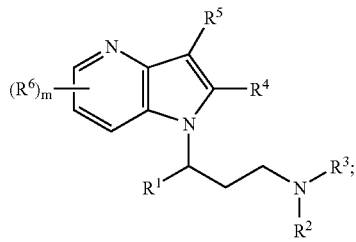

XI wherein m, $R^1$, $R^2$, $R^3$, $R^4$, $R^5$, and $R^6$ are as defined herein.

In certain embodiments of formula XI, the subject compounds may be more specifically of formula XIa or XIb:

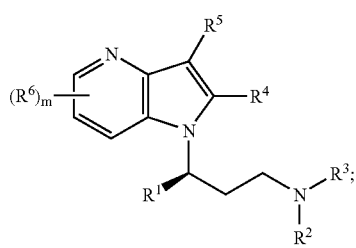

XIa

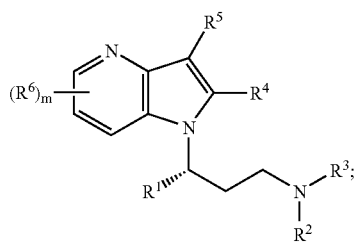

XIb wherein m, $R^1$, $R^2$, $R^3$, $R^4$, $R^5$, and $R^6$ are as defined herein. Preferably such compounds are of formula XIa.

In embodiments of formula II wherein Ar is optionally substituted pyrrolo[3,2-b]pyridinyl and $R^2$ is a bond that connects the nitrogen atom to one of the ring carbon atoms of Ar, the compounds of the invention may be more specifically of formula XII:

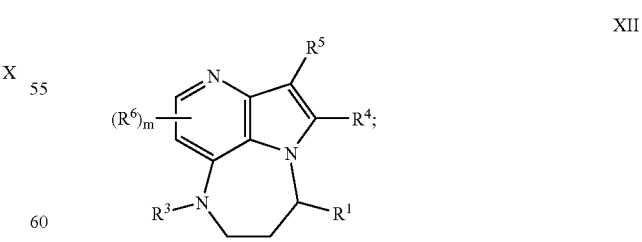

XII wherein m, $R^1$, $R^3$, $R^4$, $R^5$, and $R^6$ are as defined herein.

In embodiments of formula II wherein Ar is optionally substituted pyrrolo[2,3-d]pyrimidinyl, the compounds of the invention may be more specifically of formula X:

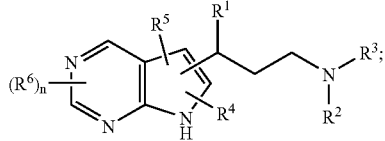

wherein n is an integer from 0 to 2, and $R^1$, $R^2$, $R^3$, $R^4$, $R^5$ and $R^6$ are as defined herein.

In embodiments of formula II wherein Ar is optionally substituted pyrrolo[2,3-d]pyrimidin-7-yl, the compounds of the invention may be more specifically of formula XIV:

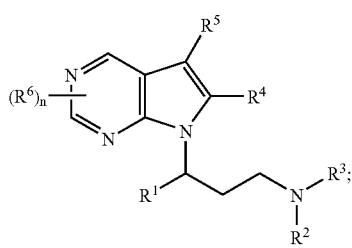

wherein n, $R^1$, $R^2$, $R^3$, $R^4$, $R^5$, and $R^6$ are as defined herein.

In certain embodiments of formula XIV, the subject compounds may be more specifically of formula XIVa or XIVb:

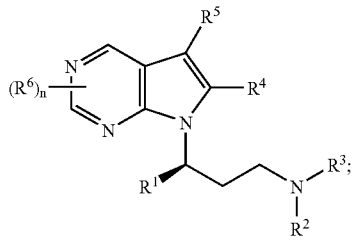

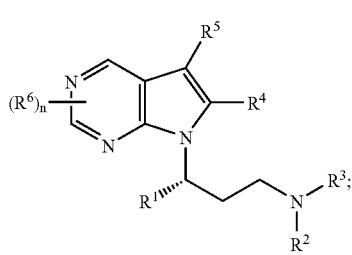

wherein n, $R^1$, $R^2$, $R^3$, $R^4$, $R^5$, and $R^6$ are as defined herein. Preferably such compounds are of formula XIVa.

In embodiments of formula II wherein Ar is optionally substituted pyrrolo[3,2-b]pyridinyl N-oxide, the compounds of the invention may be more specifically of formula XV:

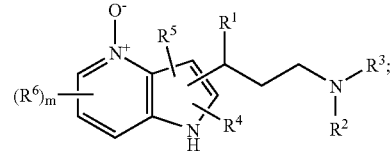

wherein m, $R^1$, $R^2$, $R^3$, $R^4$, $R^5$ and $R^6$ are as defined herein.

In embodiments of formula II wherein Ar is optionally substituted pyrrolo[3,2-b]pyridin-1-yl N-oxide, the compounds of the invention may be more specifically of formula XVI:

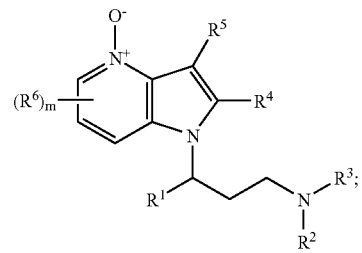

wherein m, $R^1$, $R^2$, $R^3$, $R^4$, $R^5$, and $R^6$ are as defined herein.

In certain embodiments of formula XVI, the subject compounds may be more specifically of formuula XVIa or XVIb:

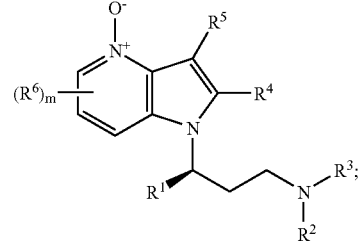

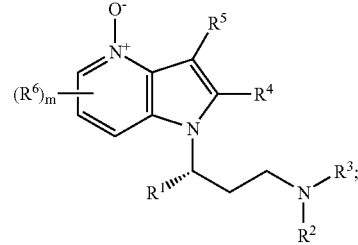

wherein m, $R^1$, $R^2$, $R^3$, $R^4$, $R^5$, and $R^6$ are as defined herein. Preferably such compounds are of formula XVIa.

In certain embodiments of any of formulas III-XVIb, one of $R^2$ and $R^3$ is hydrogen and the other is alkyl, preferably methyl.

In certain embodiments of any of formulas III-XVIb, $R^1$ is optionally substituted aryl, preferably optionally substituted phenyl.

In certain embodiments of any of formulas III-XVIb, $R^1$ is optionally substituted heteroaryl. In such embodiments $R^1$ is preferably optionally substituted pyridinyl. When $R^1$ is optionally substituted pyridinyl, preferably $R^1$ is optionally substituted pyridin-2-yl, optionally substituted pyridin-3-yl or optionally substituted pyridin-4-yl, and more specifically optionally substituted pyridin-2-yl or optionally substituted pyridin-3-yl.

In certain embodiments of any of formulas III-XVIb, $R^1$ is optionally substituted cycloalkyl, preferably optionally substituted cyclohexyl.

In certain embodiments of any of formulas III-XVIb, $R^1$ is phenyl, pyridinyl, or cyclohexyl, each of which is optionally substituted.

In certain embodiments of any of formulas III-XVIb, $R^1$ is optionally substituted phenyl.

In certain embodiments of any of formulas III-XVIb, $R^1$ is optionally substituted pyridinyl.

In certain embodiments of any of formulas III-XVIb, $R^1$ is phenyl, pyridin-3-yl, 4-fluorophenyl, or cyclohexyl.

In certain embodiments of formula III-XVIb, $R^4$ is hydrogen.

In certain embodiments of formula III-XVIb, $R^5$ is hydrogen.

In certain embodiments of any of formulas III-XVIb, each $R^6$ is independently halo, amino, alkylamino, dialkylamino, alkyl, cyano, or alkoxy. In these cases, $R^6$ is preferably, fluoro, chloro, bromo, methoxy, cyano, isopropoxy, methylamino. More preferably, $R^6$ is chloro, methoxy, isopropoxy, or methylamino.

In certain embodiments of any of formulas III-XVIb, m is 0 or 1, and $R^6$ is chloro, methoxy, isopropoxy, or methylamino.

In certain embodiments of any of formulas III-XVIb, m is 0 or 1, and $R^6$ is halo, alkyl, alkoxy or alkylamino.

In certain embodiments of any of formulas III-XVIb, m is 0.

In certain embodiments of any of formulas III-IXb, m is 1, and $R^6$ is halo, alkoxy and is located at the 4-position.

In certain embodiments of any of formulas X, XI, XIa, and XIb, m is 1, and $R^6$ is alkoxy and is located at the 5-or 7-position.

In certain embodiments of any of formulas XIII, XIV, XIVa, and XIVb, m is 1, and $R^6$ is alkylamino and is located at the 4-position.

In certain embodiments of formulas III-XVIb, $R^4$ and $R^5$ are hydrogen.

In certain embodiments of any of formulas III-XVIb, one of $R^4$ and $R^5$ is hydrogen and the other is alkyl, cyano, halo or alkoxy.

In certain embodiments of any of formulas III-XVIb, m is 0 or 1, $R^1$ is optionally substituted phenyl, and one of $R^2$ and $R^3$ is hydrogen and the other is alkyl, preferably methyl.

In certain embodiments of any of formulas III-XVIb, m is 0 or 1, $R^1$ is optionally substituted phenyl, one of $R^2$ and $R^3$ is hydrogen and the other is alkyl, preferably methyl, and $R^4$ and $R^5$ are hydrogen.

In certain embodiments of any of formulas III-XVIb, m is 0 or 1, $R^1$ is optionally substituted phenyl, one of $R^2$ and $R^3$ is hydrogen and the other is alkyl, preferably methyl, $R^4$ and $R^5$ are hydrogen, and each $R^6$ is independently halo, cyano, alkylamino, or alkoxy. In such embodiments optionally substituted phenyl may be phenyl optionally substituted one, two, three or four times with alkyl, alkoxy, cyano, halo, haloalkyl, haloalkoxy, alkoxyalkyl or hydroxyalkyl.

In certain embodiments of any of formulas III-XVIb, m is 0 or 1, $R^1$ is optionally substituted pyridinyl, and one of $R^2$ and $R^3$ is hydrogen and the other is alkyl, preferably methyl. In such embodiments optionally substituted pyridinyl may be pyridinyl optionally substituted one, two or three times with alkyl, alkoxy, cyano, halo, haloalkyl, haloalkoxy, alkoxyalkyl or hydroxyalkyl. In such embodiments $R^1$ is preferably pyridin-3-yl or pyridin-2-yl.

In certain embodiments of formulas any of III-XVIb, m is 0 or 1, $R^1$ is optionally ted cyclohexyl, one of $R^2$ and $R^3$ is hydrogen and the other is alkyl, preferably methyl, and $R^4$ and $R^5$ are hydrogen. In such embodiments optionally substituted cyclohexyl may be cyclohexyl optionally substituted one, two or three times with alkyl, alkoxy, cyano, halo, haloalkyl, haloalkoxy, alkoxyalkyl or hydroxyalkyl.

Representative compounds in accordance with the methods of the invention are shown in Table 1.

TABLE 1

| # | Structure | Name (Sysname) | Mp (° C.) or [M + H] |
|---|---|---|---|
| 1 | 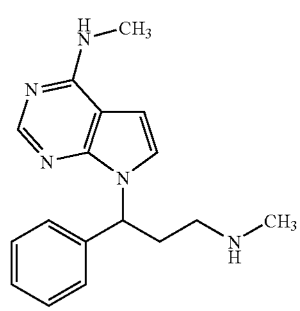 | Methyl-[7-(3-methylamino-1-phenyl-propyl)-7H-pyrrolo[2,3-d]pyrimidin-4-yl]-amine | 296 |

TABLE 1-continued

| # | Structure | Name (Sysname) | Mp (° C.) or [M + H] |
|---|---|---|---|
| 2 | 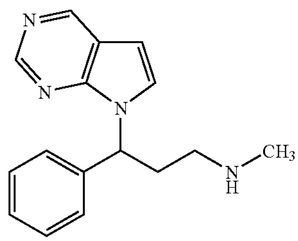 | Methyl-(3-phenyl-3-pyrrolo[2,3-d]pyrimidin-7-yl-propyl)-amine | 267 |
| 3 | 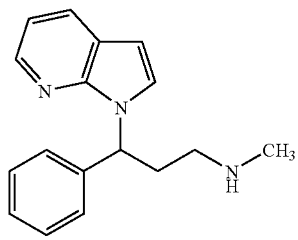 | Methyl-(3-phenyl-3-pyrrolo[2,3-b]pyridin-1-yl-propyl)-amine e | 266 |
| 4 | 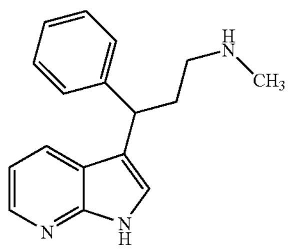 | Methyl-[3-phenyl-3-(1H-pyrrolo[2,3-b]pyridin-3-yl)-propyl]-amine | 266 |
| 5 | 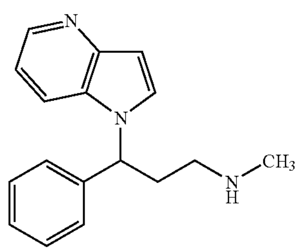 | Methyl-(3-phenyl-3-pyrrolo[3,2-b]pyridin-1-yl-propyl)-amine | 93.9-95.5 |
| 6 | 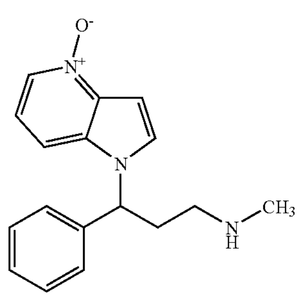 | Methyl-[3-(4-oxy-pyrrolo[3,2-b]pyridin-1-yl)-3-phenyl-propyl]-amine | 282 |
| 7 | 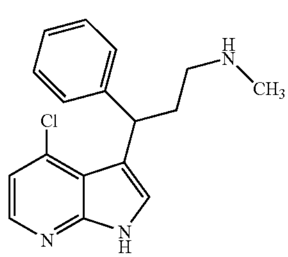 | [3-(4-Chloro-1H-pyrrolo[2,3-b]pyridin-3-yl)-3-phenyl-propyl]-methyl-amine | 300 |

TABLE 1-continued

| # | Structure | Name (Sysname) | Mp (° C.) or [M + H] |
|---|---|---|---|
| 8 | 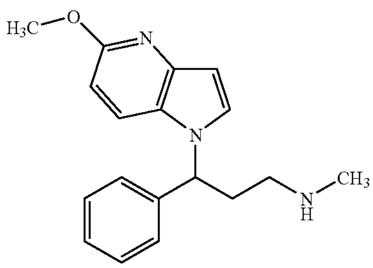 | [3-(5-Methoxy-pyrrolo[3,2-b]pyridin-1-yl)-3-phenyl-propyl]-methyl-amine | 296 |
| 9 | 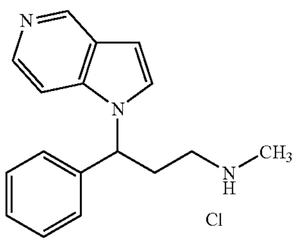 | Methyl-(3-phenyl-3-pyrrolo[3,2-c]pyridin-1-yl-propyl)-amine | 266 |
| 10 | 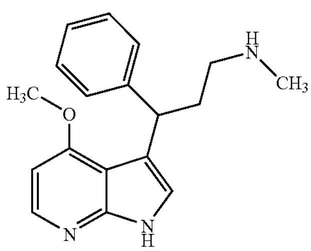 | [3-(4-Methoxy-1H-pyrrolo[2,3-b]pyridin-3-yl)-3-phenyl-propyl]-methyl-amine | 158.7-159.4 |
| 11 | 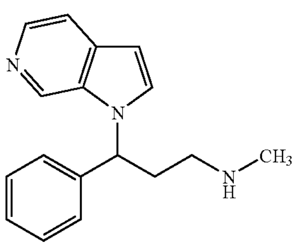 | Methyl-(3-phenyl-3-pyrrolo[2,3-c]pyridin-1-yl-propyl)-amine | 266 |
| 12 | 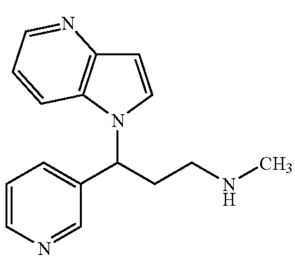 | Methyl-(3-pyridin-3-yl-3-pyrrolo[3,2-b]pyridin-1-yl-propyl)-amine | 267 |
| 13 | 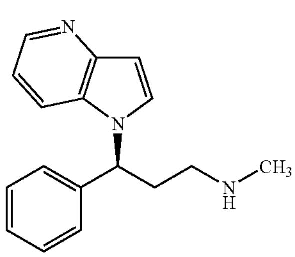 | Methyl-((S)-3-phenyl-3-pyrrolo[3,2-b]pyridin-1-yl-propyl)-amine | 160-162 (HCl Salt) |

TABLE 1-continued

| # | Structure | Name (Sysname) | Mp (° C.) or [M + H] |
|---|---|---|---|
| 14 | 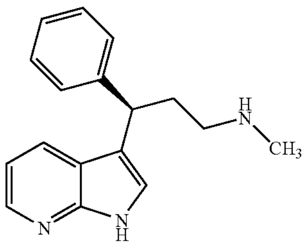 | Methyl-[(R)-3-phenyl-3-(1H-pyrrolo[2,3-b]pyridin-3-yl)-propyl]-amine | 266 |
| 15 | 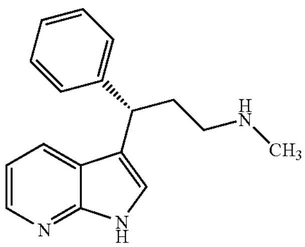 | Methyl-[(S)-3-phenyl-3-(1H-pyrrolo[2,3-b]pyridin-3-yl)-propyl]-amine | 266 |
| 16 | 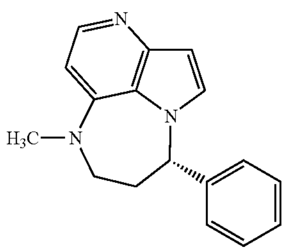 | S)-6-Methyl-9-phenyl-6,7,8,9-tetrahydro-3,6,9a-triaza-benzo[cd]azulene | 264 |
| 17 | 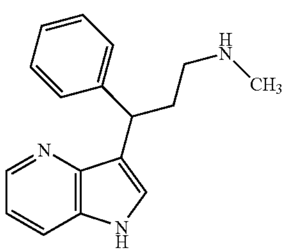 | Methyl-[3-phenyl-3-(1H-pyrrolo[3,2-b]pyridin-3-yl)-propyl]-amine | 266 |
| 18 | 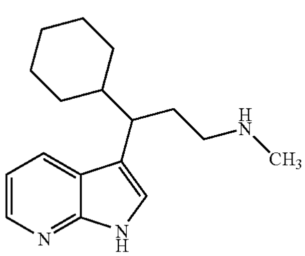 | [3-Cyclohexyl-3-(1H-pyrrolo[2,3-b]pyridin-3-yl)-propyl]-methyl-amine | 272 |
| 19 | 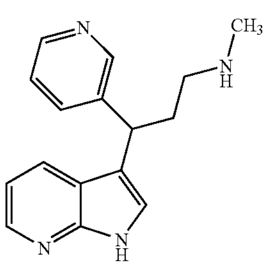 | Methyl-[3-pyridin-3-yl-3-(1H-pyrrolo[2,3-b]pyridin-3-yl)-propyl]-amine | 267 |

TABLE 1-continued

| # | Structure | Name (Sysname) | Mp (° C.) or [M + H] |
|---|---|---|---|
| 20 | 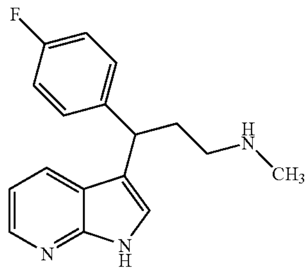 | [3-(4-Fluoro-phenyl)-3-(1H-pyrrolo[2,3-b]pyridin-3-yl)-propyl]-methyl-amine | 284 |
| 21 | 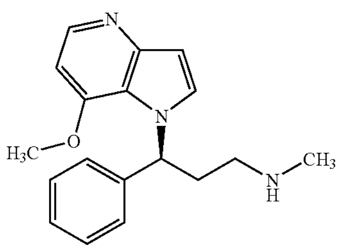 | [(S)-3-(7-Methoxy-pyrrolo[3,2-b]pyridin-1-yl)-3-phenyl-propyl]-methyl-amine | 296 |
| 22 | 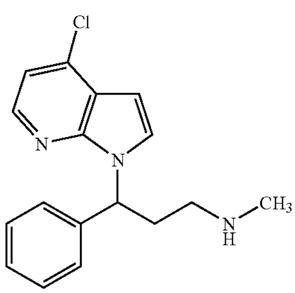 | [3-(4-Chloro-pyrrolo[2,3-b]pyridin-1-yl)-3-phenyl-propyl]-methyl-amine | 300 |
| 23 | 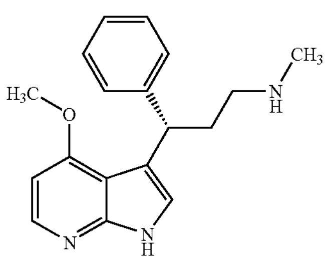 | [(S)-3-(4-Methoxy-1H-pyrrolo[2,3-b]pyridin-3-yl)-3-phenyl-propyl]-methyl-amine | 71.1-72.7 (TFA Salt) |
| 24 | 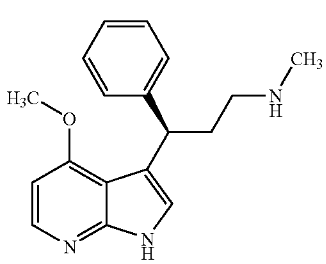 | [(R)-3-(4-Methoxy-1H-pyrrolo[2,3-b]pyridin-3-yl)-3-phenyl-propyl]-methyl-amine | 68.5-70.3 (TFA Salt) |

TABLE 1-continued

| # | Structure | Name (Sysname) | Mp (° C.) or [M + H] |
|---|---|---|---|
| 25 | 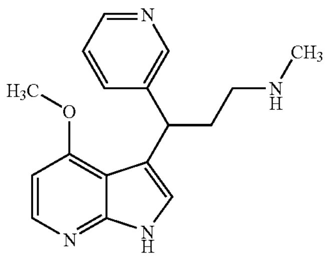 | [3-(4-Methoxy-1H-pyrrolo[2,3-b]pyridin-3-yl)-3-pyridin-3-yl-propyl]-methyl-amine | 297 |
| 26 | 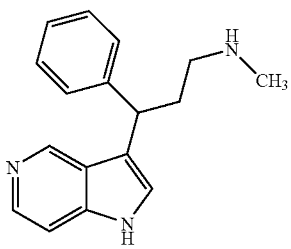 | Methyl-[3-phenyl-3-(1H-pyrrolo[3,2-c]pyridin-3-yl)-propyl]-amine | 266 |
| 27 | 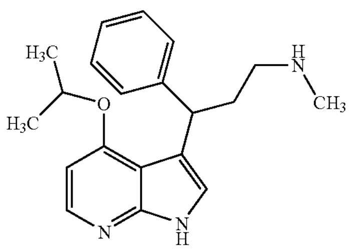 | 3-(4-Isopropoxy-1H-pyrrolo[2,3-b]pyridin-3-yl)-3-phenyl-propyl]-methyl-amine | 124.0-126.5 (HCl Salt) |
| 28 | 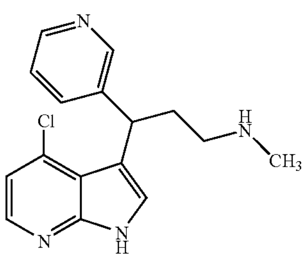 | [3-(4-Chloro-1H-pyrrolo[2,3-b]pyridin-3-yl)-3-pyridin-3-yl-propyl]-methyl-amine | 301 |
| 29 | 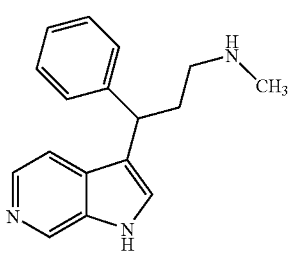 | Methyl-[3-phenyl-3-(1H-pyrrolo[2,3-c]pyridin-3-yl)-propyl]-amine | 266 |
| 30 | 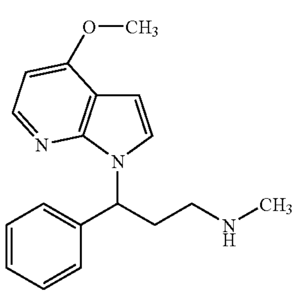 | [3-(4-Methoxy-pyrrolo[2,3-b]pyridin-1-yl)-3-phenyl-propyl]-methyl-amine | 296 |

TABLE 1-continued

| # | Structure | Name (Sysname) | Mp (° C.) or [M + H] |
|---|---|---|---|
| 31 | 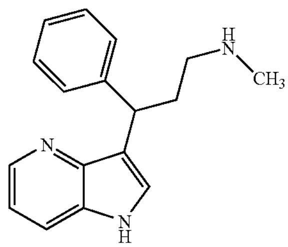 | Methyl-[3-phenyl-3-(1H-pyrrolo[3,2-b]pyridin-3-yl)-propyl]-amine | 266 |
| 32 | 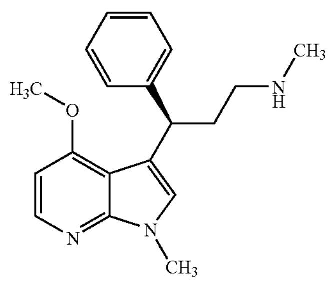 | [3-(R)-(4-Methoxy-1-methyl-1H-pyrrolo[2,3-b]pyridin-3-yl)-3-phenyl-propyl]-methyl-amine | 175.7-178.0 (HCl Salt) |
| 33 | 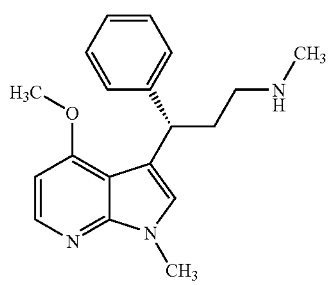 | [3-(S)-(4-Methoxy-1-methyl-1H-pyrrolo[2,3-b]pyridin-3-yl)-3-phenyl-propyl]-methyl-amine | 165.0-167.5 (HCl Salt) |
| 34 | 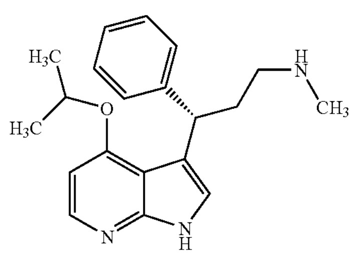 | 3-(S)-(4-Isopropoxy-1H-pyrrolo[2,3-b]pyridin-3-yl)-3-phenyl-propyl]-methyl-amine | 162.3-163.9 |
| 35 | 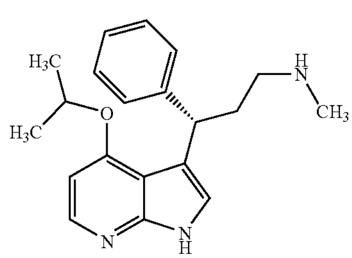 | 3-(R)-(4-Isopropoxy-1H-pyrrolo[2,3-b]pyridin-3-yl)-3-phenyl-propyl]-methyl-amine | 160.0-161.4 |

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare compounds of the invention where one of $X^1$, $X^2$, $X^3$ or $X^4$ is N and the others are CH, and wherein m, $R^1$, $R^2$, $R^3$, $R^4$, $R^5$ and $R^6$ are as defined herein.

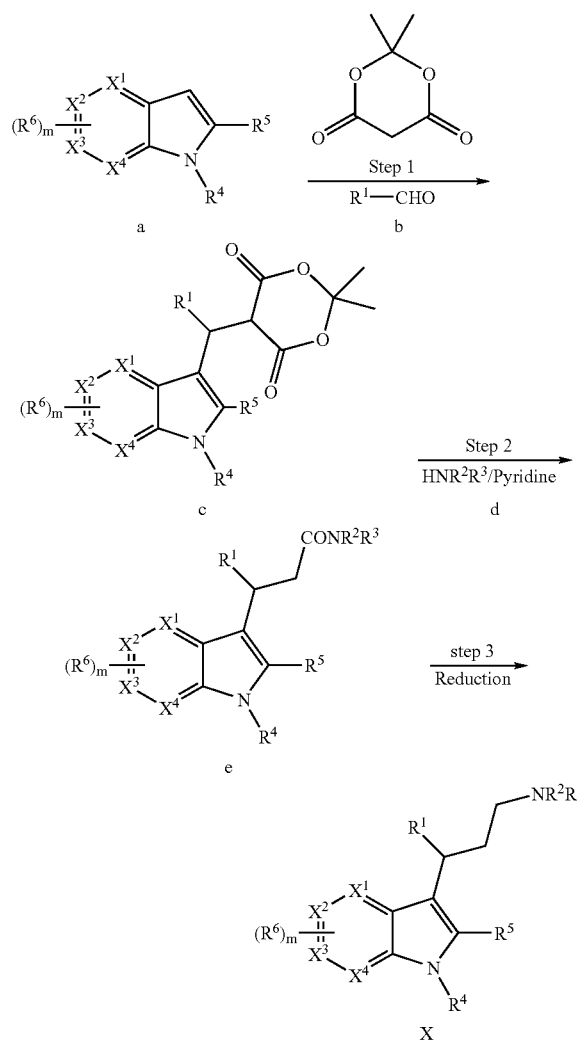

In Step 1 of Scheme A, azaindole a is treated with 2,2-dimethyl-[1,3]dioxane-4,6-dione and an aldehyde b, using the procedure of Tetrahedron 56 (2000) 5479-5492, to provide dione compound c. Aldehyde b may comprise, for example, an aryl aldehyde such as benzaldehyde or naphthaldehyde, a heteroaryl aldehyde such as a pyridine carbaldehyde, thiophene carbaldehyde, furan carbaldehyde, a cycloalkyl carbaldehyde such as cyclohexanecarbaldehyde, a branched $C_4$-$C_7$-alkyl carbaldehyde, or the like, each of which may be optionally substituted as defined herein. Numerous substituted aryl, heteroaryl, and cycloalkyl aldehydes b are commercially available or are readily prepared by techniques well known to those skilled in the art.

In step 2, the dione compound c is reacted with an amine d in the presence of pyridine or other catalytic amine to afford an indole propionamide compound e. Amine d may comprise, for example, a monoalkyl amine, a dialkyl amine, or a cyclic amine. Exemplary amines of this sort include ammonia, methylamine, ethylamine, isopropylamine, aniline, benzylamine, phenylethylamine, cyclopropylamine, dimethylamine, aziridine, pyrrlolidine, piperidine and piperazine.

Reduction of propionamide compound e in step 3 provides a 3-aminopropyl indole compound of formula X in accordance with the invention. This reduction may be achieved using lithium aluminum hydride, borane or borane complex, or other strong reducing agent.

Scheme B below illustrates another synthetic procedure usable to prepare specific compounds of the invention, wherein one of $X^1$, $X^2$, $X^3$ or $X^4$ is N and the others are CH, and m, $R^1$, $R^2$, $R^3$, $R^4$, $R^5$ and $R^6$ are as defined herein.

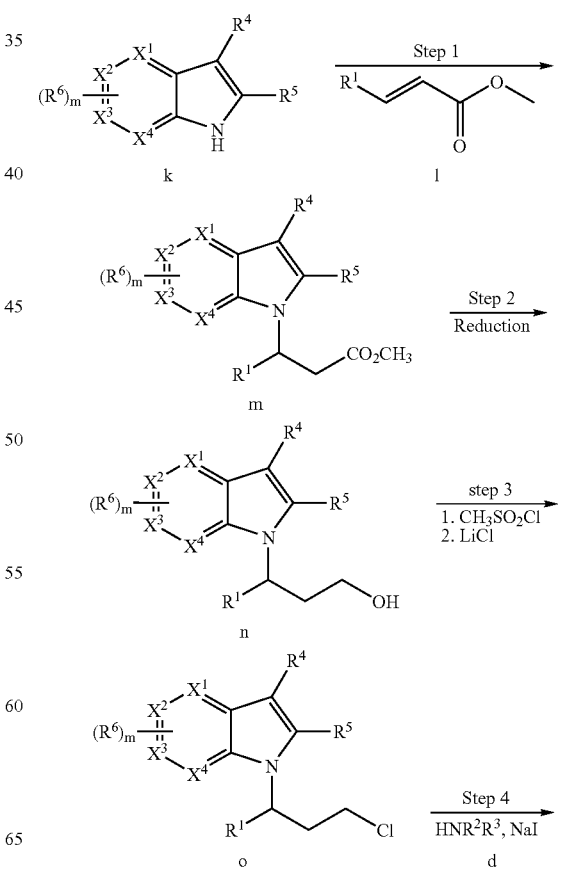

-continued

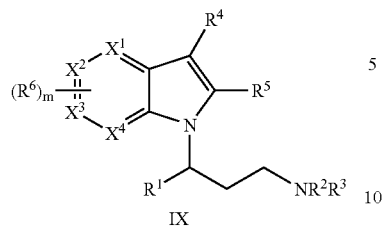

IX

In step 1 of Scheme B, azaindole k is reacted with an acrylic ester 1 to afford an pyrrolopyrindine propionic ester m. Numerous aryl, heteroaryl, cycloalkyl and branched $C_4$-$C_7$ alkyl-substituted acrylic esters 1, such as various cinnamates, are commercially available or are readily prepared by techniques well known to those skilled in the art and may be used in this step.

In step 2, the propionic ester m is subject to reducing conditions to provide azaindole propanol n. This reduction may be carried out using lithium aluminum hydride or other strong reducing agent.

The azaindole propanol n is treated with methane sulfonyl chloride in step 3, followed by lithium chloride, to provide pyrrolopyrindine propyl chloride o. Thionyl chloride, acyl chloride, or other chloride source may alternatively be used in this step. Alternatively, treatment of n with methane sulfonlyl chloride provides the corresponding mesylate compound (not shown).

In step 4, azaindole propyl chloride is reacted with amine d to yield a 3-aminopropyl azaindole compound of formula IX in accordance with the invention. Various amines may be used in this step as noted above in regard to Scheme A.

In Scheme C another synthetic route to the compounds of the invention is illustrated, wherein one of $X^1$, $X^2$, $X^3$ or $X^4$ is N and the others are CH, and m, $R^1$, $R^2$, $R^3$, $R^4$, $R^5$ and $R^6$ are as defined herein.

SCHEME C

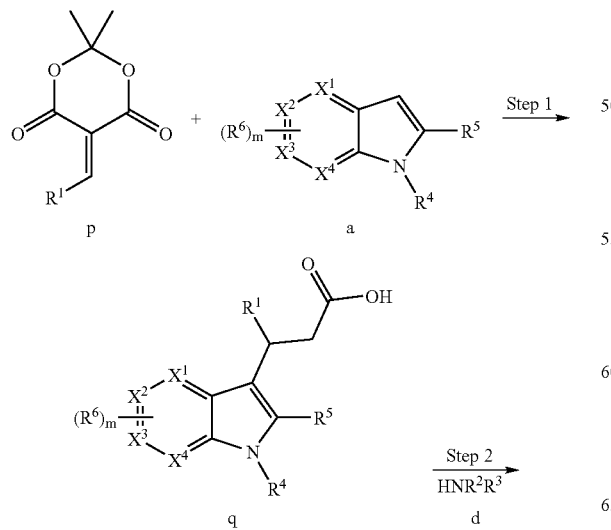

-continued

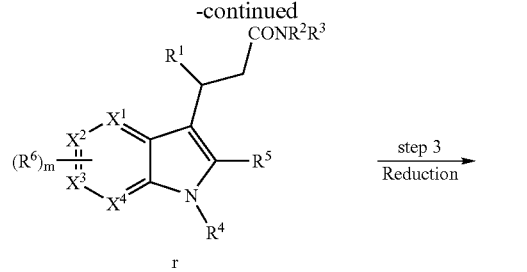

r

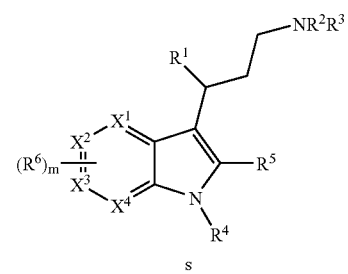

s

In Step 1 of Scheme C, substituted alkylidine Meldrum's acid compound p is reacted with azaindole a to afford pyrrolopyridine acid q. Azaindole acid q is treated with amine d in Step 2 to form azaindole amide r. In Step 3, azaindole amide r is reduced to yield aminopropyl azaindole compound s, which represents some of the compounds of formula I in accordance with the invention.

Scheme D shows another procedure for preparation of the subject compounds wherein X and Y are leaving group and may be the same or different, one or two (e.g., $X^2$ and $X^4$) of $X^1$, $X^2$, $X^3$ or $X^4$ is N and the others are CH, and m, $R^1$, $R^2$, $R^3$, $R^4$, $R^5$ and $R^6$ are as defined herein.

SCHEME D

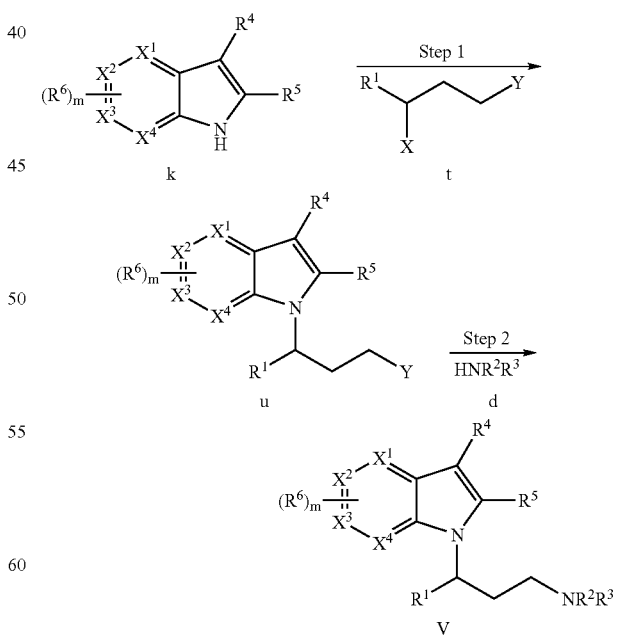

In step 1 of Scheme D, azaindole k is reacted with alkylating agent t to afford the corresponding N-alkylated azaindole u. Compound u is then treated with amine d to yield the corresponding aminopropyl azaindole v, which is a compound of formula I in accordance with the invention. In many embodiments of the procedure of Scheme D, X is OMs (methanesulfonyloxy) and Y is halo, preferably chloro.

Another route to the compounds of the invention is shown in Scheme E, wherein one of $X^1$, $X^2$, $X^3$ or $X^4$ is N and the others are CH, m, $R^1$, $R^2$, $R^3$, $R^4$, $R^5$ and $R^6$ are as defined herein.

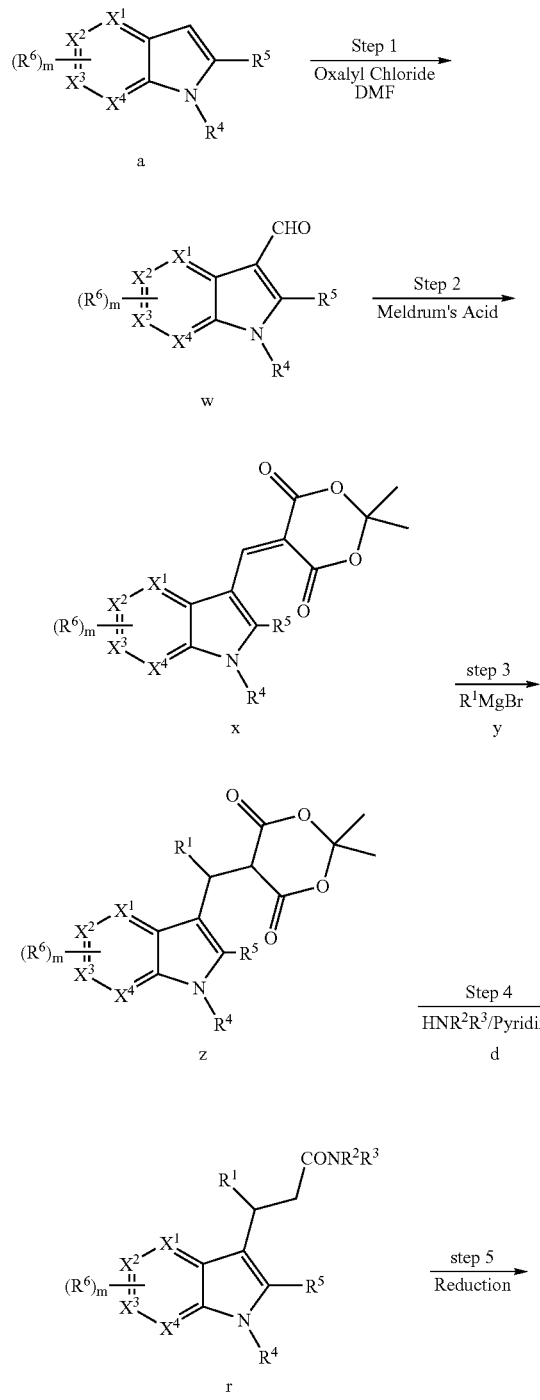

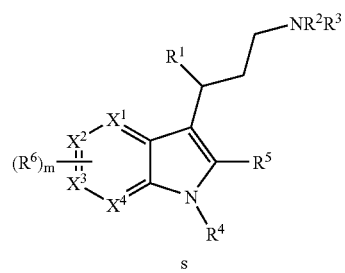

In Step 1 of Scheme E, azaindole compound a is treated with the Vilsmeier reagent formed by mixing oxalyl chloride with dimethyl formamide to form azaindole aldehyde w, which in turn is reacted with Meldrum's acid in Step 2 to yield azaindole compound x. Azaindole x is then treated with Grignard reagent y in Step 3 to afford azaindole compound z. In Step 4 compound z is reacted with amine d in the presence of pyridine to give azaindole amide r, which is then reduced in Step 5 to provide aminopropyl azaindole compound s. Compound s is one of the compounds of formula I in accordance with the invention.

Scheme F illustrates yet another synthetic approach to the compounds of the invention, wherein one or two (e.g., $X^2$ and $X^4$) of $X^1$, $X^2$, $X^3$ or $X^4$ is N and the others are CH, m, $R^1$, $R^2$, $R^3$, $R^4$, $R^5$ and $R^6$ are as defined herein.

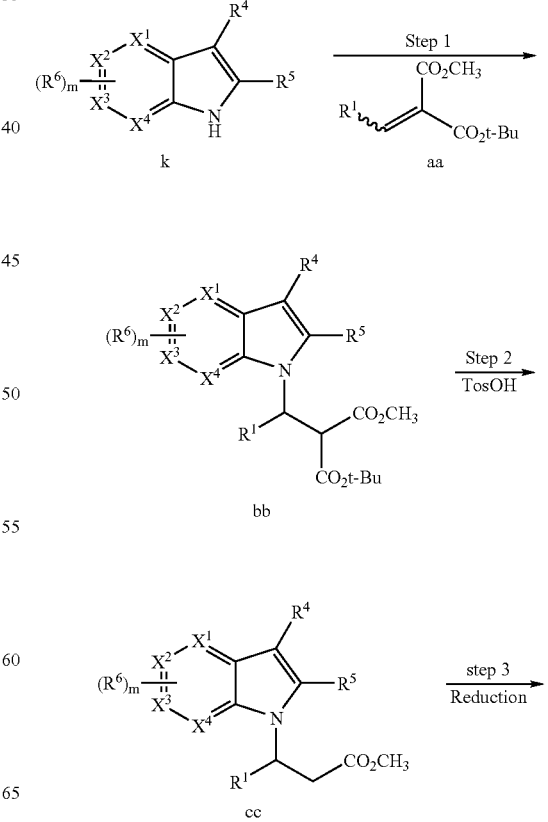

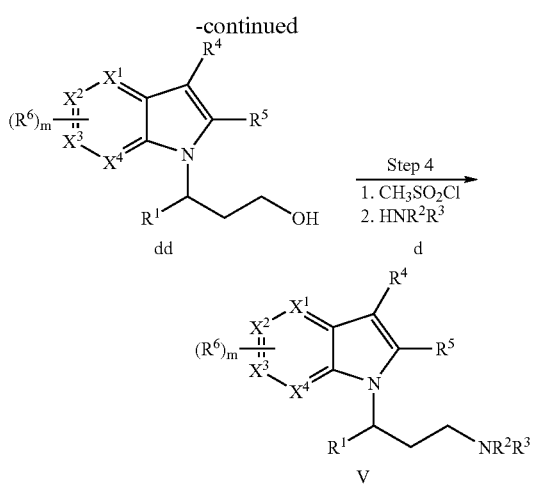

In Step 1 of Scheme F, azaindole k is reacted with mixed ester compound aa to form a corresponding azaindole diester bb. Compound bb is treated with toluene sulfonic acid or like acid in Step 2 to afford the corresponding azaindole ester compound cc. In Step 3 compound cc is reduced to give the corresponding hydroxypropyl azaindole dd. Compound dd is then treated with methanesulfonyl chloride, followed by amine d, to afford the corresponding aminopropyl azaindole v, which is a compound of formula I in accordance with the invention.

Numerous variations on the procedures of Schemes A through F are possible and will be readily apparent to those skilled in the art. For example, azaindoles a and k may be replaced by other heteroaryl compounds to provide other heteroaryl containing compounds in accordance with the invention. The procedure of step 3 of Scheme B may be carried out on compound X of Scheme A in embodiments where $R^3$ is hydrogen. The acrylic ester l used in step 1 is shown as a methyl ester. It should be readily apparent, however, that ethyl, isopropyl or other alkyl esters may be used in place thereof. Similarly, the methanesulfonyl chloride utilized in step 3 may be replaced with other alkylsulfonyl or aryl sulfonyl halides.

Specific details for producing compounds of the invention are described in the Examples section below.

Utility

The compounds of the invention are usable for the treatment of diseases or conditions associated with serotonin neurotransmission and/or norepinephrine neuortransmission. Such diseases and conditions include depressive and anxiolytic disorders, as well as schizophrenia and other psychoses, dyskinesias, drug addition, cognitive disorders, Alzheimer's disease, attention deficit disorders such as ADHD, obsessive-compulsive behaviour, panic attacks, social phobias, eating disorders such as obesity, anorexia, bulimia and "binge-eating", stress, hyperglycaemia, hyperlipidaemia, non-insulin-dependent diabetes, seizure disorders such as epilepsy, and treatment of conditions associated with neurological damage resulting from stroke, brain trauma, cerebral ischaemia, head injury, and haemorrhage.

The compounds of the invention are also usable for treatment of disorders and disease states of the urinary tract such as stress incontinence, urge incontinence, benign prostatic hypertrophy (BPH), prostatitis, detrusor hyperreflexia, outlet obstruction, urinary frequency, nocturia, urinary urgency, overactive bladder, pelvic hypersensitivity, urethritis, prostatodynia, cystitis, idiophatic bladder hypersensitivity.

The compounds of the invention also possess anti-inflammatory and/or analgesic properties in vivo, and accordingly, are expected to find utility in the treatment of disease states associated with pain conditions from a wide variety of causes, including, but not limited to, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

EXAMPLES

The following preparations and examples are given to enable those skilled in the art to more clearly understand and to practice the present invention. They should not be considered as limiting the scope of the invention, but merely as being illustrative and representative thereof. The abbreviations listed below may be used in the Examples.

ABBREVIATIONS

DCM dichloromethane/methylene chloride
DMF N,N-dimethylformamide
DMAP 4-dimethylaminopyridine
EtOAc ethyl acetate
EtOH ethanol
gc gas chromatography
HMPA hexamethylphosphoramide
hplc high performance liquid chromatography
mCPBA m-chloroperbenzoic acid
MeCN acetonitrile
MeOH methanol
NMP N-methyl pyrrolidinone
TEA triethylamine
TFA trifluoroacetic acid
THF tetrahydrofuran
LAH lithium aluminum hydride
LDA lithium diisopropylamine
TLC thin layer chromatography
RT room temperature

Example 1

N-Methyl-[3-phenyl-3-(1H-pyrrolo[2,3-b]pyridin-3-yl)-propyl]amine

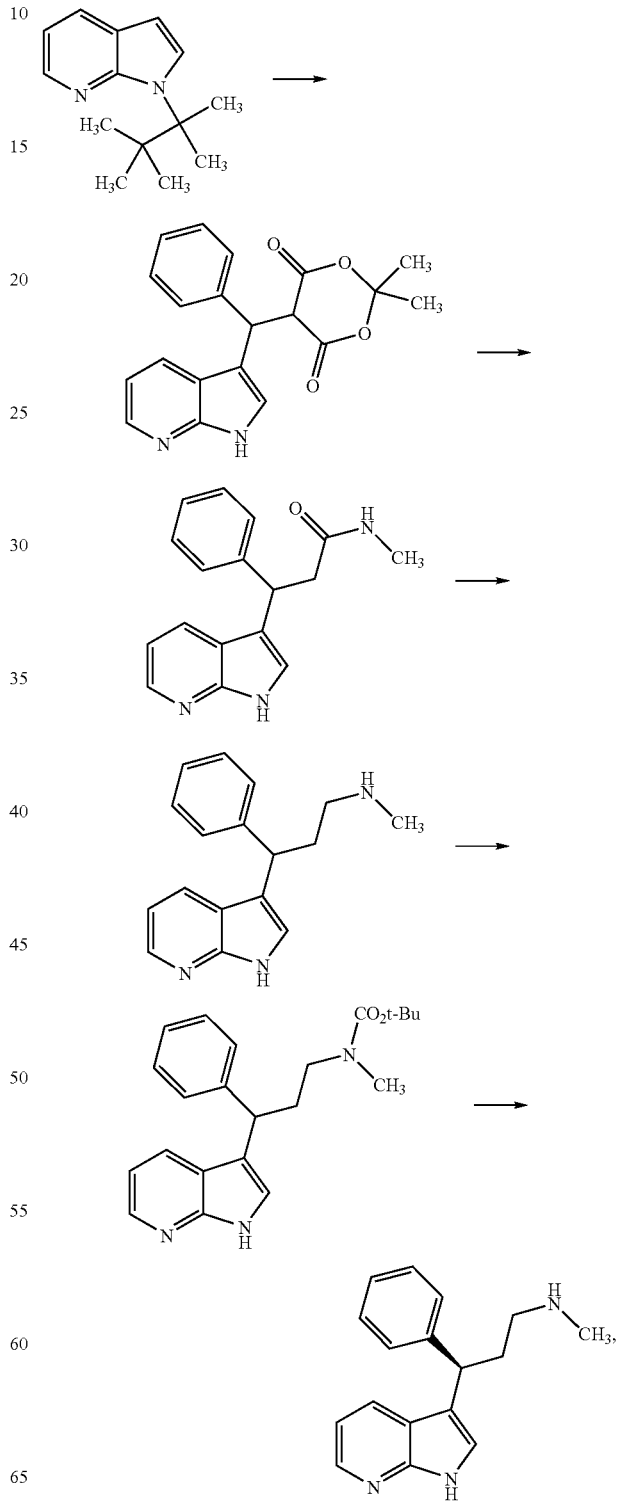

SCHEME G

-continued

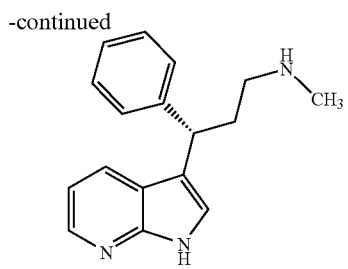

Step 1 2,2-Dimethyl-5-[phenyl-(1H-pyrrolo[2,3-b]pyridin-3-yl)-methyl]-[1,3]dioxane-4,6-dione To a room temperature (RT) solution of 1-(tert-butyl-dimethyl-silanyl)-1H-pyrrolo[2,3-b]pyridine (Synthesis 1999, 615-620) (2.88 g, 9.47 mmol) in acetonitrile (20 ml) was added Meldrum's acid (1.5 g, 10 mmol), benzaldeyde (1.9 ml, 19 mmol) triethylamine (TEA) (1.9 ml, 14 mmol) and proline (catalytic quantity). The mixture was stirred overnight at RT, concentrated, and the residue was partitioned between EtOAc and brine. The aqueous layer was extracted twice with EtOAc. The organic layers were combined, dried over $Na_2SO_4$, filtered, concentrated, and purified via flash chromatography (hexane/EtOAc), affording 2,2-dimethyl-5-[phenyl-(1H-pyrrolo[2,3-b]pyridin-3-yl)-methyl]-[1,3]dioxane-4,6-dione.

Step 2 N-Methyl-3-phenyl-3-(1H-pyrrolo[2,3-b]pyridin-3-yl)-propionamide

A sealed tube loaded with 2,2-dimethyl-5-[phenyl-(1H-pyrrolo[2,3-b]pyridin-3-yl)-methyl]-[1,3]dioxane-4,6-dione (700 mg), methylamine (2M in THF, 3 ml) and pyridine (5 ml) was stirred at 120° C. for 2 hours. The reaction mixture was cooled to RT and partitioned between $H_2O$ and EtOAc. The organic layer was separated, dried over $Na_2SO_4$, filtered, concentrated, and purified via flash chromatography (hexane/EtOAc) affording N-Methyl-3-phenyl-3-(1H-pyrrolo[2,3-b]pyridin-3-yl)-propionamide.

Step 3 N-Methyl-[3-phenyl-3-(1H-pyrrolo[2,3-b]pyridin-3-yl)-propyl]amine

To a RT suspension of N-methyl-3-phenyl-3-(1H-pyrrolo[2,3-b]pyridin-3-yl)-propionamide (54 mg, 0.19 mmol) in THF (5 ml) was added $LiAlH_4$ (0.38 ml, 1M in THF) at room temperature. The resulting mixture was refluxed for 4 h, then the same amount of $LiAlH_4$ was added. The resulting mixture was refluxed overnight, cooled to RT, quenched by addition of $Na_2SO_4.10H_2O$. The mixture was stirred for 30 min and the solid was filtered off and washed with EtOAc. The filtrate was concentrated and purified via flash chromatography (DCM/MeOH/$NH_4OH$) affording N-Methyl-[3-phenyl-3-(1H-pyrrolo[2,3-b]pyridin-3-yl)-propyl]amine as a white foam (28 mg, 56% yield); MS M+H=266.

Step 4 Preparation and Resolution of (R)- and (S)-Methyl-[3-phenyl-3-(1H-pyrrolo[2,3-b]pyridin-3-yl)-propyl]-carbamic acid tert-butyl ester To a 0° C. solution of racemic methyl-[3-phenyl-3-(1H-pyrrolo[2,3-b]pyridin-3-yl)-propyl]-amine (267 mg, 1.01 mmol) in DCM (40 ml) was added TEA (0.47 ml, 3.37 mmol) followed by $Boc_2O$ (416 mg, 1.91 mmol). The mixture was warmed to RT over 1 hour, and then stirred at RT for 22 hours to give a racemic mixture of Methyl-[3-phenyl-3-(1H-pyrrolo[2,3-b]pyridin-3-yl)-propyl]-carbamic acid tert-butyl ester (not isolated). The reaction mixture was concentrated under reduced pressure, and purified via chiral preparative HPLC by multiple injections onto Chiralpak AD preparative 250×20 mm (hexane/i-PrOH, 6 ml/min), affording (R)-Methyl-[3-phenyl-3-(1H-pyrrolo[2,3-b]pyridin-3-yl)-propyl]-carbamic acid tert-butyl ester (215 mg, 31% yield) as a first fraction and (S)-Methyl-[3-phenyl-3-(1H-pyrrolo[2,3-b]pyridin-3-yl)-propyl]-carbamic acid tert-butyl estere (197 mg, 28% yield) as a second fraction.

Step 5 (R)- and (S)-N-Methyl-[3-phenyl-3-(1H-pyrrolo[2,3-b]pyridin-3-yl)-propyl]amine To a RT solution of (R)-methyl-[3-phenyl-3-(1H-pyrrolo[2,3-b]pyridin-3-yl)-propyl]-carbammic acid tert-butyl ester (181 mg, 0.496 mmol) in dichloromethane (DCM) (20 ml) was added trifluoroacetic acid (TFA) (0.19 ml, 2.48 mmol). The mixture was stirred at RT for 24 hours then a second portion of TFA (95 μl, 1.24 mmol) was added. After 24 h the mixture was concentrated, and the residue was purified via flash chromatography (DCM/MeOH) affording (R)-N-Methyl-[3-phenyl-3-(1H-pyrrolo[2,3-b]pyridin-3-yl)-propyl]amine as a TFA salt (186 mg, 76% yield, $\alpha_D$=+20.4°)

Similarly, but starting with (S)-methyl-[3-phenyl-3-(1H-pyrrolo[2,3-b]pyridin-3-yl)-propyl]-carbammic acid tert-butyl ester, (S)-N-Methyl-[3-phenyl-3-(1H-pyrrolo[2,3-b]pyridin-3-yl)-propyl]amine was prepared. (175 mg, 70% yield, $\alpha_D$=−20.0°).

Example 2

[3-(4-Chloro-1H-pyrrolo[2,3-b]pyridin-3-yl-3-phenyl-propyl]-methyl-amine

SCHEME H

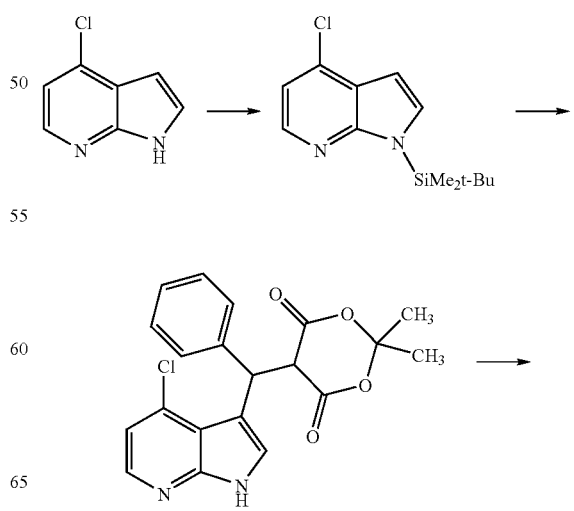

-continued

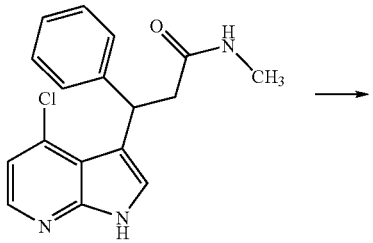

Step 1 1-(tert-Butyl-dimethyl-silanyl)-4-chloro-1H-pyrrolo[2,3-b]pyridine

To a −78° C. solution of 4-chloro-1H-pyrrolo[2,3-b]pyridine (prepared as described in WO03/082289, 1.44 g, 9.47 mmol) in THF (75 ml) was slowly added a 1.4 M solution of n-BuLi in THF (7.4 ml). The resulting mixture was stirred for 10 minutes, and then tert-butyl-dimethylsilyl chloride (1.4 g, 9.47 mmol) was added to the mixture. The reaction mixture was warm to RT overnight and partitioned between $H_2O$ and EtOAc. The organic layer was separated, washed with brine, dried, filtered, concentrated, and purified via flash chromatography (hexane/EtOAc) affording 1-(tert-Butyl-dimethyl-silanyl)-4-chloro-1H-pyrrolo[2,3-b]pyridine as a clear oil (2.0 g, 62% yield).

Step 2 5-[(4-Chloro-1H-pyrrolo[2,3-b]pyridin-3-yl)-phenyl-methyl]-2,2-dimethyl-[1,3]dioxane-4,6-dione 5-[(4-Chloro-1H-pyrrolo[2,3-b]pyridin-3-yl)-phenyl-methyl]-2,2-dimethyl-[1,3]dioxane-4,6-dione was prepared following the procedure described for preparation of 2,2-dimethyl-5-[phenyl-(1H-pyrrolo[2,3-b]pyridin-3-yl)-methyl]-[1,3]dioxane-4,6-dione in example 1, using 1-(tert-butyl-dimethyl-silanyl)-4-chloro-1H-pyrrolo[2,3-b]pyridine.

Step 3 3-(4-Chloro-1H-pyrrolo[2,3-b]pyridin-3-yl)-N-methyl-3-phenyl-propionamide 3-(4-Chloro-1H-pyrrolo[2,3-b]pyridin-3-yl)-N-methyl-3-phenyl-propionamide was prepared (73% yield) following the procedure described for preparation of N-methyl-3-phenyl-3-(1H-pyrrolo[2,3-b]pyridin-3-yl)-propionamide in Example 1, using 5-[(4-chloro-1H-pyrrolo[2,3-b]pyridin-3-yl)-phenyl-methyl]-2,2-dimethyl-[1,3]dioxane-4,6-dione.

Step 4 3-(4-Chloro-1H-pyrrolo[2,3-b]pyridin-3-yl-3-phenyl-propyl]-methyl-amine To a RT suspension of 3-(4-chloro-1H-pyrrolo[2,3-b]pyridin-3-yl)-N-methyl-3-phenyl-propionamide (80 mg, 0.25 mmol) in THF (3 ml) was added $NaBH_4.SMe_2$ (30 μl, 10M in THF). The reaction mixture was refluxed for 2 hours, and then cooled and quenched by addition of MeOH and HCl (concentrated, 3 drops). The resulting mixture was refluxed for 20 min, concentrated, and purified via flash chromatography (DCM/MeOH/$NH_4OH$) affording the compound 15 as a light yellow viscous oil (23 mg, 31% yield).

Example 3

[3-(4-Methoxy-1H-pyrrolo[2,3-b]pyridin-3-yl)-3-phenyl-propyl]-methyl-amine

SCHEME I

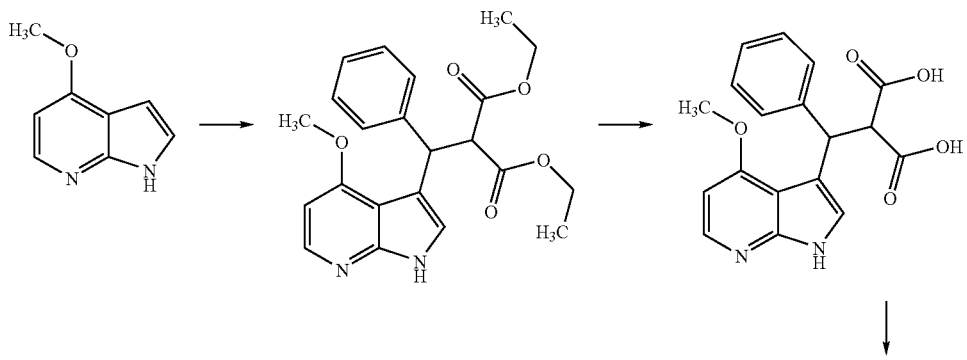

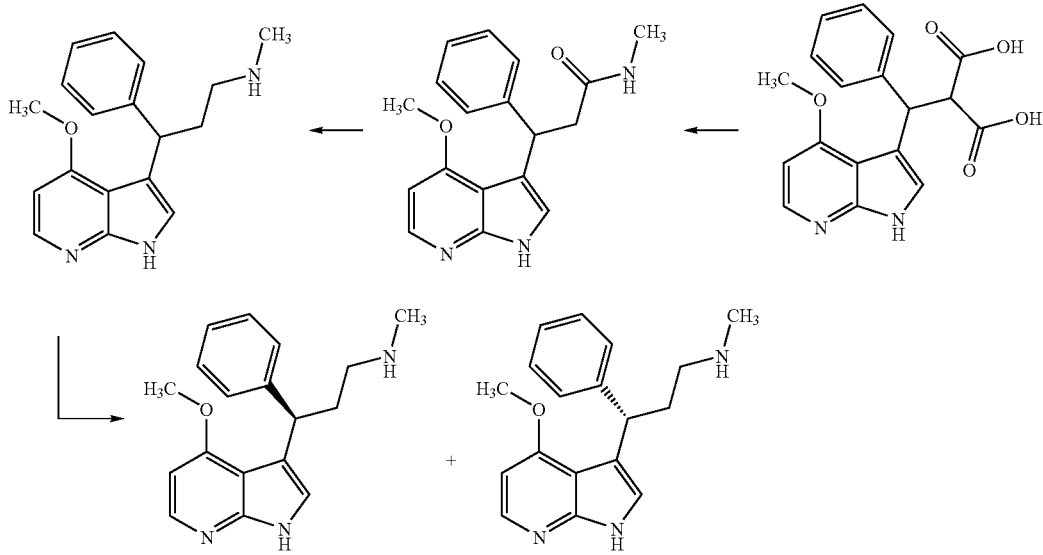

Step 1 2-[(4-Methoxy-1H-pyrrolo[2,3-b]pyridin-3-yl)-phenyl-methyl]-malonic acid diethyl ester To a RT suspension of 4-methoxy-1H-pyrrolo[2,3-b]pyridine (prepared as described in WO03/082289, 1.0 g, 6.75 mmol) in toluene (30 ml) at RT was added isopropyl magnesium chloride(1.5 M in THF, 4.95 ml, 7.43 mmol) dropwise. The resulting mixture was stirred at RT for 30 min and neat diethyl benzylidene malonate (1.82 ml, 8.10 mmol) was added dropwise. The reaction was stirred for 1 h then quenched by addition of a saturated solution of $NH_4Cl$ and diluted with $H_2O$ and EtOAc. The resulting white solid precipitate was filtered and dried affording 2-[(4-Methoxy-1H-pyrrolo[2,3-b]pyridin-3-yl)-phenyl-methyl]-malonic acid diethyl ester (2.13 g). An additional 130 mg was isolated from the mother liquors, giving 85% combined yield.

Step 2 2-[(4-Methoxy-1H-pyrrolo[2,3-b]pyridin-3-yl)-phenyl-methyl]-malonic acid To a suspension of 2-[(4-methoxy-1H-pyrrolo[2,3-b]pyridin-3-yl)-phenyl-methyl]-malonic acid diethyl ester (1.0 g, 2.52 mmol) in a mixture of THF/EtOH (1/1, 24 ml) was added $H_2O$ (2 ml) followed by KOH (1.41 g, 25.2 mmol). The reaction mixture was stirred at 50° C. for 4 h, and then cooled to RT and concentrated. The solid residue was dissolved in $H_2O$. The resulting solution was cooled to 0° C. and acidified to pH 4-5 by addition of HCl (1 M). The white solid precipitate was collected by filtration, washed with cold $H_2O$ and dried to afford 2-[(4-Methoxy-1H-pyrrolo[2,3-b]pyridin-3-yl)-phenyl-methyl]-malonic acid (809 mg, 94% yield).

Step 3 3-(4-Methoxy-1H-pyrrolo[2,3-b]pyridin-3-yl)-3-phenyl-propionic acid

2-[(4-Methoxy-1H-pyrrolo[2,3-b]pyridin-3-yl)-phenyl-methyl]-malonic acid (777 mg, 2.28 mmol) was placed in a 100 ml flask under high vacuum and heated to 160° C. The white solid melted into a orange-maroon oil and bubbling was observed. After 1 h, the reaction was cooled to RT to afford 3-(4-Methoxy-1H-pyrrolo[2,3-b]pyridin-3-yl)-3-phenyl-propionic acid (637 mg, 94% yield).

Step 4 3-(4-Methoxy-1H-pyrrolo[2,3-b]pyridin-3-yl)-N-methyl-3-phenyl-propionamide To a RT suspension of 3-(4-methoxy-1H-pyrrolo[2,3-b]pyridin-3-yl)-3-phenyl-propionic acid (635 mg, 2.14 mmol) in DCM (20 mL) was added TEA (0.45 mL, 3.21 mmol). To this mixture was added PyBOP (1.22 g, 2.35 mmol) and $MeNH_2$ (2 M in THF, 1.60 mL, 3.21 mmol). The resulting mixture was stirred at RT for 30 min, and the white precipitate was collected by filtration to afford 3-(4-Methoxy-1H-pyrrolo[2,3-b]pyridin-3-yl)-N-methyl-3-phenyl-propionamide in 72% yield (477 mg).

Step 5 [3-(4-Methoxy-1H-pyrrolo[2,3-b]pyridin-3-yl)-3-phenyl-propyl]-methyl-amine To a RT suspension of 3-(4-methoxy-1H-pyrrolo[2,3-b]pyridin-3-yl)-N-methyl-3-phenyl-propionamide (155 mg, 0.50 mmol) in THF (5 mL) was slowly added LAH (1 M in THF, 1.5 mmol). The mixture was refluxed overnight, cooled to RT, and quenched by addition of freshly ground $Na_2SO_4 \cdot 10H_2O$. After stirring for 20 min, the solid was filtered off and washed with EtOAc (10 mL, 3 times) and DCM (10 mL, 2 times). The filtrate was concentrated, and the residue was purified via flash chromatography (DCM/MeOH/$NH_4OH$) to afford [3-(4-Methoxy-1H-pyrrolo[2,3-b]pyridin-3-yl)-3-phenyl-propyl]-methyl-amine as a white solid (90 mg, 61% yield).

Step 6 Resolution of (R)- and (S)-[3-(4-Methoxy-1H-pyrrolo[2,3-b]pyridin-3-yl)-3-phenyl-propyl]-methyl-amine Racemic [3-(4-Methoxy-1H-pyrrolo[2,3-b]pyridin-3-yl)-3-phenyl-propyl]-methyl-carbamic acid tert-butyl ester was prepared following the procedure of step 4 of Example 1, and was separated by chiral preparative HPLC by multiple injections onto a Chiralcel OD preparative column 50×500 mm (hexane/i-PrOH 80/20, 50 ml/min) to afford (R)-[3-(4-Methoxy-1H-pyrrolo[2,3-b]pyridin-3-yl)-3-phenyl-propyl]-methyl-carbamic acid tert-butyl ester (200 mg,) and (S)-[3-(4-Methoxy-1H-pyrrolo[2,3-b]pyridin-3-yl)-3-phenyl-propyl]- methyl-carbamic acid tert-butyl ester (195 mg). These compounds were deprotected using the procedure of step 5 of Example 1 to respectively provide (R)-[3-(4-Methoxy-(1H-pyrrolo[2,3-b]pyridin-3-yl)-3-phenyl-propyl]-methyl-amine (216 mg, 84% yield, $\alpha_D$=+20.4°) and (S)-[3-(4-Methoxy-1H-pyrrolo[2,3-b]pyridin-3-yl)-3-phenyl-propyl]-methyl-amine (208mg, 79% yield, $\alpha_D$=−20.5°) as trifluoroacetate salts.

Example 4

2-Pyridin-3-yl-methylene-malonic acid dimethyl ester

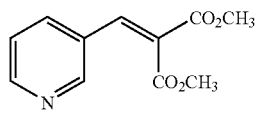

To a RT mixture of pyridin-3-carboxaldeyde (0.94 mL, 10 mmol) and dimethylmalonate (1.14 mL, 10.0 mmol) in benzene (30 mL) was added piperidine (0.10 mL, 1.0 mmol) and benzoic acid (60 mg, 0.5 mmol). The resulting mixture was stirred at reflux overnight, cooled to RT, poured into water, and extracted with EtOAc. The organic layer was separated, washed with a saturated solution of NaHCO$_3$, dried over MgSO$_4$, filtered, concentrated, and purified via flash chromatography (hexanes/EtOAc) to afford 2-Pyridin-3-yl-methylene-malonic acid dimethyl ester as a white solid (1.90 g, 86% yield).

Example 5

[3-(4-Methoxy-1H-pyrrolo[2,3-b]pyridin-3-yl)-3-pyridin-3-yl-propyl]-methyl-amine Step 1 2-[(4-Methoxy-1H-pyrrolo[2,3-b]pyridin-3-yl)-pyridin-3-yl-methyl]-malonic acid dimethyl ester A suspension of 4-methoxy-1H-pyrrolo[2,3-b]pyridine (0.5 g, 3.37 mmol) in toluene (15 ml) was cooled to 0° C., and isopropyl magnesium chloride (1.5 M in THF, 2.47 ml, 3.70 mmol) was added dropwise. The resulting mixture was stirred at RT for 30 minutes and a solution of 2-(2-pyridin-3-yl-vinyl)-malonic acid dimethyl ester (867 mg, 4.04 mmol) in toluene (4 mL) was added dropwise. The reaction was stirred for 1 hour, then was quenched by addition of a saturated solution of NH$_4$Cl. The mixture was diluted with H$_2$O and EtOAc, and the resulting white solid precipitate was collected by filtration, washed with EtOAc and dried to afford 2-[(4-Methoxy-1H-pyrrolo[2,3-b]pyridin-3-yl)-pyridin-3-yl-methyl]-malonic acid dimethyl ester in 75% yield (936 mg).

Step 2 3-(4-Methoxy-1H-pyrrolo[2,3-b]pyridin-3-yl)-pyridin-3-yl-propionic acid

To a RT suspension of 2-[(4-methoxy-1H-pyrrolo[2,3-b]pyridin-3-yl)pyridin-3-yl-methyl]-malonic acid dimethyl ester (780 mg, 2.11 mmol) in THF/MeOH (20 mL, 1/1 mixture) was added water (2 mL) followed by KOH (1,18 g, 21.1 mmol). The resulting mixture was stirred at 50° C. for 4 hours, concentrated, and the residue was dissolved in water and acidified with HCl (1 M) to pH 4. The resulting aqueous solution was heated at reflux for 1.5 h and concentrated. The residue was dissolved in MeOH (25 ml) and stirred for 30 min at RT. The white solid precipitate was filtered off and the filtrate was concentrated to afford 3-(4-Methoxy-1H-pyrrolo[2,3-b]pyridin-3-yl)-pyridin-3-yl-propionic acid.

SCHEME I

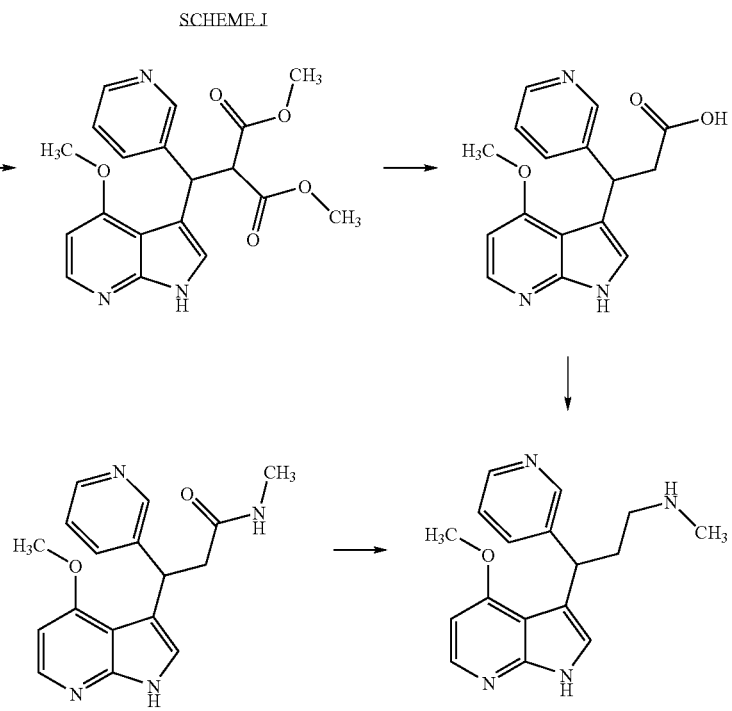

Step 3 3-(4-Methoxy-1H-pyrrolo[2,3-b]pyridin-3-yl)-N-methyl-pyridin-3-yl-propionamide To a RT solution of 3-(4-methoxy-1H-pyrrolo[2,3-b]pyridin-3-yl)-pyridin-3-yl-propionic acid (627 mg, 2.11 mmol) in DMF (15 mL) was added TEA (0.44 mL, 3.16 mmol) followed by benzotriazol-1-yloxy)tripyrrolidinophosphonium hexafluorophosphate (1.20 g, 2.32 mmol) and MeNH$_2$ (2M in THF, 1.60 mL, 3.16 mmol). The reaction mixture was stirred at RT for 1 h, quenched with H$_2$O, concentrated, and the residue was purified via flash chromatography (DCM/MeOH/NH$_4$OH) to afford the compound 26 as an off-white foam (355 mg, 54% yield over 3 steps from the diester).

Step 4 [3-(4-Methoxy-1H-pyrrolo[2,3-b]pyridin-3-yl)-3-pyridin-3-yl-propyl]-methyl-amine Following the procedure of step 5 of Example 3, [3-(4-Methoxy-1H-pyrrolo[2,3-b]pyridin-3-yl)-3-pyridin-3-yl-propyl]-methyl-amine was prepared in 42% yield (80 mg).

Example 6

Methyl-[3-pyridin-3-yl-3-(1H-pyrrolo[2,3-b]pyridin-3-yl)-propyl]-amine

Step 2 2-[Pyridin-3-yl-(1H-pyrrolo[2,3-b]pyridin-3-yl)-methyl]-malonic acid

Following the procedure of step 2 of Example 5, 2-[Pyridin-3-yl-(1H-pyrrolo[2,3-b]pyridin-3-yl)-methyl]-malonic acid was prepared from 2-[Pyridin-3-yl-(1H-pyrrolo[2,3-b]pyridin-3-yl)-methyl]-malonic acid dimethyl ester, and was used without purification in the next step.

Step 3 3-Pyridin-3-yl-3-(1H-pyrrolo[2,3-b]pyridin-3-yl)-propionic acid

Following the procedure of step 3 of Example 5, 3-Pyridin-3-yl-3-(1H-pyrrolo[2,3-b]pyridin-3-yl)-propionic acid was prepared and was used without purification in the next step.

Step 4 N-Methyl-3-pyridin-3-yl-3-(1H-pyrrolo[2,3-b]pyridin-3-yl)-propionamide To a RT suspension of 3-pyridin-3-yl-3-(1H-pyrrolo[2,3-b]pyridin-3-yl)-propionic acid (810 mg, 3.03 mmol) in DCM (30 mL) was added TEA (0.63 mL, 4.54 mmol) followed by PyBOP (1.73 g, 3.33 mmol) and MeNH$_2$ (2 M in THF, 2.27 mL, 4.54 mmol). After stirring the reaction mixture at RT for 30 min, the beige precipitate was filtered off, and the filtrate was concentrated. The crude residue was purified via flash chromatography (DCM/MeOH/NH$_4$OH) to afford N-Methyl-3-pyridin-3-yl-3-(1H-pyrrolo[2,3-b]pyridin-3-yl)-propionamide as a yellow oil (525 mg).

Step 5 Methyl-[3-pyridin-3-yl-3-(1H-pyrrolo[2,3-b]pyridin-3-yl)-propyl]-amine Methyl-[3-pyridin-3-yl-3-(1H-pyrrolo[2,3-b]pyridin-3-yl)-propyl]-amine was prepared from N-Methyl-3-pyridin-3-

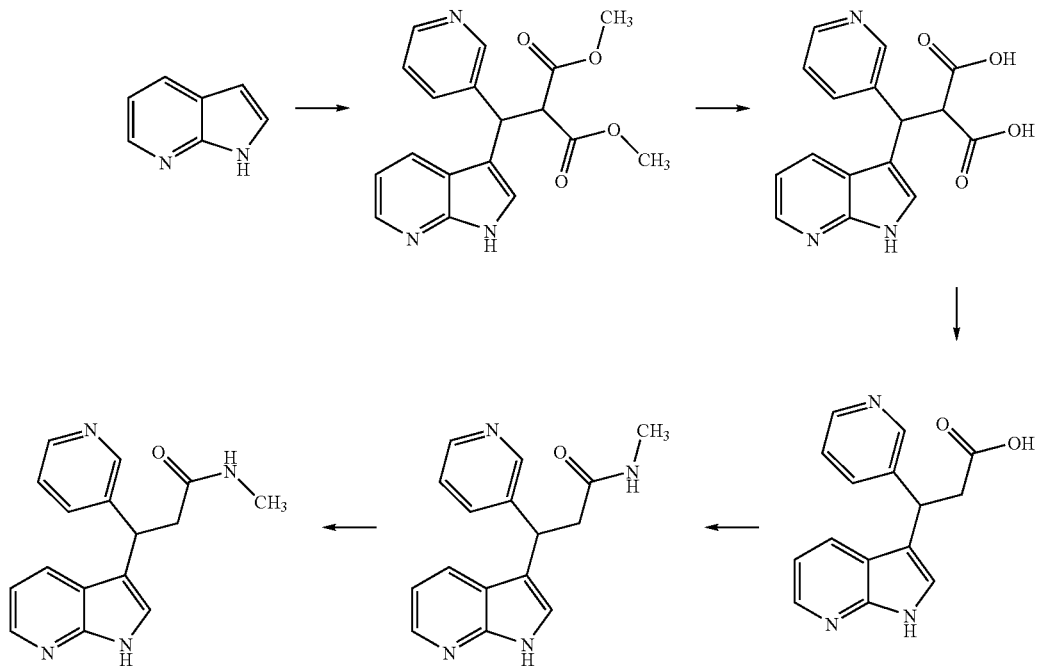

SCHEME K

Step 1 2-[Pyridin-3-yl-(1H-pyrrolo[2,3-b]pyridin-3-yl)-methyl]-malonic acid dimethyl ester Following the procedure of step 1 of Example 5, 2-[Pyridin-3-yl-(1H-pyrrolo[2,3-b]pyridin-3-yl)-methyl]-malonic acid dimethyl ester was prepared from 1H-Pyrrolo[2,3-b]pyridine in 72% yield.

yl-3-(1H-pyrrolo[2,3-b]pyridin-3-yl)-propionamide using the procedure of step 5 of Example 5, in 17% yield overall (83 mg), M+H=267.

Example 7

N-Methyl-[3-phenyl-3-(1H-pyrrolo[3 2-b]pyridin-3-yl)-propyl]-amine

Step 3 2-[Phenyl-(1H-pyrrolo[3,2-b]pyridin-3-yl)-methyl]-malonic acid tert-butyl ester methyl ester To a RT solution of PhMgBr (1 M in THF, 6.5 mL) in THF (10 mL) was added a solution of 2-(1H-pyrrolo[3,2-b]pyridin-3-yl-methylene)-malonic acid tert-butyl ester methyl ester in THF (15 mL) dropwise. After stirring the mixture for

SCHEME L

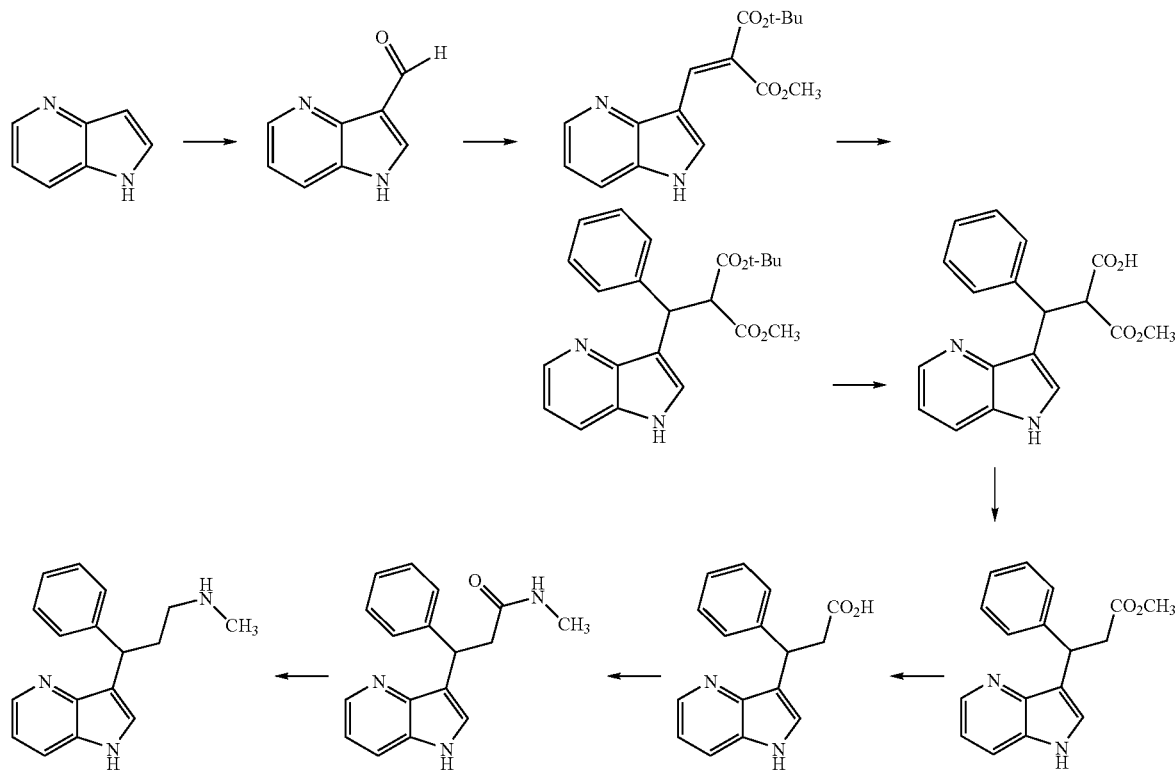

Step 1 1H-Pyrrolo[3,2-b]pyridine-3-carbaldehyde

A mixture of 1H-pyrrolo[3,2-b]pyridine (947 mg, 8.02 mmol), hexamethylenetetramine (1.7 g, 12 mmol) and acetic acid (7.5 mL) in water (14 mL) was refluxed under $N_2$ for 4 hours. The reaction mixture was cooled to RT, concentrated, and the residue was purified via flash chromatography (DCM/MeOH/NH$_4$OH) affording 1H-Pyrrolo[3,2-b]pyridine-3-carbaldehyde as a white solid (660 mg, 56% yield).

Step 2 2-(1H-Pyrrolo[3,2-b]pyridin-3-yl-methylene)-malonic acid tert-butyl ester methyl ester A mixture of 1H-pyrrolo[3,2-b]pyridine-3-carbaldehyde (660 mg, 4.5 mmol), tert-butyl-methyl malonate (3.8 mL, 22.5 mmol), piperidine (0.12 mL) and acetic acid (0.12 mL) in acetonitrile (40 mL) was heated to reflux. The resulting mixture was stirred at RT for 24 h, concentrated, and purified via flash chromatography (hexane/EtOAc) affording 2-(1H-Pyrrolo[3,2-b]pyridin-3-yl-methylene)-malonic acid tert-butyl ester methyl ester as a mixture of cis- and trans-isomers (780 mg, 57% yield).

1 hour at RT, the reaction was quenched by addition of water. The diluted mixture was neutralized by addition of HCl (1 M) to pH 7 and extracted with EtOAc. The combined organic layers were washed with brine, dried over Na$_2$SO$_4$, filtered, concentrated, and purified via flash chromatography (hexane/EtOAc) affording 2-[Phenyl-(1H-pyrrolo[3,2-b]pyridin-3-yl)-methyl]-malonic acid tert-butyl ester methyl ester (680 mg, 69% yield).

Step 4 2-[Phenyl-(1H-pyrrolo[3,2-b]pyridin-3-yl-methyl)-malonic acid mono-methyl ester A RT solution of 2-[phenyl-(1H-pyrrolo[3,2-b]pyridin-3-yl-methyl)-malonic acid tert-butyl ester methyl ester (320 mg) in a mixture TFA/DCM (2/1, 9 mL) was stirred for 1.5 h, and concentrated to give 2-[Phenyl-(1H-pyrrolo[3,2-b]pyridin-3-yl-methyl)-malonic acid mono-methyl ester as a trifluoroacetate salt.

Step 5 3-Phenyl-3-(1H-pyrrolo[3,2-b]pyridin-3-yl)-propionic acid methyl ester

2-[Phenyl-(1H-pyrrolo[3,2-b]pyridin-3-yl-methyl)-malonic acid mono-methyl ester trifluoroacetate (263 mg) was placed in an open round bottom flask and was heated to between 140° C. and 150° C. for 20 min. The black oil was cooled to RT, affording 3-Phenyl-3-(1H-pyrrolo[3,2-b]pyridin-3-yl)-propionic acid methyl ester trifluoroacetate, which was used without purification in the next step.

Step 6 3-Phenyl-3-(1H-pyrrolo[3,2-b]pyridin-3-yl)-propionic acid

To a RT solution of compound 37 in MeOH (5 mL) was added NaOH (1 M in H$_2$O, 2 mL). The reaction mixture was stirred at RT overnight and concentrated. The aqueous residue was acidified with HCl (1 M) until about pH 4 and extracted with EtOAc. The organic layer was washed with brine, dried over Na$_2$SO$_4$, filtered and concentrated to yield 3-Phenyl-3-(1H-pyrrolo[3,2-b]pyridin-3-yl)-propionic acid (150 mg).

Step 7 N-Methyl-3-phenyl-3-(1H-pyrrolo[3,2-b]pyridin-3-yl)-propionamide

To a RT solution of 3-phenyl-3-(1H-pyrrolo[3,2-b]pyridin-3-yl)-propionic acid (150 mg, 0.56 mmol) in DMF (2 mL) was added MeNH$_2$ (2 M in THF, 0.85 mL, 1.7 mmol) followed by benzotriazol-1-yloxy-tris(dimethylamino)phosphonium hexafluorophosphate (300 mg, 0.67 mmol) and TEA (0.12 mL, 0.85 mmol). The mixture was stirred at RT for 3 h, then a saturated solution of NaHCO$_3$ was added, and the mixture was extracted 3 times with EtOAc. The combined organic layers were dried over Na$_2$SO$_4$, filtered, concentrated, and purified via flash chromatography (DCM/MeOH/NH$_4$OH), affording N-Methyl-3-phenyl-3-(1H-pyrrolo[3,2-b]pyridin-3-yl)-propionamide.

Step 8 N-Methyl-[3-phenyl-3-(1H-pyrrolo[3,2-b]pyridin-3-yl)-propyl]-amine

To a RT solution of N-methyl-3-phenyl-3-(1H-pyrrolo[3,2-b]pyridin-3-yl)-propionamide (25.3 mg, 0.091 mmol) in THF (5 mL) was added BH$_3$.SMe$_2$ (10 M in THF, 18 μL). The resulting mixture was refluxed for 2 h, cooled to RT, and quenched by addition of MeOH and HCl (concentrated, 3 drops). The mixture was then heated at reflux for 15 min, cooled to RT, concentrated, and purified via flash chromatography (DCM/MeOH/NH$_4$OH), affording N-Methyl-[3-phenyl-3-(1H-pyrrolo[3,2-b]pyridin-3-yl)-propyl]-amine. MS M+H=266.

Example 8

Methyl-[3-phenyl-3-(1H-pyrrolo[3,2-c]pyridin-3-yl)-propyl]-amine

SCHEME K

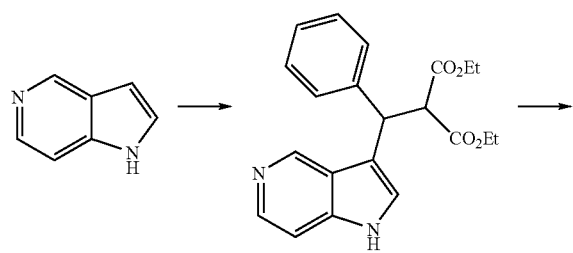

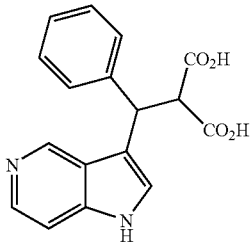

Step 1 2-[Phenyl-(1H-pyrrolo[3,2-c]pyridin-3-yl)-methyl]-malonic acid diethyl ester To a RT solution of isopropylmagnesium chloride (1.5 M in THF, 2.4 mL, 3.6 mmol) in THF (10 mL) was added a solution of 1H-pyrrolo[3,2-c]pyridine (350 mg, 3 mmol) in THF (3 mL), followed by a solution of ZnCl$_2$ in THF (1 M, 3.4 mL). After stirring the resulting mixture at 50° C. for 5 minutes, 2-benzylidene-malonic acid diethyl ester (1.0 mL, 4.5 mmol) was added dropwise. The mixture was stirred at 50° C. for 3 h, cooled to RT, quenched by addition of a saturated solution of NH$_4$Cl, and extracted 3 times with EtOAc. The combined extracts were dried over Na$_2$SO$_4$, filtered, concentrated, and purified via flash chromatography (EtOAc), affording 2-[Phenyl-(1H-pyrrolo[3,2-c]pyridin-3-yl)-methyl]-malonic acid diethyl ester (0.77 g, 70% yield).

Step 2 2-[phenyl-1H-pyrrolo[3,2-c]pyridin-3-yl)-methyl]-malonic acid

To a RT solution of 2-[phenyl-(1H-pyrrolo[3,2-c]pyridin-3-yl)-methyl]-malonic acid diethyl ester (0.77 g) in EtOH (40 mL) was added NaOH (2 M in water, 15 ml). The mixture was stirred at reflux for 5 h, cooled to RT, and concentrated. The aqueous residue was acidified by addition of HCl (1 M) until dissolution. To this solution was added EtOAc resulting in precipitation of a solid, which was collected by filtration and dried, affording 2-[Phenyl-(1H-pyrrolo[3,2-c]pyridin-3-yl)-methyl]-malonic acid (341 mg, 52% yield).

Step 3 3-Phenyl-3-(1H-pyrrolo[3,2-c]pyridin-3-yl)-propionic acid

2-[Phenyl-(1H-pyrrolo[3,2-c]pyridin-3-yl)-methyl]-malonic acid (341 mg, 1.1 mmol) was heated to 160° C. under vacuum for 1 hour and cooled to provide solid 3-Phenyl-3-(1H-pyrrolo[3,2-c]pyridin-3-yl)-propionic acid was used without purification in the next step.

Step 4 N-Methyl-3-phenyl-3-(1H-pyrrolo[3,2-c]pyridin-3-yl)-propionamide

To a RT suspension of 3-phenyl-3-(1H-pyrrolo[3,2-c]pyridin-3-yl)-propionic acid (1.1 mmol) in DCM/DMF (3/2, 5 mL) was added TEA (0.23 mL, 1.7 mmol) followed by MeNH$_2$ (2 M in THF, 0.83 mL) and benzotriazol-1-yloxy-tris(dimethylamino)phosphonium hexafluorophosphate (0.58 g, 1.3 mmol). The resulting mixture was stirred at RT overnight, diluted with an aqueous solution of NaHCO$_3$, and extracted with EtOAc. The combined organic layers were dried over Na$_2$SO$_4$, filtered, concentrated, and purified via flash chromatography (DCM/MeOH/NH$_4$OH), affording N-Methyl-3-phenyl-3-(1H-pyrrolo[3,2-c]pyridin-3-yl)-propionamide (0.16 g).

Step 5 Methyl-[3-phenyl-3-(1H-pyrrolo[3,2-c]pyridin-3-yl)-propyl]-amine

Methyl-[3-phenyl-3-(1H-pyrrolo[3,2-c]pyridin-3-yl)-propyl]-amine was prepared from N-methyl-3-phenyl-3-(1H-pyrrolo[3,2-c]pyridin-3-yl)-propionamid using the procedure described in Example 3. The free amine was converted to a bis-hydrochloride salt by addition of HCl (2M in Et$_2$O), (43.5 mg, 23% yield). MS M+H=266.

Example 9

Methyl-[3-phenyl-3-(1H-pyrrolo[2,3-c]pyridin-3-yl)-propyl]-amine

SCHEME L

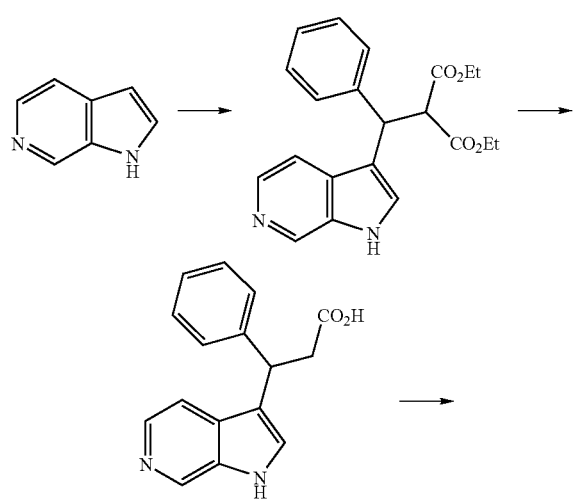

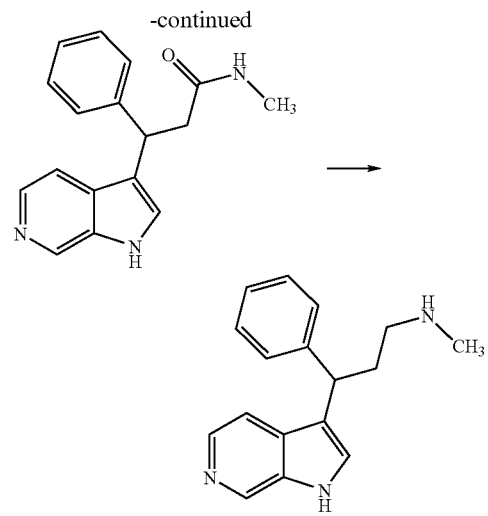

Step 1 2-[Phenyl-(1H-pyrrolo[2,3-c]pyridin-3-yl)-methyl]-malonic acid diethyl ester To a RT solution of 1H-pyrrolo[2,3-c]pyridine (595 mg, 5.04 mmol) in THF (20 mL) was added i-PrMgCl (1.5 M in THF, 5.0 mL, 7.6 mmol) followed by ZnCl$_2$ (1M in Et$_2$O, 7.6 mL). The resulting mixture was stirred at RT for 5 min then a solution of 2-benzylidene-malonic acid diethyl ester (2.2 mL, 10 mmol) in THF (20 mL) was added dropwise. The mixture was stirred at RT for 1 hour, quenched by addition of a saturated solution of NH$_4$Cl, and extracted with EtOAc. The combined extracts were washed with brine, dried over Na$_2$SO$_4$, filtered, concentrated, and purified via flash chromatography (DCM/MeOH/NH$_4$OH), affording 2-[Phenyl-(1H-pyrrolo[2,3-c]pyridin-3-yl)-methyl]-malonic acid diethyl ester (0.33 g, 18% yield).

Step 2 3-Phenyl-3-(1H-pyrrolo[2,3-c]pyridin-3-yl)-propionic acid

To a RT solution of 2-[phenyl-(1H-pyrrolo[2,3-c]pyridin-3-yl)-methyl]-malonic acid diethyl ester (0.33 g) in MeOH (30 mL) was added NaOH (2 M in water, 10 ml). The mixture was refluxed for 5h, cooled to RT, and concentrated. The residue was acidified by addition of HCl (1 M) and extracted with EtOAc. The combined extracts were refluxed for 10 h, cooled to RT, and concentrated. The residue was partitioned between water and EtOAc and extracted 3 times with EtOAc. The combined organic layers were dried over Na$_2$SO$_4$, filtered, and concentrated, affording crude 3-Phenyl-3-(1H-pyrrolo[2,3-c]pyridin-3-yl)-propionic acid (224 mg, 94% yield), which was used in the next step without further purification.

Step 3 N-Methyl-3-phenyl-3-(1H-pyrrolo[2,3-c]pyridin-3-yl)-propionamide

N-Methyl-3-phenyl-3-(1H-pyrrolo[2,3-c]pyridin-3-yl)-propionamide was prepared from 3-phenyl-3-(1H-pyrrolo[2,3-c]pyridin-3-yl)-propionic acid using the procedure of step 4 of Example 8, 54% yield (128 mg).

Step 4 Methyl-[3-phenyl-3-(1H-pyrrolo[2,3-c]pyridin-3-yl)-propyl]-amine

Methyl-[3-phenyl-3-(1H-pyrrolo[2,3-c]pyridin-3-yl)-propyl]-amine was prepared from N-methyl-3-phenyl-3-(1H-pyrrolo[2,3-c]pyridin-3-yl)-propionamide using the procedure of step 5 of Example 3 and was converted to a hydrochloride salt by addition of HCl (2M in Et$_2$O), (81 mg, 52% yield). MS M+H=266.

Example 10

[3-(4-Fluoro-phenyl)-3-(1H-pyrrolo[2,3-b]pyridin-3-yl)-propyl]-methyl-amine

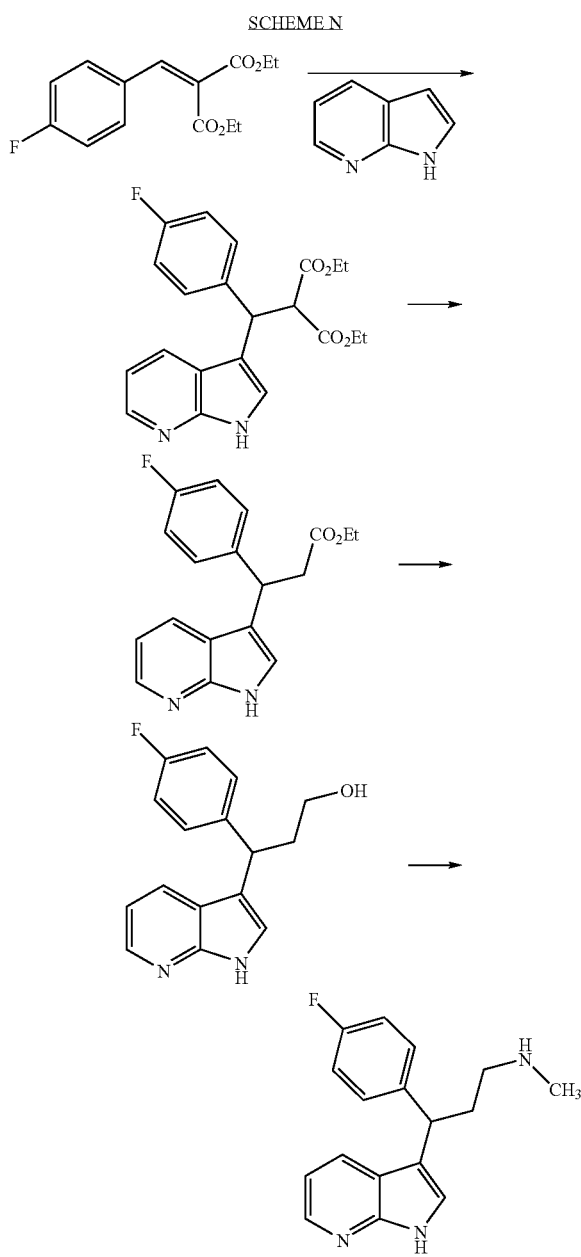

SCHEME N

Step 1 2-[(4-Fluoro-phenyl)-(1H-pyrrolo[2,3-b]pyridin-3-yl)-methyl]-3-oxo-pentanoic acid ethyl ester The 2-(4-Fluorobenzylidene)malonic acid diethyl ester used in this step was prepared following the procedure described in Example 4, and was obtained in 100% yield (4.95 g). 2-[(4-Fluoro-phenyl)-(1H-pyrrolo[2,3-b]pyridin-3-yl)-methyl]-3-oxo-pentanoic acid ethyl ester was prepared from 2-(4-fluoro-benzylidene)-malonic acid diethyl ester and 1H-pyrrolo[2,3-b]pyridine, using the procedure of step 1 of Example 5 (66% yield, 4.3 g).

Step 2 3-(4-Methoxy-1H-pyrrolo[2,3-b]pyridin-3-yl)-pyridin-3-yl-propionic acid To a RT mixture of 2-[(4-fluoro-phenyl)-(1H-pyrrolo[2,3-b]pyridin-3-yl)-methyl]-3-oxo-pentanoic acid ethyl ester (1 g, 2.6 mmol) in THF/EtOH (40 mL, 1/1 mixture) was added KOH pellets (5.2 mmol). The resulting mixture was stirred at RT for 8 hours, then poured in to a saturated solution of NH$_4$Cl, and neutralized until pH 7 by addition of HCl (2 M). The resulting solution was extracted twice with DCM and twice with EtOAc. The combined organic layers were dried over Na$_2$SO$_4$, filtered and concentrated. The aqueous residue was heated to 160° C. for 1 h, cooled to RT, and purified via flash cromatography, affording 3-(4-Methoxy-1H-pyrrolo[2,3-b]pyridin-3-yl)-pyridin-3-yl-propionic acid as a white solid (400 mg).

Step 3 3-(4-Fluoro-phenyl)-3-(1H-pyrrolo[2,3-b]pyridin-3-yl)-propan-1-ol

To a RT solution of 3-(4-methoxy-1H-pyrrolo[2,3-b]pyridin-3-yl)-pyridin-3-yl-propionic acid (200 mg, 0.65 mmol) in THF (10 mL) was added lithium aluminum hydride (1 M in THF, 1.65 mL). The mixture was stirred at 60° C. overnight. The reaction was quenched by addition of excess Na$_2$SO$_4$.10H$_2$O, and the resulting suspension was filtered. The filtrate was concentrated to provide crude 3-(4-Fluoro-phenyl)-3-(1H-pyrrolo[2,3-b]pyridin-3-yl)-propan-1-ol in quantitative yield, which was used in the next step without further purification.

Step 4 [3-(4-Fluoro-phenyl)-3-(1H-pyrrolo[2,3-b]pyridin-3-yl)-propyl]-methyl-amine To a 0° C. solution of 3-(4-fluoro-phenyl)-3-(1H-pyrrolo[2,3-b]pyridin-3-yl)-propan-1-ol (188 mg, 0.69 mmol) in THF (10 mL) was added TEA (125 μL, 0.90 mmol). After stirring the resulting mixture at 0° C. for 5 min, MsCl (59 μL, 0.76 mmol) was added, and the mixture was stirred at 0° C. for additional 2 h, poured into a saturated solution of NaHCO$_3$, and extracted twice with EtOAc (50 mL).

The combined organic layers were dried over MgSO$_4$, filtered, and concentrated to yield a yellow oil.

The resulting residue was dissolved in MeNH$_2$ (33% in EtOH, 15 mL) and the half of the mixture was transferred to a sealed tube and heated to 60° C. for 3 h. The reaction mixture was cooled to RT, concentrated, and purified via flash chromatography affording the compound 54 (5 mg, 3% yield).

Example 11

Methyl-[7-(3-methylamino-1-phenyl-propyl)-7H-pyrrolo[2,3-d]pyrimidin-4-yl]-amine

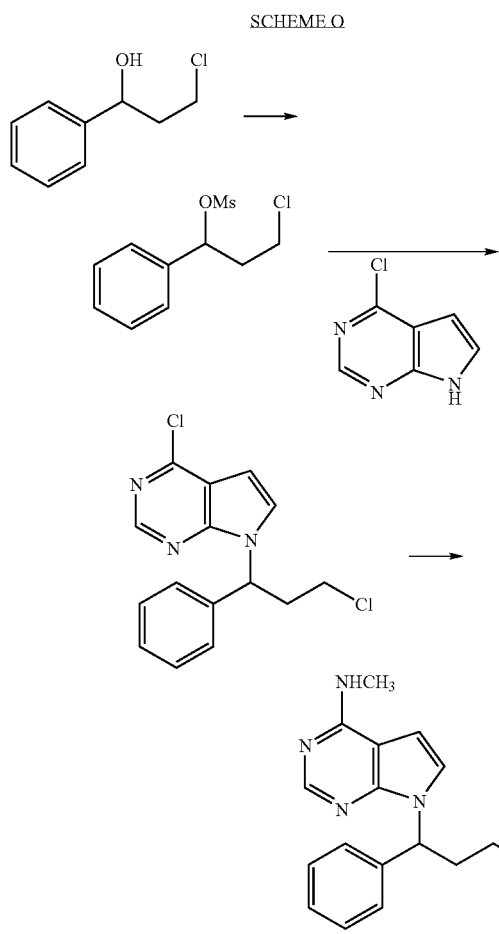

Step 1 Methanesulfonic acid 3-chloro-1-phenyl-propyl ester

The 3-Chloro-1-phenyl-propan-1-ol used in this step was prepared from a solution of (1,3-dichloro-propyl)-benzene (5 g, 30 mmol) in Et$_2$O (200 mL) by adding lithium aluminum hydride (1 M in THF, 30 mL) at 0° C. over 35 minutes. After completing the addition, the reaction was quenched at 0° C. by slow addition of freshly ground Na$_2$SO$_4$.10H$_2$O until no more gas evolution was observed. The resulting mixture was stirred for 1 h, and the solid was filtered off and washed with Et$_2$O and EtOAc. The filtrate was concentrated, and the residue was purified via flash chromatography (hexane/EtOAc, 8/2), affording 3-Chloro-1-phenyl-propan-1-ol (4.26 g).

To a solution of the 3-chloro-1-phenyl-propan-1-ol (1.5 g, 8.79 mmol) in DCM at 0° C. (50 mL) was added TEA (1.6 mL, 11.4 mmol) followed by MsCl (0.75 mL, 9.7 mmol). The reaction mixture was stirred 1.5 hours at 0° C., quenched with ice, and partitioned between a saturated solution of NaHCO$_3$ and DCM. The organic layer was separated, washed with brine, dried over MgSO$_4$, filtered, and concentrated at 0° C. The methanesulfonic acid 3-chloro-1-phenyl-propyl ester (95% crude yield, 2.08 g) thus prepared was used in the next step without purification.

Step 2 4-Chloro-7-(3-chloro-1-phenyl-propyl)-7H-pyrrolo[2,3-d]pyrimidine

To a RT solution of 4-chloro-7H-pyrrolo[2,3-d]pyrimidine (424 mg, 2.76 mmol) in DMF (3 mL) was added NaH (60% in mineral oil, 121 mg, 3.03 mmol). The reaction mixture was stirred for 30 min at RT and then a solution of methanesulfonic acid 3-chloro-1-phenyl-propyl ester in DMF (2 mL) was added at 0° C. The resulting mixture was stirred overnight at RT and then diluted with H$_2$O and EtOAc. The organic layer was separated, washed 3 times with water, dried over MgSO$_4$, filtered, concentrated, and purified via flash chromatography (hexane/EtOAc), affording 4-Chloro-7-(3-chloro-1-phenyl-propyl)-7H-pyrrolo[2,3-d]pyrimidine as a colorless oil (480 mg, 56% yield).

Step 3 Methyl-[7-(3-methylamino-1-phenyl-propyl)-7H-pyrrolo[2,3-d]pyrimidin-4-yl]-amine A mixture of 4-chloro-7-(3-chloro-1-phenyl-propyl)-7H-pyrrolo[2,3-d]pyrimidine (168 mg, 0.54 mmol) and MeNH$_2$ (33% in EtOH, 4 mL) was heated to about 100° C. by microwave for 1 hour. The reaction mixture was then cooled, concentrated, and purified via flash chromatography (DCM/MeOH/NH$_4$OH, 8/2/1), affording Methyl-[7-(3-methylamino-1-phenyl-propyl)-7H-pyrrolo[2,3-d]pyrimidin-4-yl]-amine as a light brown foam in 29% yield (48 mg).

Example 12

7-(3-Chloro-1-pheopyl)-7H-pyrrolo[2,3-d]pyrimidine

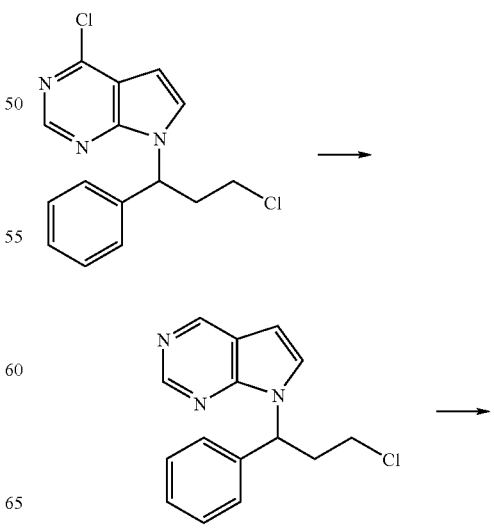

-continued

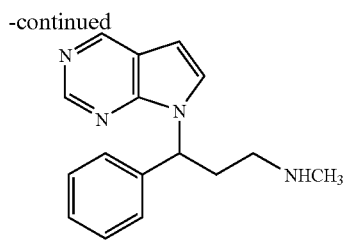

Step 1 7-(3-Chloro-1-phenyl-propyl)-7H-pyrrolo[2,3-d]pyrimidine

A suspension of 4-chloro-7-(3-chloro-1-phenyl-propyl)-7H-pyrrolo[2,3-d]pyrimidine (150 mg, 0.5 mmol) and Pd/C (10%, 50% water, 150 mg) in EtOAc (50 mL) was stirred under $H_2$ atmosphere (balloon pressure) for 4 h. The reaction mixture was filtered through a celite pad, and the filter cake was washed with EtOAc (20 mL). The filtrate was concentrated and purified via flash chromatography (hexane/EtOAc), affording 7-(3-Chloro-1-phenyl-propyl)-7H-pyrrolo[2,3-d]pyrimidine (111 mg, 83% yield).

Step 2 Methyl-(3-phenyl-3-pyrrolo[2,3-d]pyrimidin-7-yl-propyl)-amine bishydrochloride salt Methyl-(3-phenyl-3-pyrrolo[2,3-d]pyrimidin-7-yl-propyl)-amine was prepared from 7-(3-chloro-1-phenyl-propyl)-7H-pyrrolo[2,3-d]pyrimidine (48% yield, 48 mg), following the procedure of step 3 of Example 11. Treatment with HCl (2 M in $Et_2O$) afforded the corresponding bis-hydrochloride salt (52 mg). MS M+H=272.

Example 13

Methyl-(3-phenyl-3-pyrrolo[2,3-b]pyridin-1-yl-propyl)-amine

SCHEME Q

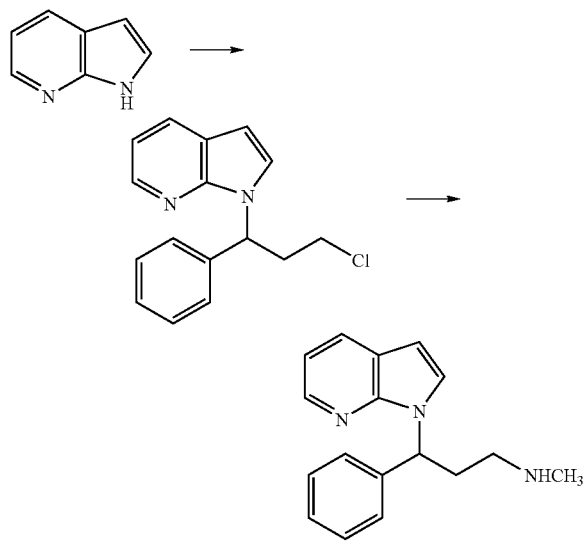

Step 1 1-(3-Chloro-1-phenyl-propyl)-1H-pyrrolo[2,3-b]pyridine 1-(3-Chloro-1-phenyl-propyl)-1H-pyrrolo[2,3-b]pyridine was prepared from 1H-pyrrolo[2,3-b]pyridine by following the procedure described in steps 1 and 2 of Example 11 (10% yield, 78 mg).

Synthesis of Methyl-(3-phenyl-3-pyrrolo[2,3-b]pyridin-1-yl-propyl)-amine

Methyl-(3-phenyl-3-pyrrolo[2,3-b]pyridin-1-yl-propyl)-amine was prepared from using 1-(3-chloro-1-phenyl-propyl)-1H-pyrrolo[2,3-b]pyridine following the procedure of step 3 of Example 11 (18% yield, 11 mg), and was with HCl (1M in $Et_2O$) to give the corresponding bis-hydrochloride salt (11 mg). MS M+H=271.

Example 14

Methyl-(3-phenyl-3-pyrrolo[3,2-b]pyridin-1-yl-propyl)-amine

SCHEME R

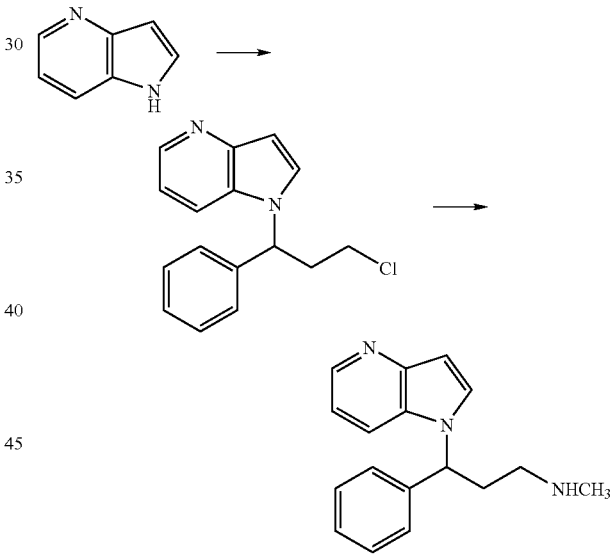

Step 1 1-(3-Chloro-1-phenyl-propyl)-1H-pyrrolo[3,2-b]pyridine 1-(3-Chloro-1-phenyl-propyl)-1H-pyrrolo[3,2-b]pyridine was prepared from 1H-pyrrolo[3,2-b]pyridine following the procedure described in steps 1 and 2 of Example 11 (66% yield, 98 mg).

Step 2 Methyl-(3-phenyl-3-pyrrolo[3,2-b]pyridin-1-yl-propyl)-amine

Methyl-(3-phenyl-3-pyrrolo[3,2-b]pyridin-1-yl-propyl)-amine was prepared from 1-(3-chloro-1-phenyl-propyl)-1H-pyrrolo[3,2-b]pyridine, following the procedure of step 3 of Example 11 (80% yield, 78 mg) as an off-white solid.

Example 15

(S)-Methyl-(3-phenyl-3-pyrrolo[3,2-b]pyridin-1-yl-propyl)-amine

SCHEME S

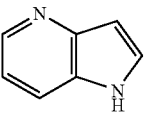

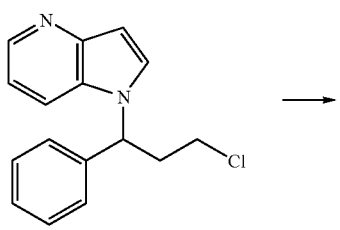

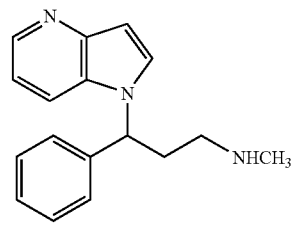

Step 1 (S) 1-(3-Chloro-1-phenyl-propyl)-1H-pyrrolo[3,2-b]pyridine 1-(3-Chloro-1-(S)-phenyl-propyl)-1H-pyrrolo[3,2-b]pyridine was prepared from 1H-pyrrolo[3,2-b]pyridine and 3-chloro-1-(R)-phenyl-propan-1-ol following the procedure described in steps 1 and 2 of Example 11 (24% yield [268 mg, $\alpha_D$=−111.0° (MeOH, c=1)].

Step 2 (S)-Methyl-(3-phenyl-3-pyrrolo[3,2-b]pyridin-1-yl-propyl)-amine

Methyl-(3-(S)-phenyl-3-pyrrolo[3,2-b]pyridin-1-yl-propyl)-amine was prepared from 1-(3-Chloro-1-(S)-phenyl-propyl)-1H-pyrrolo[3,2-b]pyridine, following the procedure of step 3 of Example 11 (76% yield, 188 mg), and was treated with HCl (1 M in Et$_2$O) to afford the corresponding bis-hydrochloride salt (219 mg, 78% yield) as a white solid. MS M+H=271.

Example 16

Methyl-[3-(4-oxy-pyrrolo[3,2-b]pyridin-1-yl)-3-phenyl-propyl]-amine

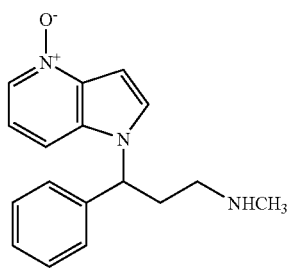

To a 0° C. solution of 1-(3-chloro-1-phenyl-propyl)-1H-pyrrolo[3,2-b]pyridine (75 mg 0.27 mmol) in DCM (5 mL) was added m-CPBA (62 mg, 0.27 mmol). The mixture was stirred for 1 h at 0° C., then poured into an aqueous solution of Na$_2$S$_2$O$_3$ (10%, 20 mL) and extracted twice with DCM (30 mL). The combined organic extracts were washed with NaHCO$_3$ (saturated solution), dried over Na$_2$SO$_4$, filtered and concentrated. The residue was treated with MeNH$_2$ (33% in EtOH, 2.5 mL) by microwave at 100° C. for 1 hours. The mixture was concentrated, and the residue was purified via flash chromatography (DCM/MeOH/NH$_4$OH), affording Methyl-[3-(4-oxy-pyrrolo[3,2-b]pyridin-1-yl)-3-phenyl-propyl]-amine as an off-white foam in 59% yield (45 mg).

Example 17

[3-(5-Methoxy-pyrrolo[3,2-b]pyridin-1-yl)-3-phenyl-propyl]-methyl-amin

SCHEME T

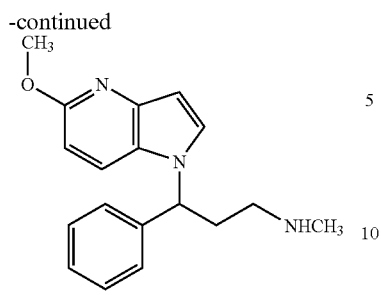

Step 1 5-Methoxy-1H-pyrrolo[3,2-b]pyridine

A suspension of (5-methoxy-3-nitro-pyridin-2-yl)-acetonitrile (Maybridge, 986 mg, 5.1 mmol) and Pd/C (10%, 986 mg) in EtOH/EtOAc (95/5, 50 mL) was shaken for 6 hours under H$_2$ (60 PSI) in Parr apparatus. The reaction mixture was then filtered through a celite pad, and the filter cake was washed with EtOAc (20 mL). The filtrate was concentrated, and the residue was dissolved in EtOAc (50 mL), washed with NaHCO$_3$ (saturated solution, 50 mL), dried over MgSO$_4$, filtered, concentrated, and purified via flash chromatography (hexane/EtOAc), affording 5-Methoxy-1H-pyrrolo[3,2-b]pyridine as a white solid (720 mg, 95% yield).

Step 2 1-(3-Chloro-1-phenyl-propyl)-5-methoxy-1H-pyrrolo[3,2-b]pyridine 1-(3-Chloro-1-phenyl-propyl)-5-methoxy-1H-pyrrolo[3,2-b]pyridine was prepared from 5-methoxy-1H-pyrrolo[3,2-b]pyridine following the procedure of steps 1 and 2 of Example 11 (62% yield, 723 mg).

Step 3 [3-(5-Methoxy-pyrrolo[3,2-b]pyridin-1-yl)-3-phenyl-propyl]-methyl-amine

[3-(5-Methoxy-pyrrolo[3,2-b]pyridin-1-yl)-3-phenyl-propyl]-methyl-amine was prepared from 1-(3-chloro-1-phenyl-propyl)-5-methoxy-1H-pyrrolo[3,2-b]pyridine following the procedure of step 3 of Example 11 (55% yield, 120 mg).

Example 18

Methyl-(3-phenyl-3-pyrrolo[3,2-c]pyridin-1-yl-propyl)-amine

SCHEME U

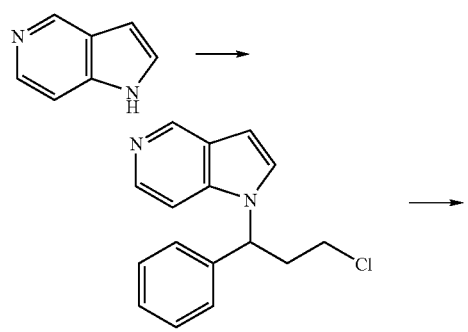

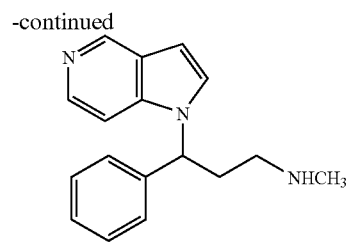

Step 1 1-(3-Chloro-1-phenyl-propyl)-1H-pyrrolo[3,2-c]pyridine 1-(3-Chloro-1-phenyl-propyl)-1H-pyrrolo[3,2-c]pyridine was prepared from 1H-pyrrolo[3,2-c]pyridine following the procedure of steps 1 and 2 of Example 11 (31% yield, 220 mg).

Step 2 Methyl-(3-phenyl-3-pyrrolo[3,2-c]pyridin-1-yl-propyl)-amine

Methyl-(3-phenyl-3-pyrrolo[3,2-c]pyridin-1-yl-propyl)-amine was prepared from 1-(3-chloro-1-phenyl-propyl)-1H-pyrrolo[3,2-c]pyridine following the procedure of step 3 of Example 11 (65% yield, 115 mg) a, and was treated with HCl (1 M in Et$_2$O) to give the correspondent bis-hydrochloride salt (100 mg). MS M+H=271.

Example 19

SCHEME V

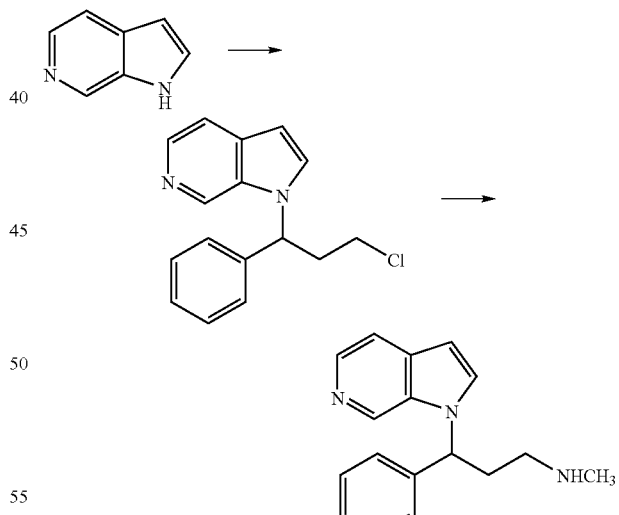

Step 1 1H-Pyrrolo[2,3-c]pyridine

A suspension of 7-chloro-1H-pyrrolo[2,3-c]pyridine (650 mg, 4.2 mmol) and Pd/C (10%, 50 mg) in EtOH (25 mL) was stirred at RT under H$_2$ atmosphere (balloon pressure). The reaction mixture was filtered through a celite pad, and the filter cake was washed with EtOAc (10 mL). The filtrate was concentrated and purified via flash chromatography (DCM/

MeOH/NH$_4$OH, 9/1/0.1), affording 1H-Pyrrolo[2,3-c]pyridine as a white solid (380 mg, 75% yield).

Step 2 1-(3-Chloro-1-phenyl-propyl)-1H-pyrrolo[2,3-c]pyridine 1-(3-Chloro-1-phenyl-propyl)-1H-pyrrolo[2,3-c]pyridine was prepared from 1H-pyrrolo[2,3-c]pyridine following the procedure of steps 1 and 2 of Example 11 (25% yield).

Step 3 Methyl-(3-phenyl-3-pyrrolo[2,3-c]pyridin-1-yl-propyl)-amine

Methyl-(3-phenyl-3-pyrrolo[2,3-c]pyridin-1-yl-propyl)-amine was prepared from 1-(3-chloro-1-phenyl-propyl)-1H-pyrrolo[2,3-c]pyridine following the procedure of step 3 of Example 11 (75% yield, 105 mg), and was treated with HCl (1 M in Et$_2$O) to give the corresponding hydrochloride salt as a white solid (65 mg).

Example 20

SCHEME W

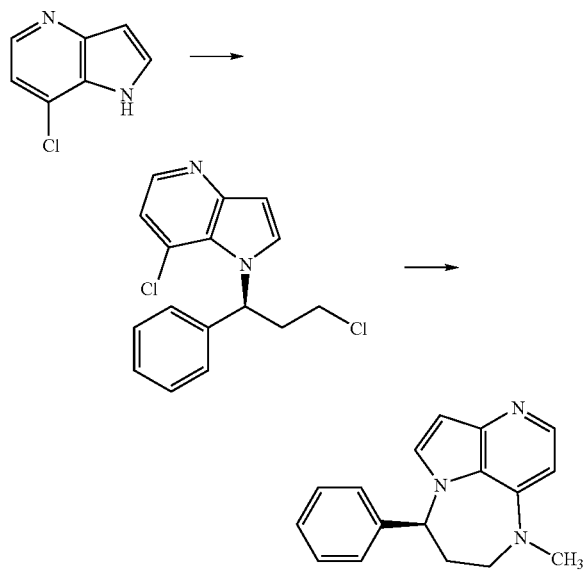

Step 1 7-Chloro-1-(3-chloro-1-(S)-phenyl-propyl)-1H-pyrrolo[3,2-b]pyridine

7-Chloro-1-(3-chloro-1-(S)-phenyl-propyl)-1H-pyrrolo[3,2-b]pyridine was prepared from 7-chloro-1H-pyrrolo[3,2-b]pyridine and 3-chloro-1-(R)-phenyl-propan-1-ol following the procedure of steps 1 and 2 of Example 11 (20% yield, 40 mg).

Step 2 (S)-6-Methyl-9-phenyl-6,7,8,9-tetrahydro-3,6,9a-triaza-benzo[cd]azulene

A RT solution of 7-chloro-1-(3-chloro-1-(S)-phenyl-propyl)-1H-pyrrolo[3,2-b]pyridine (40 mg, 0.13 mmol) in MeNH$_2$ (30% in EtOH, 2 mL) was stirred for 48 h. The mixture was concentrated, and the residue was purified via flash chromatography (DCM/MeOH/NH$_4$OH), affording (S)-6-Methyl-9-phenyl-6,7,8,9-tetrahydro-3,6,9a-triaza-benzo[cd]azulene (15 mg, 43% yield, $\alpha_D$=−75° (CHCl$_3$, c=1.2). MS M+H=264.

Example 21

3-(7-Methoxy-pyrrolo[3,2-b]pyridin-1-yl)-3-phenyl-propyl]-methyl-amine

SCHEME X

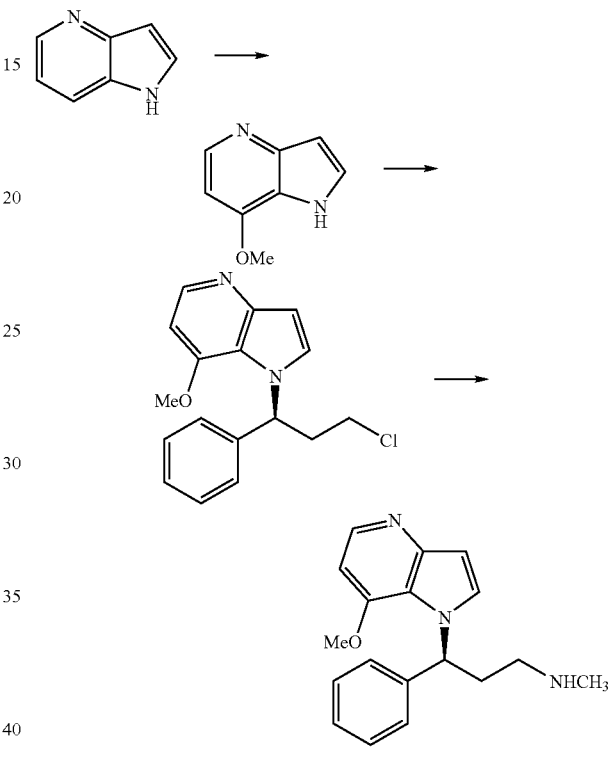

Step 1 7-Methoxy-1H-pyrrolo[3,2-b]pyridine

To a RT suspension of KOMe (24 mg, 1.65 mmol) and LiOMe (12 mg, 448 mmol) in xylene/t-BuOH (8/1, 13.5 mL) was added 7-chloro-1H-pyrrolo[3,2-b]pyridine (900 mg, 5.9 mmol). The resulting mixture was stirred at 115° C. for 48 h, then cooled to 40° C., and slowly quenched by addition of water (50 mL). The resulting mixture was cooled to 0° C. and acidified to about pH 1 by addition of HCl. The aqueous layer was separated and basified to about pH 7 to 8 by addition of NaOH (10%) and extracted 3 times with EtOAc (50 mL). The combined organic extracts were dried over Na$_2$SO$_4$, filtered, concentrated, and purified via flash chromatography (DCM/MeOH/NH$_4$OH, 9/1/0.1) affording the compound 78 as a white solid in 47% yield (412 mg).

Step 2 1-(3-Chloro-1-(S)-phenyl-propyl)-7-methoxy-1H-pyrrolo[3,2-b]pyridine 1-(3-Chloro-1-(S)-phenyl-propyl)-7-methoxy-1H-pyrrolo[3,2-b]pyridine 79 was prepared from 7-methoxy-1H-pyrrolo[3,2-b]pyridine and 3-chloro-1-(R)-phenyl-propan-1-ol following the procedure of steps 1 and 2 of Example 11 (33% yield, 170 mg, [$\alpha_D$=−149° (CHCl$_3$, c=1)])

Step 3 3-(7-Methoxy-pyrrolo[3,2-b]pyridin-1-yl)-3-phenyl-propyl]-methyl-amine

[3-(7-Methoxy-pyrrolo[3,2-b]pyridin-1-yl)-3-phenyl-propyl]-methyl-amine was prepared from 1-(3-chloro-1-(S)-phenyl-propyl)-7-methoxy-1H-pyrrolo[3,2-b]pyridine following the procedure of step 3 of Example 11 (36% yield, [98 mg, $\alpha_D$–146.9° (CHCl$_3$, c=1)]).

Example 22

Methyl-(3-pyridin-3-yl-3-pyrrolo[3,2-b]pyridin-1-yl-propyl)-amine

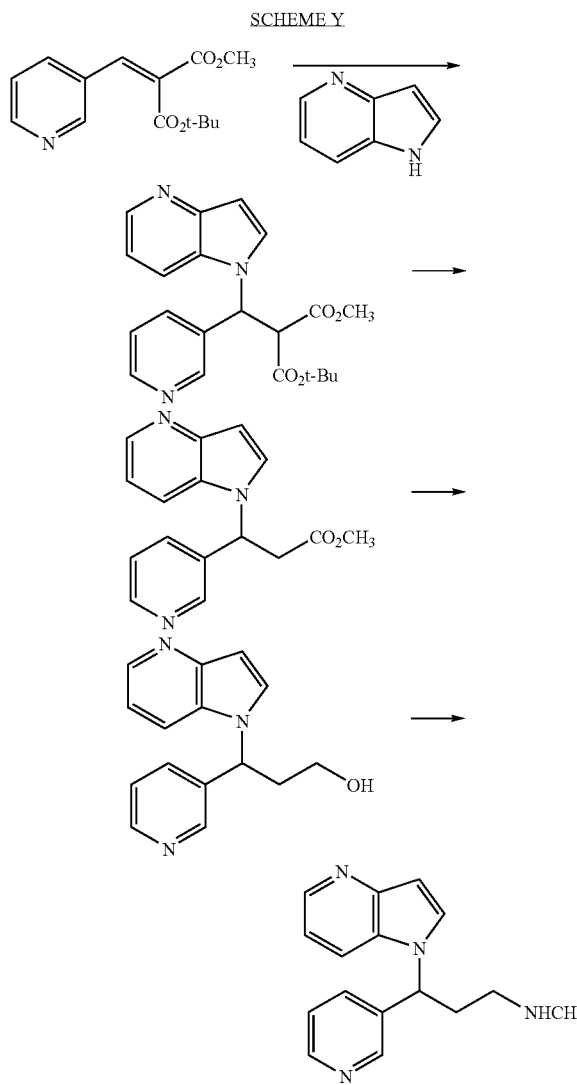

Step 1 2-Pyridin-3-yl-methylene-malonic acid tert-butyl ester methyl ester

The 2-Pyridin-3-yl-methylene-malonic acid tert-butyl ester methyl ester used in this step was prepared from tert-butyl-methylmalonate using the procedure of Example 4 (48% yield (3.21 g).

To a 0° C. solution of 1H-pyrrolo[3,2-b]pyridine (300 mg, 2.53 mmol) in DMF (20 mL) was added NaH (60% in mineral oil, 112 mg, 2.79 mmol). The resulting mixture was stirred 30 min at 0° C., then 2-pyridin-3-yl-methylene-malonic acid tert-butyl ester methyl ester (669 mg, 2.53 mmol) was added. The mixture was stirred at RT for 2 hours, poured into water (50 mL) and extracted with EtOAc (50 mL). The organic layer was washed 3 times with water (50 mL), dried over Na$_2$SO$_4$, filtered and concentrated to give 2-Pyridin-3-yl-methylene-malonic acid tert-butyl ester methyl ester in 71 % yield (694 mg), which was used in the next step without purification.

Step 2 3-Pyridin-3-yl-3-pyrrolo[3,2-b]pyridin-1-yl-propionic acid methyl ester To a RT solution of 2-(pyridin-3-yl-3-pyrrolo[3,2-b]pyridin-1-yl-methyl)-malonic acid tert-butyl ester methyl ester (694 mg, 1.82 mmol) in toluene (50 mL) was added p-TSA (727 mg, 2.1 mmol), and the mixture was stirred at reflux for 4 h. The mixture was then poured into a saturated solution of NaHCO$_3$ (100 mL) and extracted with EtOAc (50 mL). The organic layer was dried over Na$_2$SO$_4$, filtered, concentrated, and purified via flash chromatography (EtOAc), affording 3-Pyridin-3-yl-3-pyrrolo[3,2-b]pyridin-1-yl-propionic acid methyl ester (35% yield, 183 mg).

Step 3 3-Pyridin-3-yl-3-pyrrolo[3,2-b]pyridin-1-yl-propan-1-ol

To a 0° C. solution of 3-pyridin-3-yl-3-pyrrolo[3,2-b]pyridin-1-yl-propionic acid methyl ester (150 mg, 0.53 mmol) in THF (10 mL) was added LAH (1M in THF, 0.53 mL). The reaction mixture was stirred at RT for 2 h, and quenched by addition of freshly ground Na$_2$SO$_4$.10H$_2$O (1 g). The mixture was filtered through a celite pad, and the filtrate was concentrated and purified via flash chromatography (DCM/MeOH/NH$_4$OH, 8/2/0.1), affording 3-Pyridin-3-yl-3-pyrrolo[3,2-b]pyridin-1-yl-propan-1-ol (66% yield, 85 mg).

Step 4 Methyl-(3-pyridin-3-yl-3-pyrrolo[3,2-b]pyridin-1-yl-propyl)-amine

To a 0° C. solution of 3-pyridin-3-yl-3-pyrrolo[3,2-b]pyridin-1-yl-propan-1-ol (85 mg, 0.33 mmol) in DCM (10 mL) was added TEA (70 μL, 0.50 mmol) followed by MsCl (30 μL, 0.37 mmol). The reaction was stirred at 0° C. for 30 min then poured into water (50 mL) and extracted with DCM (50 mL). The organic extracts were combined, washed with a saturated solution of NaHCO$_3$ (50 mL), dried over Na$_2$SO$_4$, filtered and concentrated. The residue was dissolved in MeNH$_2$ (33% in EtOH, 4 mL) and the mixture was heated to about 100° C. by microwave for 30 minutes. The mixture was concentrated, and the residue was partitioned between DCM and a saturated solution of NaHCO$_3$. The organic layer was separated, dried over Na$_2$SO$_4$, filtered, concentrated, and purified via flash chromatography (DCM/MeOH/NH$_4$OH), affording Methyl-(3-pyridin-3-yl-3-pyrrolo[3,2-b]pyridin-1-yl-propyl)-amine (92% yield, 83 mg), which was treated with HCl (1 M in Et$_2$O) to give the correspondent hydrochloride salt as a foam (75 mg).

Example 23

SCHEME Z

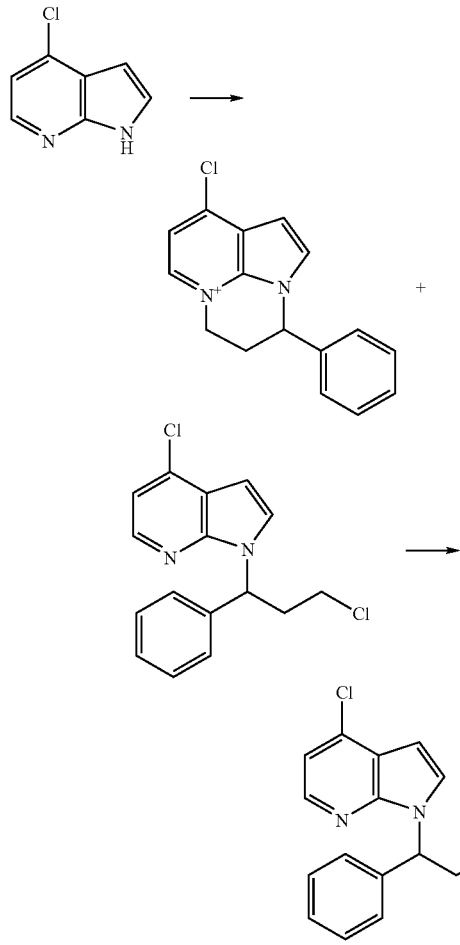

Step 1 4-Chloro-1-(3-chloro-1-phenyl-propyl)-1H-pyrrolo[2,3-b]pyridine

To a RT solution of 4-chloro-1H-pyrrolo[2,3-b]pyridine (200 mg, 1.31 mmol) in DMF (5 mL) was added NaH (60% in mineral oil, 57.7 mg, 1.44 mmol) followed by methanesulfonic acid 3-chloro-1-phenyl-propyl ester (326 mg, 1.31 mmol). The reaction mixture was stirred at RT overnight, poured into ice-water, and extracted with EtOAc. The organic layer was washed with brine, dried over MgSO$_4$, filtered and concentrated to yield 4-Chloro-1-(3-chloro-1-phenyl-propyl)-1H-pyrrolo[2,3-b]pyridine as a mixture with the cyclization product 8-Chloro-3-phenyl-4,5-dihydro-3H-2a-aza-5a-azonia-acenaphthylene. The mixture was used in the next step without purification.

Step 2 [3-(4-Chloro-pyrrolo[2,3-b]pyridin-1-yl)-3-phenyl-propyl]-methyl-amine The crude mixture from the previous step was dissolved in MeNH$_2$ (33% in EtOH, 5 mL) and heated to 130° C. via microwave for 1 hour. The mixture was concentrated, and the residue was purified via flash chromatography (DCM/MeOH/NH$_4$OH) to provide [3-(4-Chloro-pyrrolo[2,3-b]pyridin-1-yl)-3-phenyl-propyl]-methyl-amine (28 mg), which was dissolved in EtOAc and 2 equivalents of HCl (1 M in Et$_2$O) to give the corresponding hydrochloride salt (29 mg). MS M+H=306.

Example 24

[3-(4-Methoxy-pyrrolo[2,3-b]pyridin-1-yl)-3-phenyl-propyl]-methyl-amine

SCHEME AA

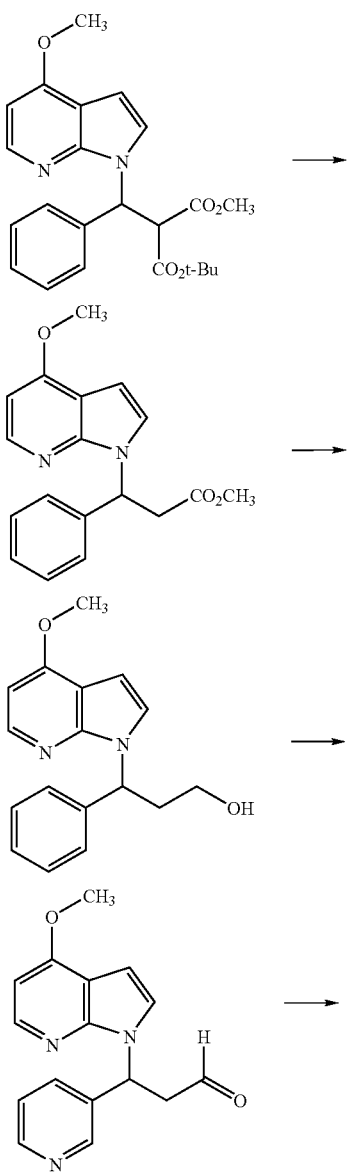

-continued

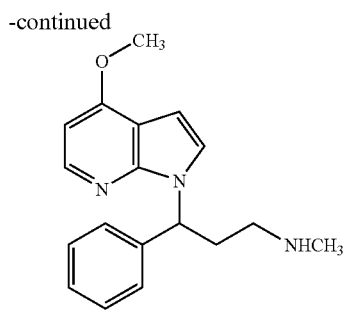

Step 1 2-[(4-Methoxy-pyrrolo[2,3-b]pyridin-1-yl)-phenyl-methyl]-malonic acid tert-butyl ester methyl ester The 2-Benzylidene-malonic acid tert-butyl ester methyl ester used in this step was prepared from tert-butyl-methyl-malonate and benzaldeyde according to the procedure of Example 4 (36% yield, 4.53 g).

2-[(4-Methoxy-pyrrolo[2,3-b]pyridin-1-yl)-phenyl-methyl]-malonic acid tert-butyl ester methyl ester was prepared from 4-methoxy-1H-pyrrolo[2,3-b]pyridine (WO03/082289) and 2-benzylidene-malonic acid tert-butyl ester methyl ester using the procedure of Example 7, and was used without purification.

Step 2 3-(4-Methoxy-pyrrolo[2,3-b]pyridin-1-yl)-3-phenyl-propionic acid methyl ester 3-(4-Methoxy-pyrrolo[2,3-b]pyridin-1-yl)-3-phenyl-propionic acid methyl ester was prepared from 2-[(4-methoxy-pyrrolo[2,3-b]pyridin-1-yl)-phenyl-methyl]-malonic acid tert-butyl ester methyl ester using the procedure of Example 7 (677 mg).

Step 3 3-(4-Methoxy-pyrrolo[2,3-b]pyridin-1-yl)-3-phenyl-propan-1-ol 3-(4-Methoxy-pyrrolo[2,3-b]pyridin-1-yl)-3-phenyl-propan-1-ol was prepared from 3-(4-methoxy-pyrrolo[2,3-b]pyridin-1-yl)-3-phenyl-propionic acid methyl ester following the procedure of Example 7, and was used in the next step without purification.

Step 4 3-(4-Methoxy-pyrrolo[2,3-b]pyridin-1-yl)-3-phenyl-propionaldeyde

To a RT mixture of Dess-Martin periodane (1.69 g, 3.99 mmol) in DCM (50 mL) was added 3-(4-methoxy-pyrrolo[2,3-b]pyridin-1-yl)-3-phenyl-propan-1-ol (563 mg, 2.0 mmol). The reaction was stirred at RT for 2 h and then poured in a saturated solution of NaHCO$_3$. The organic layer was separated, and the aqueous was extracted with a mixture DCM/EtOAc (2/1). The combined organic layers were dried over MgSO$_4$, filtered and concentrated to give 3-(4-Methoxy-pyrrolo[2,3-b]pyridin-1-yl)-3-phenyl-propionaldeyde, which was used in the next step without further purification.

Step 5 [3-(4-Methoxy-pyrrolo[2,3-b]pyridin-1-yl)-3-phenyl-propyl]-methyl-amine To a RT solution of MeNH$_2$.HCl (2.17 g, 31.9 mmol) in MeOH (40 mL) was added NaOH (319 mg, 7.98 mmol). The resulting mixture was stirred for 20 min. Then a solution of 3-(4-methoxy-pyrrolo[2,3-b]pyridin-1-yl)-3-phenyl-propionaldeyde (2.0 mmol) in MeOH (20 mL) was added, and the resulting mixture was stirred for 2 h. To this solution was added NaCNBH$_4$ (125 mg, 2.0 mmol), and the mixture was stirred for 1 h, poured into water, and extracted with EtOAc. The organic layer was washed with water and brine, dried over MgSO$_4$, filtered, concentrated, and purified via preparative TLC, affording [3-(4-Methoxy-pyrrolo[2,3-b]pyridin-1-yl)-3-phenyl-propyl]-methyl-amine (123 mg, 21% 3 steps yield). This compound was dissolved in EtOAc, and converted into the corresponding hydrochloride salt by the addition of 1 equivalent of HCl (1 M in Et$_2$O) to give 107 mg of the corresponding HCl salt.

Example 25

SCHEME BB

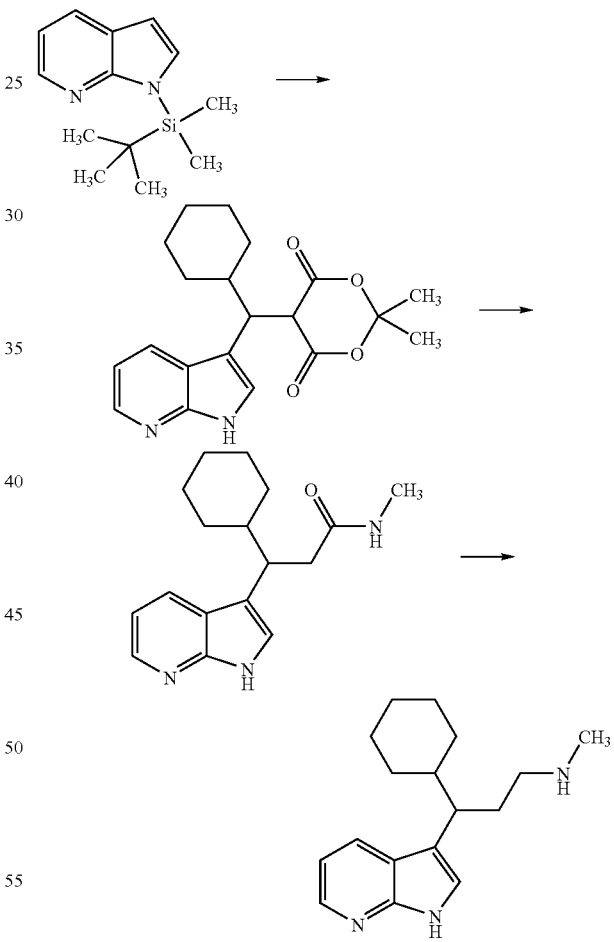

Step 1 5-[Cyclohexyl-(1H-pyrrolo[2,3-b]pyridin-3-yl)-methyl]-2,2-dimethyl-[1,3]dioxane-4,6-dione 5-[Cyclohexyl-(1H-pyrrolo[2,3-b]pyridin-3-yl)-methyl]-2,2-dimethyl-[1,3]dioxane-4,6-dione was prepared following the procedure of Example 1 using cyclohexyl magnesium bromide.

Step 2 3-Cyclohexyl-N-methyl-3-(1H-pyrrolo[2,3-b]pyridin-3-yl)-propionamide

A mixture of 5-[cyclohexyl-(1H-pyrrolo[2,3-b]pyridin-3-yl)-methyl]-2,2-dimethyl-[1,3]dioxane-4,6-dione (560 mg, 1.57 mmol), pyridine (8 mL) and MeNH$_2$ (2 M in THF, 16 mL) heated to 120° C. in sealed vial for 3 h. The reaction was cooled to RT and poured into water. The pH was adjusted to 7. And the resulting solution was extracted 5 times with EtOAc (100 mL) and 3 times with DCM (200 mL). The organic layers were combined, dried over MgSO$_4$, filtered and concentrated, affording crude 3-Cyclohexyl-N-methyl-3-(1H-pyrrolo[2,3-b]pyridin-3-yl)-propionamide (270 mg), which was used in the next step without purification.

Step 3 [3-Cyclohexyl-3-(1H-pyrrolo[2,3-b]pyridin-3-yl)-propyl]-methyl-amine

To a RT solution of 3-cyclohexyl-N-methyl-3-(1H-pyrrolo[2,3-b]pyridin-3-yl)-propionamide (170 mg, 0.95 mmol) in THF (10 mL) was added LAH (1 M in THF, 1.5 mL). The mixture was stirred at RT overnight, and an additional LAH (1 M in THF, 2 mL) was added. The resulting mixture was refluxed for 4 hours and then quenched by addition of freshly ground Na$_2$SO$_4$.10H$_2$O (3 g). After stirring for 1 hour, the solids were filtered off and the filtrate was concentrated and purified via preparative HPLC to give [3-Cyclohexyl-3-(1H-pyrrolo[2,3-b]pyridin-3-yl)-propyl]-methyl-amine. MS M+H=272.

Example 26

3-(4-Isopropoxy-1H-pyrrolo[2,3-b]pyridin-3-yl)-3-phenyl-propyl]-methyl-amine

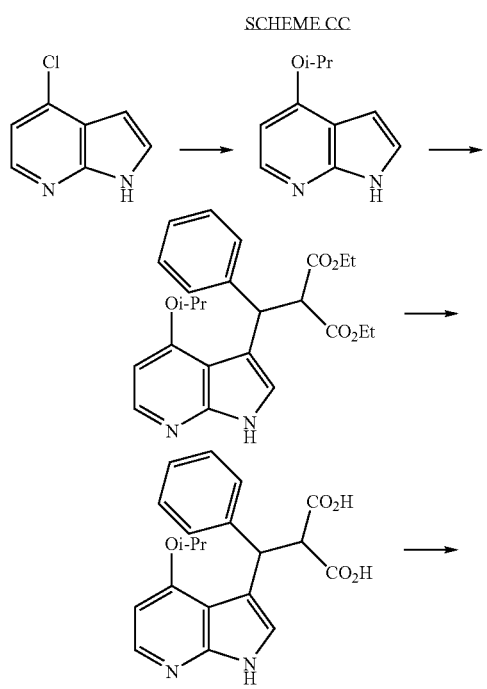

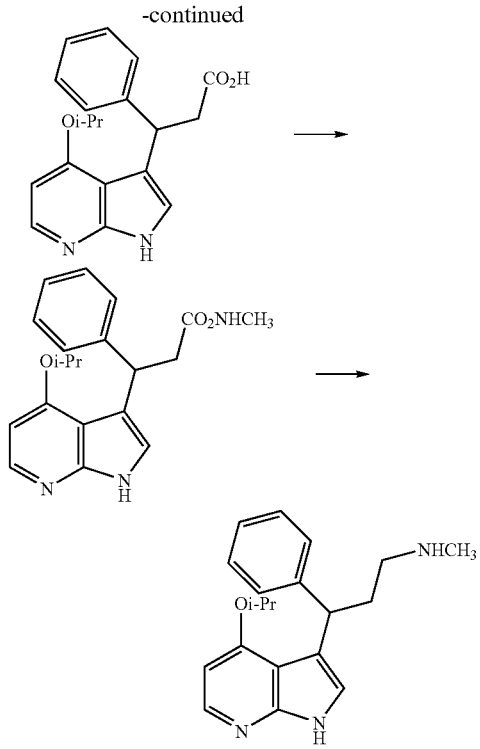

Step 1 4-Isopropoxy-1H-pyrrolo[2,3-b]pyridine

A mixture of 4-chloro-1H-pyrrolo[2,3-b]pyridine (1.24 g, 8.13 mmol), K(i-Pr)O (3.2 g, 32.5 mmol) and celite (1.9 g) in toluene (150 mL) was refluxed for 24 h. The reaction mixture was cooled to 80° C. and quenched by addition of water. The suspension was cooled to RT, and celite was collected by filtration and triturated with DCM. The filtrate was extracted with chloroform and the combined organic layers were dried onto silica and purified via flash chromatography (hexane/EtOAc), affording 4-Isopropoxy-1H-pyrrolo[2,3-b]pyridine (295 mg, 21% yield).

Step 2 2-[(4-Isopropoxy-1H-pyrrolo[2,3-b]pyridin-3-yl)-phenyl-methyl]-malonic acid diethyl ester 2-[(4-Isopropoxy-1H-pyrrolo[2,3-b]pyridin-3-yl)-phenyl-methyl]-malonic acid diethyl ester was prepared from 4-isopropoxy-1H-pyrrolo[2,3-b]pyridine using the procedure of step 1 of Example 3 (68% yield, 479 mg).

Step 3 2-[(4-Isopropoxy-1H-pyrrolo[2,3-b]pyridin-3-yl)-phenyl-methyl]-malonic acid 2-[(4-Isopropoxy-1H-pyrrolo[2,3-b]pyridin-3-yl)-phenyl-methyl]-malonic acid 100 was prepared from 2-[(4-isopropoxy-1H-pyrrolo[2,3-b]pyridin-3-yl)-phenyl-methyl]-malonic acid diethyl ester using the procedure of step 2 of Example 3 (80% yield, 335 mg).

Step 4 2-(4-Isopropoxy-1H-pyrrolo[2,3-b]pyridin-3-yl)-phenyl-propionic acid 2-(4-Isopropoxy-1H-pyrrolo[2,3-b]pyridin-3-yl)-phenyl-propionic acid was prepared from 2-[(4-isopropoxy-1H-pyrrolo[2,3-b]pyridin-3-yl)-phenyl-methyl]-malonic acid using the procedure of step 3 of Example 3 (270 mg).

Step 5 2-(4-Isopropoxy-1H-pyrrolo[2,3-b]pyridin-3-yl)-N-methyl-3-phenyl-propionamide A mixture of 2-(4-isopropoxy-1H-pyrrolo[2,3-b]pyridin-3-yl)-phenyl-propionic acid (270 mg, 0.83 mmol), MeNH$_2$.HCl (69 mg, 1.04 mmol), TEA (0.43 mL, 3.04 mmol), EDCI (199 mg, 1.04 mmol) and HOBt (141 mg, 1.04 mmol) in DCM (50 mL) was stirred at RT overnight. The reaction mixture was then washed successively with water (50 mL), 3 times with NaHCO$_3$ (saturated solution, 50 mL), water (50 mL) and brine (50 mL). The organic layer was dried over MgSO$_4$, filtered, concentrated, and the pale yellow solid residue was triturated with Et$_2$O and hexane to give 2-(4-Isopropoxy-1H-pyrrolo[2,3-b]pyridin-3-yl)-N-methyl-3-phenyl-propionamide as a white solid (175 mg, 62% yield).

Step 6 [3-(4-Isopropoxy-1H-pyrrolo[2,3-b]pyridin-3-yl)-3-phenyl-propyl]-methyl-amine To a solution of 2-(4-isopropoxy-1H-pyrrolo[2,3-b]pyridin-3-yl)-N-methyl-3-phenyl-propionamide (175 mg, 0.52 mmol) in THF (10 mL) was added LAH (1 M in THF, 1.56 mL). The reaction mixture was refluxed for 24 h, cooled to RT, and quenched by addition of water (60 µL) and NaOH (1 M, 60 µL) followed by water (180 µL). The organic layer was separated, dried over MgSO$_4$, filtered and concentrated. The resulting clear oil was acidified with HCl, concentrated to a solid residue, which was triturated with EtOAc and HCl (1M in Et$_2$O), affording [3-(4-Isopropoxy-1H-pyrrolo[2,3-b]pyridin-3-yl)-3-phenyl-propyl]-methyl-amine hydrochloride (95 mg).

Example 27

[3-(4-Chloro-1H-pyrrolo[2,3-b]pyridin-3-yl)-3-pyridin-3-yl-propyl]-methyl-amine

SCHEME DD

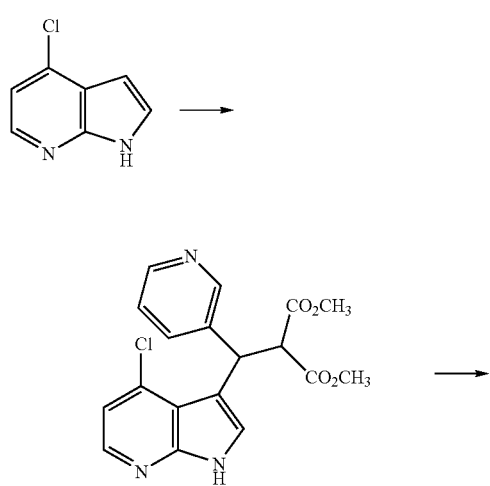

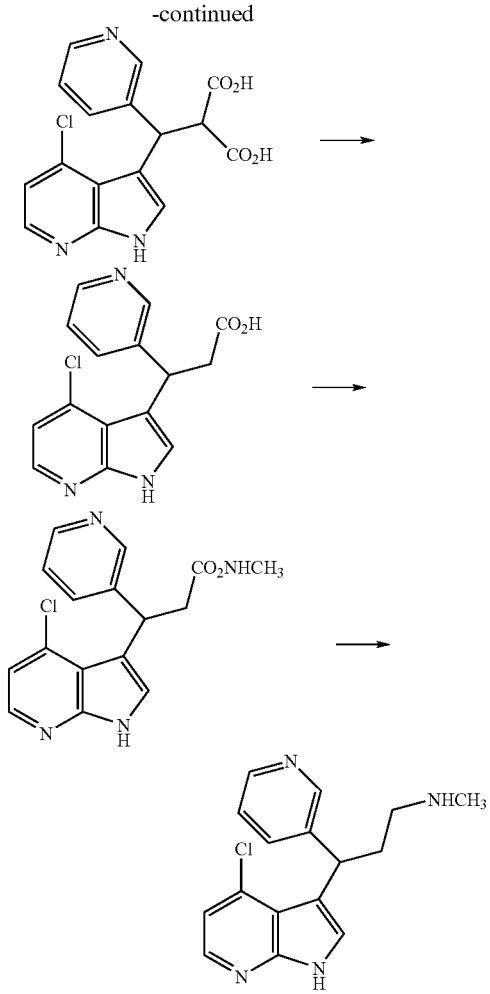

Step 1 2-[(4-Chloro-1H-pyrrolo[2,3-b]pyridin-3-yl)pyridin-3-yl-methyl]-malonic acid dimethyl ester To a 0° C. suspension of 4-chloro-1H-pyrrolo[2,3-b]pyridine (0.5 g, 3.27 mmol) in toluene (15 ml) was added i-PrMgCl (1.5 M in THF, 2.4 ml, 3.60 mmol) and stirred at RT for 30 min, afterwhich a solution of 2-pyridin-3-yl-methylene-malonic acid dimethyl ester (867 mg, 3.92 mmol) in toluene (4 mL) was added dropwise. The resulting mixture was stirred for 1 h, quenched by addition of a saturated solution of NH$_4$Cl. The mixture was diluted with H$_2$O and extracted twice with EtOAc/MeOH (95/5). The combined organic layers were dried over MgSO$_4$, filtered and concentrated. The residue was triturated with a mixture of EtOAc/hexane (3/7) to affording the compound 104 as an off-white solid (746 mg, 61% combined yield).

Step 2 2-[(4-Chloro-1H-pyrrolo[2,3-b]pyridin-3-yl)-pyridin-3-yl-methyl]-malonic acid 2-[(4-Chloro-1H-pyrrolo[2,3-b]pyridin-3-yl)-pyridin-3-yl-methyl]-malonic acid 105 was prepared from 2-[(4-chloro-1H-pyrrolo[2,3-b]pyridin-3-yl)pyridin-3-yl-methyl]-malonic acid dimethyl ester following the procedure of step 2 of Example 3.

Step 3 3-(4-Chloro-1H-pyrrolo[2,3-b]pyridin-3-yl)-3-pyridin-3-yl-propionic acid 3-(4-Chloro-1H-pyrrolo[2,3-b]pyridin-3-yl)-3-pyridin-3-yl-propionic acid 106 was prepared from 2-[(4-chloro-1H-pyrrolo[2,3-b]pyridin-3-yl)-pyridin-3-yl-methyl]-malonic acid following the procedure of step 3 of Example 3 (785 mg).

Step 4 3-(4-Chloro-1H-pyrrolo[2,3-b]pyridin-3-yl)-N-methyl-3-pyridin-3-yl-propionamide 3-(4-Chloro-1H-pyrrolo[2,3-b]pyridin-3-yl)-N-methyl-3-pyridin-3-yl-propionamide was prepared from 3-(4-chloro-1H-pyrrolo[2,3-b]pyridin-3-yl)-3-pyridin-3-yl-propionic acid following the procedure of step 4 of Example 3 (63% yield, 495 mg).

Step 5 [3-(4-Chloro-1H-pyrrolo[2,3-b]pyridin-3-yl)-3-pyridin-3-yl-propyl]-methyl-amine To a slurry of 3-(4-chloro-1H-pyrrolo[2,3-b]pyridin-3-yl)-N-methyl-3-pyridin-3-propionamide (200 mg, 0.64 mmol) in THF (20 mL) was added $BH_3$.THF (1 M in THF, 6.4 mL). The resulting mixture was refluxed for 45 min, then quenched by addition of HCl. The reaction mixture was stirred at RT for several hours until no more gas evolution was observed, it was then basified with KOH (50% in water) and extracted with EtOAc. The organic layer was separated, dried over $MgSO_4$, filtered and concentrated. The residue was dissolved in isopropanol/$Et_2O$ and HCl (1 M in $Et_2O$) was added. The white precipitate was collected by filtration under $N_2$, affording [3-(4-Chloro-1H-pyrrolo[2,3-b]pyridin-3-yl)-3-pyridin-3-yl-propyl]-methyl-amine hydrochloride in 56% yield (120 mg).

Example 28

Formulations

Pharmaceutical preparations for delivery by various routes are formulated as shown in the following Tables. "Active ingredient" or "Active compound" as used in the Tables means one or more of the Compounds of Formula I.

Composition for Oral Administration

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
| --- | --- |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | grams |
| --- | --- |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 29

Screening for Human Serotonin Transporter (hSERT) Antagonists Using a Scintillation Proximity Assay (SPA)

The screening assay of this example was used to determine the affinity of ligands at the hSERT transporter by competition with [$^3$H]-Citalopram.

Scintillation Proximity Assay (SPA) works by bringing radioligand within close proximity to the bead's scintillant to stimulate light emission. In this assay, the receptor-containing membranes were pre-coupled to the SPA beads and the binding of the appropriate radioligand to the transporter was measured. The light emission was proportional to the amount of bound radioligand. Unbound radioligand produced no signal as a result of distant proximity to scintillant (lack of energy transfer).

HEK-293 cells (Tatsumi et al., Eur. J. Pharmacol. 1997, 30, 249-258) stably expressing recombinant hSERT were maintained with media (DMEM high glucose with 10% FBS, 300 µg/ml G418 and 2 mM L-Glutamine) and incubated at 37° C. with 5% $CO_2$. Cells are released from culture flasks using PBS for 1-2 minutes. The cells were subsequently centrifuged at 1000 g's for 5 minutes and resuspended in PBS prior to being used in the membrane preparation.

Cell membranes were prepared using a membrane preparation buffer of 50 mM TRIS (pH 7.4). Cell membranes were prepared from a single cube (7.5×10$^9$ cells total). Cells were homogenized using a Polytron (setting medium for a 4 second burst). The homogenate was then centrifuged at 48,000×g for 15 minutes, the supernatant subsequently removed and discarded, and the pellet resuspended with fresh buffer. After a second centrifugation, the pellet was re-homogenized and brought to a final volume determined during the assay. Typically, membrane portions were aliquoted in 3 mg/ml (w:v). and stored at −80° C.

For Scintillation Proximity Assay $IC_{50}/K_i$ determination, 50 mM Tris-HCl and 300 mM NaCl, (pH 7.4) buffers were utilized. Compounds of the invention were diluted from 10 mM to 0.1 nM FAC (10 point curves, whole log/half log dilutions) via a Beckman Biomek 2000 using a serial dilution protocol. The test compounds were then transferred (20 µl/well) and the [$^3$H]-Citalopram radioligand was added at 50 µl/well. Membrane and beads were prepared to a ratio of 10 µg: 0.7 mg, with 0.7 mg PVT-WGA Amersham beads (Cat# RPQ0282V) added per well. 130 µl of the membrane: bead mixture was added to the assay plate. The mixtures were allowed to stand at room temperature for one hour, and were then counted on a Packard TopCount LCS, a generic Scintillation Proximity Assay counting protocol settings (Energy Range: Low, Efficiency Mode: Normal, Region A: 1.50-35.00, Region B: 1.50-256.00, Count Time (min.): 0.40, Background Subtract: none, Half-Life Correction: no, Quench Indicator: tSIS, Platemap blank subtraction: No, Cross talk reduction: Off).

The % inhibition was calculated for each compound tested [(Compound counts per minute (CPM) at maximum concentration-Non-Specific CPM)/Total CPM*100]. The concentration producing 50% inhibition ($IC_{50}$) was determined using an iterative non-linear curve fitting technique with Activity Base/Xlfit using the following equation:

$$y = \frac{\max - \min}{1 + (IC50/x)^n} + \min$$

where max=total binding, min=non specific binding, x=concentration (M) of the tested compound and n=Hill slope. The inhibition dissociation constant (Ki) of each compound was determined according to the method of Cheng-Prusoff and then converted into negative logarithm (pKi) of the Ki.

Using the above procedure, compounds of the invention were found to have affinity for human serotonin transporter. For example, [(S)-3-(4-Methoxy-1H-pyrrolo[2,3-b]pyridin-3-yl)-3-phenyl-propyl]-methyl-amine exhibited an $IC_{50}$ of approximately 8.75 using the above assay.

Example 30

Screening for Compounds Active at Human Norepinephrine Transporter (hNET) Using a Scintillation Proximity Assay (SPA)

This assay was used to determine the affinity of ligands for the hNET transporter by competition with [$^3$H]-Nisoxetine. As in the hSERT assay of the above example, receptor-containing membranes were pre-coupled to the SPA beads and the binding of the appropriate radioligand to the transporter was measured. The light emission was proportional to the amount of bound radioligand, with unbound radioligand producing no signal.

HEK-293 cells (Tatsumi et al., Eur. J. Pharmacol. 1997, 30, 249-258) stably expressing recombinant hNET (Clone: HEK-hNET #2) were maintained with media (DMEM hi glucose with 10% FBS, 300 µg/ml G418 and 2 mM L-Glutamine) and incubated at 37° C. with 5% $CO_2$. Cells were released from culture flasks using PBS for 1-2 minutes. The cells were subsequently centrifuged at 1000 g's for 5 minutes and resuspended in PBS prior to being used in the membrane preparation.

Cell membranes were prepared using a membrane preparation buffer of 50 mM TRIS (pH 7.4). Cell membranes were prepared from a single cube (7.5×10$^9$ cells total). Cells were homogenized using a Polytron (setting medium for a 4 second burst). The homogenate was then centrifuged at 48,000×g for 15 minutes, the supernatant subsequently removed and discarded, and the pellet resuspended with fresh buffer. After a second centrifugation, the pellet was re-homogenized and brought to a final volume determined during the assay. Typically, membrane portions were aliquoted in 3-6 mg/ml (w:v). and stored at −80° C.

3[H] Nisoxetine radioligand (Amersham Cat. # TRK942 or Perkin Elmer Cat. # NET1084, specific activity: 70-87 Ci/mmol, stock concentration: 1.22e-5 M, final concentration: 8.25e-9 M), and 50 mM Tris-HCl, 300 mM NaCl, (pH 7.4) buffers were used for Scintillation Proximity Assay IC$_{50}$/K$_i$ determination. Compounds of the invention were diluted from 10 mM to 0.1 nM FAC (10 point curves, whole log/half log dilutions) via a Beckman Biomek 2000 using a serial dilution protocol. The test compounds were then transferred (20 µl/well) and the radioligand was added at 50 µl/well. Membrane and beads were prepared to a ratio of 10 µg:0.7 mg, with 0.7 mg PVT-WGA Amersham beads (Cat# RPQ0282V) added per well. 130 µl of the membrane:bead mixture was added to the assay plate. The mixtures were allowed to stand at room temperature for one hour, and were then counted on a Packard TopCount LCS, a generic SPA counting protocol settings (Energy Range: Low, Efficiency Mode: Normal, Region A: 1.50-35.00, Region B: 1.50-256.00, Count Time (min.): 0.40, Background Subtract: none, Half-Life Correction: no, Quench Indicator: tSIS, Platemap blank subtraction: No, Cross talk reduction: Off).

The % inhibition was calculated for each compound tested [(Compound CPM at maximum concentration-Non-Specific CPM)/Total CPM*100]. The concentration producing 50% inhibition (IC$_{50}$) was determined using an iterative non-linear curve fitting technique with Activity Base/Xlfit using the following equation:

$$y = \frac{max - min}{1 + (IC50/x)^n} + min$$

where max=total binding, min=non specific binding, x=concentration (M) of the tested compound and n=Hill slope. The inhibition dissociation constant (Ki) of each compound was determined according to the method of Cheng-Prusoff and then converted into negative logarithm (pKi) of the Ki.

Using the above procedure, compounds of the invention were found to have affinity for the human norepinephrine transporter. For example, [(S)-3-(4-Methoxy-1H-pyrrolo[2,3-b]pyridin-3-yl)-3-phenyl-propyl]-methyl-amine exhibited an IC$_{50}$ of approximately 7.75 using the above assay.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of formula I:

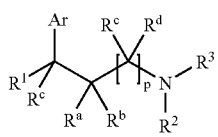

I or a pharmaceutically acceptable salt thereof, wherein:
p is 1 or 2;
Ar is:
  pyrrolo[2,3-b]pyridinyl selected from pyrrolo[2,3-b]pyridin-1-yl, pyrrolo[2,3-b]pyridin-2-yl, and pyrrolo[2,3-b]pyridin-3-yl, each optionally substituted;
R$^1$ is:
  (a) aryl selected from phenyl and naphthyl, each optionally substituted; or
  (b) heteroaryl selected from indolyl, pyridinyl, thienyl, furanyl, pyrimidinyl, pyridazinyl, pyrazinyl, oxazolyl, thiazolyl, isoxazolyl, isothiazolyl, imidazolyl, pyrazolyl, quinolinyl and isoquinolinyl, each optionally substituted;
  (c) optionally substituted arylalkyl;
  (d) optionally substituted heteroarylalkyl;
  (e) cycloalkyl;
  (f) cycloalkylmethyl; or
  (g) branched alkyl;
R$^2$ is:
  (a) hydrogen;
  (b) alkyl;
  (c) hydroxyalkyl;
  (d) alkoxyalkyl;
  (e) benzyl; or
  or R$^2$ is a bond that connects the nitrogen atom to one of the ring carbon atoms of Ar;
R$^3$ is:
  (a) hydrogen;
  (b) alkyl;
  (c) hydroxyalkyl;
  (d) alkoxyalkyl;
  (e) benzyl; or
  (f) R$^2$ and R$^3$ together with the nitrogen to which they are attached may form an optionally substituted four to seven membered ring that optionally includes an additional heteroatom selected from N, O and S;
R$^a$ is:
  hydrogen;
R$^b$ is:
  hydrogen;
R$^c$ and R$^d$ each is:
  hydrogen; and
R$^e$ is hydrogen or alkyl.

2. The compound according to claim 1, wherein p is 1.

3. The compound according to claim 1, wherein R$^1$ is aryl, heteroaryl, or cycloalkyl, each of which is optionally substituted.

4. The compound according to claim 1, wherein each of R$^2$ and R$^3$ is independently hydrogen or alkyl.

5. The compound according to claim 1, wherein R$^2$ is a bond that connects the nitrogen atom to one of the ring carbon atoms of Ar.

6. The compound according to claim 1 of the formula:

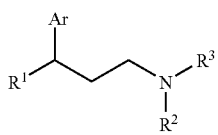

II or a pharmaceutically acceptable salt thereof,
wherein:
R$^2$ is hydrogen, alkyl, or a bond that connects the nitrogen atom to one of the ring carbon atoms of Ar;

R³ is hydrogen or alkyl; and
Ar and R¹ are as recited in claim 1.

7. The compound according to claim 6, wherein R¹ is phenyl, pyridinyl, or cyclohexyl, each of which is optionally substituted.

8. The compound according to claim 6 of the formula:

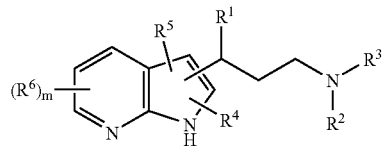

III wherein
  m is an integer from 0 to 3;
  each of $R^4$ and $R^5$ is independently: hydrogen; alkoxy, cyano, alkyl, halo, —S(O)$_r R^f$; and —C(=O)NR$^g R^h$; wherein r is an integer from 0 to 2, and each of $R^f$, $R^g$, and $R^h$ is independently hydrogen or alkyl;
  each $R^6$ is independently: alkoxy, cyano, alkyl, amino, alkylamino, dialkylamino, halo, —S(O)$_r R^f$; and —C(=O)NR$^g R^h$; wherein r is an integer from 0 to 2, and each of $R^f$, $R^g$, and $R^h$ is independently hydrogen or alkyl; and
  R¹, R² and R³ are as recited in claim 1.

9. A pharmaceutical composition comprising a compound of claim 1 and a pharmaceutically acceptable carrier.

* * * * *